US008722340B2

(12) United States Patent
Claret

(10) Patent No.: US 8,722,340 B2
(45) Date of Patent: May 13, 2014

(54) JAB1 AS A PROGNOSTIC MARKER AND A THERAPEUTIC TARGET FOR HUMAN CANCER

(75) Inventor: Francois Claret, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1337 days.

(21) Appl. No.: 11/874,838

(22) Filed: Oct. 18, 2007

(65) Prior Publication Data

US 2009/0148868 A1 Jun. 11, 2009

Related U.S. Application Data

(62) Division of application No. 10/858,869, filed on Jun. 1, 2004, now abandoned.

(60) Provisional application No. 60/474,048, filed on May 29, 2003.

(51) Int. Cl.
*G01N 33/53* (2006.01)

(52) U.S. Cl.
USPC ............................................. 435/7.1

(58) Field of Classification Search
None
See application file for complete search history.

(56) References Cited

U.S. PATENT DOCUMENTS

| | | | |
|---|---|---|---|
| 2,868,691 A | 1/1959 | Porush et al. | 222/192 |
| 3,095,355 A | 6/1963 | Abramson et al. | 424/498 |
| 4,736,866 A | 4/1988 | Leder et al. | 800/10 |
| 5,162,215 A | 11/1992 | Bosselman et al. | 800/23 |
| 5,234,933 A | 8/1993 | Marnett et al. | 514/327 |
| 5,279,833 A | 1/1994 | Rose | 424/450 |
| 5,286,634 A | 2/1994 | Stadler et al. | 435/468 |
| 5,326,902 A | 7/1994 | Seipp et al. | 560/254 |
| 5,399,346 A | 3/1995 | Anderson et al. | 424/93.21 |
| 5,489,742 A | 2/1996 | Hammer et al. | 800/9 |
| 5,550,316 A | 8/1996 | Mintz | 800/10 |
| 5,573,933 A | 11/1996 | Seamark et al. | 800/25 |
| 5,614,396 A | 3/1997 | Bradley et al. | 435/463 |
| 5,625,125 A | 4/1997 | Bennett et al. | 800/3 |
| 5,627,158 A | 5/1997 | Cho-Chung | 514/44 |
| 5,641,484 A | 6/1997 | Hung et al. | 424/93.2 |
| 5,643,567 A | 7/1997 | Hung et al. | 424/93.2 |
| 5,646,008 A | 7/1997 | Thompson et al. | 435/69.1 |
| 5,648,061 A | 7/1997 | Bernstein et al. | 424/9.2 |
| 5,651,964 A | 7/1997 | Hung et al. | 424/93.2 |
| 5,734,033 A | 3/1998 | Reed | 536/23.1 |
| 5,741,957 A | 4/1998 | Doboer et al. | 800/7 |
| 6,177,272 B1 | 1/2001 | Nabel et al. | 435/320.1 |
| 6,218,181 B1 | 4/2001 | Verma et al. | 435/369 |
| 6,251,601 B1 | 6/2001 | Bao et al. | 435/6 |
| 2002/0156012 A1 | 10/2002 | Lyapina et al. | 514/12 |
| 2002/0162126 A1 | 10/2002 | Beach et al. | 800/8 |
| 2003/0148954 A1 | 8/2003 | Bresnick et al. | 514/12 |
| 2003/0153097 A1 | 8/2003 | Deshaies et al. | 436/518 |
| 2003/0166243 A1 | 9/2003 | Cope et al. | 435/226 |

FOREIGN PATENT DOCUMENTS

| | | |
|---|---|---|
| EP | 0856582 | 5/1998 |
| EP | 1104808 | 6/2001 |
| WO | WO 93/25521 | 12/1993 |
| WO | WO 00/77258 | 12/2000 |
| WO | WO 02/055536 | 7/2002 |
| WO | WO 02/068645 | 9/2002 |
| WO | WO 03/022052 | 3/2003 |
| WO | WO 2004/053075 | 6/2004 |

OTHER PUBLICATIONS

Wu (J. Pathol. 195(1):53-65, 2001.)*
Lucentini (The Scientist, p. 20, Dec. 20, 2004).*
Chen et al. (Molecular and Cellular Proteomics 1:304-313, 2002).*
Hengst et al. Science 271(5257):1861-1864, 1996.*
Esteva et al. Clinical Cancer Research 9:5652-5659, 2003.*
Shen et al International Journal of Oncology 17:749-754, 2000.*
Catzavelos et al., "Decreased Levels of the cell-cycle inhibitor p27Kip1 protein: Prognostic implications in primary breast cancer," *Nature*, 3:227-230, 1997.
Chen et al., "Discordant Protein and mRNA Expression in Lung Adenocarcinomas," *Molecular and Cellular Proteomics*, 1:304-313, 2002.
Claret et al., "A new group of conserved coactivators that increase the specificity of AP-1 transcription factors," *Nature*, 383:453-457, 1996.
Esteva et al., "Expression of erbB/HER Receptors, Heregulin and P38 in Primary Breast Cancer using Quantitative Immunohistochemistry," *Pathology Oncol. Res.*, 7:171-177, 2001.
Esteva et al., "Jun activation domain binding protein 1 expression is associated with low p27(Kip1)levels in node-negative breast cancer," *Clin. Cancer Res.*, 9:5652-5659, 2003.
Fukumoto et al., "Prognostic significance of localized p27Kip1 and potential role of Jab1/CsN5 in pancreatic cancer," *Oncology*, 11:277-284, 2004.
Hengst and Reed, "Translational Control of p27Kip1 Accumulation During the Cell Cycle," *Science*, 271:1861-1864, 1996.
Ito et al., "Jun activation domain-binding protein 1 expression in malignant lymphoma of the thyroid: its linkage to degree of malignancy and p27 expression," *Anticancer Res.*, 23:4121-4126, 2003.
Korbonits et al., "Expression of phosphorylated p27(Kip1) protein and Jun activation domain-binding protein 1 in human pituitary tumors," *J. Clin. Endocrinol. Metab.*, 87:2635-2643, 2002.
Lu et al., "siRNA-mediated antitumorigenesis for drug target validation and therapeutics," *Current Opin. Mol. Thera.*, 5:225-234, 2003.
Lucentini, "Gene Association Studies Typically Wrong," *The Scientist*, 18:20, 2004.

(Continued)

*Primary Examiner* — Celine Qian
(74) *Attorney, Agent, or Firm* — Parker Highlander PLLC

(57) ABSTRACT

Methods of diagnosing and prognosticating the development of human cancers, such as breast cancer, colon cancer, and pancreatic cancer, are provided. The diagnostic and prognostic methods include the detection and/or quantifying of the amount of expression of JAB1 in human cells, particularly in relation to the amount of p27 or c-Jun. In addition, methods for reducing the expression of JAB1 protein in cells and inhibiting its interaction with p27 or c-Jun, for example, are provided.

15 Claims, 28 Drawing Sheets

(56) References Cited

OTHER PUBLICATIONS

Porter et al., "Expression of cell-cycle regulators p27Kip1 and cyclin E, alone and in combination, correlate with survival in young breast cancer patients," *Nature*, 3:222-225, 1997.

Rassidakis et al., "Expression of p27(Kip1) and c-Jun activation binding protein 1 are inversely correlated in systemic anaplastic large cell lymphoma," *Clin. Cancer Res.*, 9:1121-1128, 2003.

Shen et al., "Differentiation-Associated Expression and Intracellular Localization of Cyclin-Dependent Kinase Inhibitor p27Kip1 and c-Jun Co-Activator JAB1 in Neuroblastoma," *Int. J. Oncology*, 17:749-754, 2000.

Shi, "Mammalian RNAi for the masses," *Trends Genetics*, 19:9-12, 2003.

Sui et al., "Jab1 expression is associated with inverse expression of p27(kip1) and poor prognosis in epithelial ovarian tumors," *Clin. Cancer Res.*, 7:4130-4135, 2001.

Tomoda et al., "Degradation of the cyclindependent-kinase inhibitor p27Kip1 is instigated by Jab1," *Nature*, 398:160-165, 1995.

Tomoda et al., "The cytoplasmic shuttling and subsequent degradation of p27Kip1 mediated by Jab1/CSN5 and the COP9 signalosome complex," *J. Biol. Chem.*, 277:2302-2310, 2002.

Tsuchida et al., "Expression of cyclin-dependent kinase inhibitor p27/Kip1 and AP-1 coactivator p38/Jab1 correlates with differentiation of embryonal rhabdomyosarcoma," *Jpn. J Cancer Res.*, 93:1000-1006, 2002.

Wu, "Analysing Gene Expression Data from Microarrays to Identify Candidate Genes," *J. Pathology*, 195:53-65, 2001.

Yang et al., "Oncogenic signals of HER-2/neu in regulating the stability of the cyclin-dependent kinase inhibitor p27," *J. Biol. Chem.*, 275:24735-24739, 2000.

Berg et al., "Inverse expression of Jun activation domain binding protein 1 and cell cycle inhibitor p27$^{Kip1}$: influence on proliferation in hepatocellular carcinoma," *Human Pathology*, 38:1621-1627, 2007.

Goto et al., "Immunohistochemical study of Skp2 and Jab1, two key molecules in the degradation of P27, in lung adenocarcinoma," *Pathology International*, 54:675-681, 2004.

Osoegawa et al., "Overexpression of Jun activation domain-binding protein 1 in nonsmall cell lung cancer and its significance in p27 expression and clinical features," *Cancer*, 107:154-161, 2006.

\* cited by examiner

| Cells | Soft-agar growth | Average no. of colonies/dish at 1 week; at 2 weeks | | No. of cells injected in mice | Tumors > 10 mm in diameter by 42 days |
|---|---|---|---|---|---|
| 3T3 Parental (Control) | − | 0 | 0 | 4 x 10⁶ | 0/5 |
| 3T3 JAB1#C3 | + | 145 | 227 | 4 x 10⁶ | 3/5 |
| 3T3 JAB1#C4 | +++ | 165 | 336 | 4 x 10⁶ | 9/10 |

FIG. 4

5'-TTCAACAUGCAGGAAGCUCAG-3' (SEQ ID No: 3)

3'-GUUGUACGUCCUUCGAGUCTT-5' (SEQ ID No:4)

FIG. 10

Depletion of JAB1 by siRNA adenovirus causes accumulation of p27$^{kip1}$ and induces G1 arrest in MDA-MB 231 breast carcinoma cells

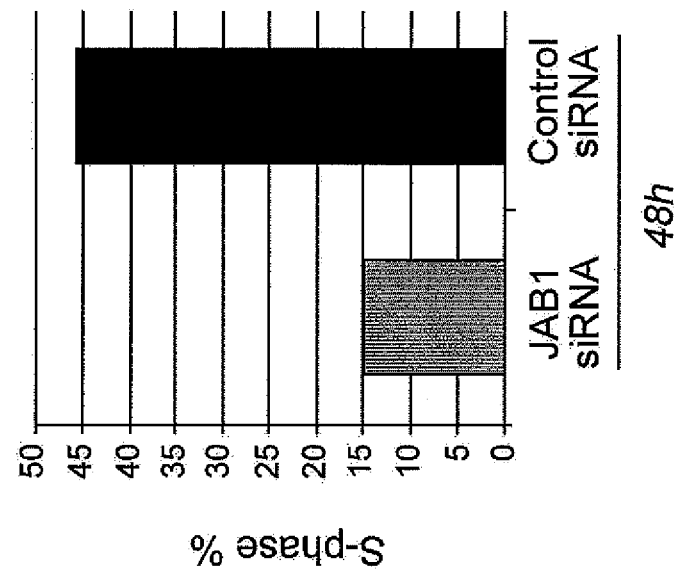
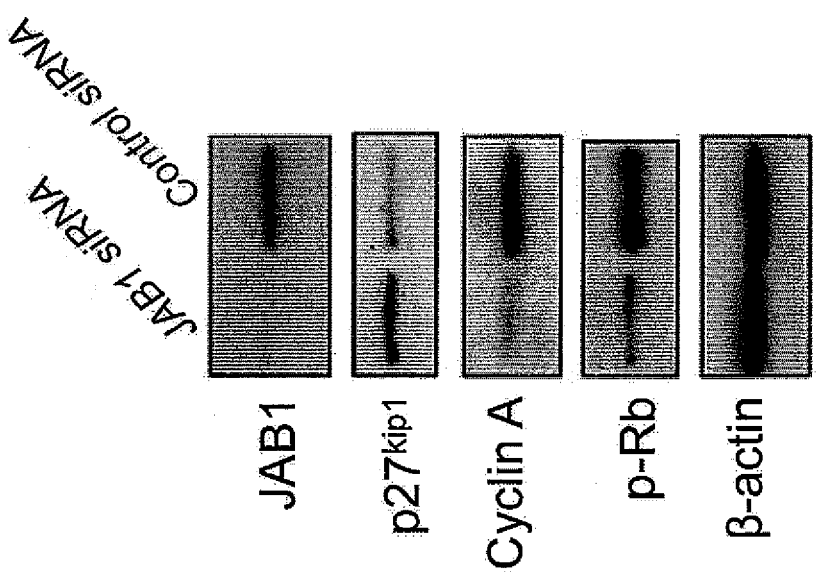
FIG. 14

```
                                                            Ikaros 2
-881 TAATAAAAAA ATTAAACATT GTATTAACTG TAGGAAGAAA ACAAACCAGT TACCCAGATT Ikaros 2
-821 AATTACGCTT TGGGAACAAA TGCGGTTCAC AGGAGTGCCA AAGATTTAAC TGTAACCTGT

GATA-BF-3
-761 TACGAGAACT GAGTACTGGA CATTTTCAGA TCAGTAATGG CACATTATAT ATACGTAGAT

E2F
-601 GTTAACTTTT AACCAAGCGC AAAAAAGCAA TCAAGGAGTA CCCACTGCCT CCTCGCATCG

NMP4/CIZ                                             v-myb
-541 ATAGAAAAAG CCCATCTGCA AGTGAAGTGC AAGCCACCA CGAGCCCGTT ATCTTTTACG AP1        ATF            GATA/Pu120
-481 CATGTACAGT GAGTCATCTT GAAGTAAACG GGAATGCCAT GTTTATCTTC CTCTCAACCA

-421 GCTTCCAGAA CGACTTTTAG CTCAGTTGTA CAACAGACAG CCTTACCTTT TAGTCTTTCA

GATA-BF-1
-361 ACAAACTTAT CTCATTTAAG GTACCTATAC CCAC    AA ACACTTTCCG CCCTCCACAT

MOK-2
-301 CCCGCTCTTA AGGCTCCAGC TACCTTTAAT ATGGCGGAGG CCGAGCCTGC GCATTAGAAG

STAT                          Elk-1       c-Rel
-241 CAGAGAAGGC AAATACCAGT TTCTGGAATA ACGTTACATG CCCTTCTTCC GGTTTTTCCG
                                                                v-Myb
-181 AGACAAGATG TTCTCATTTA AGCAACAAGA AGATTCGTCT CTCGCTATTA CTGTAACTGC

FREAC-7/MEF2/Pax-3/STAT3
-121 TGTTTATATC GTCATGTCCC GGAAAGGTCC CTGTCTTCCC TGAATGGTCT CTACCAACTT

-61 CACCTCCGGT TCTAGGTGTC ATGGCTGCCC CAAGAGTCTA GGTAAGAGTT TGTTCCCGTG

+1 GTGCGGAGGG TCAAGGCCCA CACCCGGAAA CCTAGCGAGG TAAAGTTGCG TCTTGGTTGT

+61 AGAGACGACA ACTTCTCCGC TTCCTCGGCG TAC
```

FIG. 21

```
                        SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
ttcaacatgc aggaagctca g                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
ttctgagctt cctgcatgtt g                                              21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence:  Synthetic
      Primer

<400> SEQUENCE: 3
aacaacaugc aggaagcuca g                                              21
```

```
<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence:  Synthetic
      Primer

<400> SEQUENCE: 4
aacugagcuu ccugcauguu g                                                    21

<210> SEQ ID NO 5
<211> LENGTH: 199
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5
tactctgagc ttcctgcatg ttgttggcca gttcccaggt tttctgggcc ataccgctcc          60
cggacgccgc catcgccgag gaagcggaga agttgtcgtc tctacaacca agacgcaact         120
ttacctcgct aggtttccgg gtgtgggcct gaccctccgc accacgggaa caaactctta         180
cctagactct tgggaattc                                                     199

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6
cacacaaagc ttgaattccc aagagtctag g                                         31

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 7
cacacaaagc tttactctga gcttcttgca t                                         31

<210> SEQ ID NO 8
<211> LENGTH: 1292
<212> TYPE: DNA
<213> ORGANISM: Homo sapiens

<400> SEQUENCE: 8
gaattcccaa gagtctaggt aagagtttgt tcccgtggtg cggagggtca aggcccacac          60
ccggaaacct agcgaggtaa agttgcgtct tggttgtaga gacgacaact tctccgcttc         120
ctcggcgatg gcggcgtccg ggagcggtat ggcccagaaa acctgggaac tggccaacaa         180
catgcaggaa gctcagagta tcgatgaaat ctacaaatac gacaagaaac agcagcaaga         240
aatcctggcg cgaagccct ggactaagga tcaccattac tttaagtact gcaaaatctc         300
agcattggct ctgctgaaga tggtgatgca tgccagatcg ggaggcaact tggaagtgat         360
gggtctgatg ctaggaaagg tggatggtga accatgatc attatggaca gttttgcttt         420
gcctgtggag ggcactgaaa cccgagtaaa tgctcaggct gctgcatatg aatacatggc         480
```

```
tgcatacata gaaaatgcaa aacaggtggg ccaccttgaa aatgcaatcg ggtggtatca      540
tagccaccct ggctatggct gctggctttc tgggattgat gttagtactc agatgctcaa      600
tcagcagttc caggaaccat ttgtagcagt ggtgattgat ccaacaagaa caatatccgc      660
agggaaagtg aatcttggcg cctttaggac atacccaaag ggctacaaac ctcctgatga      720
aggaccttct gagtaccaga ctattccact aataaaata gaagattttg gtgtacactg       780
caaacaatat tatgccttag aagtctcata tttcaaatcc tctttggatc gcaaattgct      840
tgagctgttg tggaataaat actgggtgaa tacgttgagt tcttctagct tgcttactaa      900
tgcagactat accactggtc aggtctttga tttgtctgaa aagttagagc agtcagaagc      960
ccagctggga cgagggagtt tcatgttggg tttagaaacg catgaccgaa aatcagaaga     1020
caaacttgcc aaagctacaa gagacagctg taaaactacc atagaagcta tccatggatt     1080
gatgtctcag gttattaagg ataaactgtt taatcaaatt aacatctctt aaacagtctc     1140
tgagaagtac tttacctgaa agacagtatg agaaaaatat tcaagtacac tttaaaacca     1200
gttacccaaa atctgattag aagtataagg tgctctgaag tgtcctaaat attaatatcc     1260
tgtaataaag ctctttaaaa tgaaaaaaaa aa                                   1292

<210> SEQ ID NO 9
<211> LENGTH: 1510
<212> TYPE: DNA
<213> ORGANISM: Homo sapiens

<400> SEQUENCE: 9
gactatacca ctcccatacc ctataacttt gtttgttcta tttcacacat ataattttcc       60
gagacaagat gttctcattt aagcaacaag aagattcgtc tctcgctatt actgtaactg      120
ctgtttatat cgtcatgtcc cggaaaggtc cctgtcttcc ctgaatggtc tctaccaact      180
tcacctccgg ttctaggtgt catggctgcc ccaagagtct aggtaagagt ttgttcccgt      240
ggtgcggagg gtcaaggccc acacccggaa acctagcgag gtaaagttgc gtcttggttg      300
tagagacgac aacttctccg cttcctcggc gatggcggcg tccgggagcg gtatggccca      360
gaaaacctgg gaactggcca acaacatgca ggaagctcag agtatcgatg aaatctacaa      420
atacgacaag aaacagcagc aagaaatcct ggcggcgaag ccctggacta aggatcacca      480
ttactttaag tactgcaaaa tctcagcatt ggctctgctg aagatggtga tgcatgccag      540
atcgggaggc aacttggaag tgatgggtct gatgctagga aaggtggatg gtgaaaccat      600
gatcattatg gacagttttg ctttgcctgt ggagggcact gaaacccgag taaatgctca      660
ggctgctgca tatgaataca tggctgcata catagaaaat gcaaaacagg ttggccgcct      720
tgaaaatgca atcgggtggt atcatagcca ccctggctat ggctgctggc tttctgggat      780
tgatgttagt actcagatgc tcaatcagca gttccaggaa ccatttgtag cagtggtgat      840
tgatccaaca agaacaatat ccgcaggaaa agtgaatctt ggcgccttta ggacataccc      900
aaagggctac aaacctcctg atgaaggacc ttctgagtac cagactattc cacttaataa      960
aatagaagat tttggtgtac actgcaaaca atattatgcc ttagaagtct catatttcaa     1020
atcctctttg gatcgcaaat tgcttgagct gttgtggaat aaatactggg tgaatacgtt     1080
gagttcttct agcttgctta ctaatgcaga ctataccact ggtcaggtct ttgatttgtc     1140
tgaaaagtta gagcagtcag aagcccagct gggacgaggg agtttcatgt tgggtttaga     1200
aacgcatgac cgaaaatcag aagacaaact tgccaaagct acaagagaca gctgtaaaac     1260
taccatagaa gctatccatg gattgatgtc tcaggttatt aaggataaac tgtttaatca     1320
```

```
aattaacatc tcttaaacag tctctgagaa gtactttacc tgaaagacag tatgagaaaa    1380
atattcaagt aacactttaa aaccagttac ccaaaatctg attagaagta taaggtgctc    1440
tgaagtgtcc taaatattaa tatcctgtaa taaagctctt taaaatgaaa aaaaaaaaa     1500 aaaaaaaaaa                                                          1510
```

<210> SEQ ID NO 10
<211> LENGTH: 334
<212> TYPE: PRT
<213> ORGANISM: Homo sapiens

<400> SEQUENCE: 10

```
Met Ala Ala Ser Gly Ser Gly Met Ala Gln Lys Thr Trp Glu Leu Ala
 1               5                   10                  15

Asn Asn Met Gln Glu Ala Gln Ser Ile Asp Glu Ile Tyr Lys Tyr Asp
             20                  25                  30

Lys Lys Gln Gln Gln Glu Ile Leu Ala Ala Lys Pro Trp Thr Lys Asp
         35                  40                  45

His His Tyr Phe Lys Tyr Cys Lys Ile Ser Ala Leu Ala Leu Leu Lys
     50                  55                  60

Met Val Met His Ala Arg Ser Gly Gly Asn Leu Glu Val Met Gly Leu
 65                  70                  75                  80

Met Leu Gly Lys Val Asp Gly Glu Thr Met Ile Ile Met Asp Ser Phe
                 85                  90                  95

Ala Leu Pro Val Glu Gly Thr Glu Thr Arg Val Asn Ala Gln Ala Ala
            100                 105                 110

Ala Tyr Glu Tyr Met Ala Ala Tyr Ile Glu Asn Ala Lys Gln Val Gly
        115                 120                 125

Arg Leu Glu Asn Ala Ile Gly Trp Tyr His Ser His Pro Gly Tyr Gly
    130                 135                 140

Cys Trp Leu Ser Gly Ile Asp Val Ser Thr Gln Met Leu Asn Gln Gln
145                 150                 155                 160

Phe Gln Glu Pro Phe Val Ala Val Val Ile Asp Pro Thr Arg Thr Ile
                165                 170                 175

Ser Ala Gly Lys Val Asn Leu Gly Ala Phe Arg Thr Tyr Pro Lys Gly
            180                 185                 190

Tyr Lys Pro Pro Asp Glu Gly Pro Ser Glu Tyr Gln Thr Ile Pro Leu
        195                 200                 205

Asn Lys Ile Glu Asp Phe Gly Val His Cys Lys Gln Tyr Tyr Ala Leu
    210                 215                 220

Glu Val Ser Tyr Phe Lys Ser Ser Leu Asp Arg Lys Leu Leu Glu Leu
225                 230                 235                 240

Leu Trp Asn Lys Tyr Trp Val Asn Thr Leu Ser Ser Ser Leu Leu
                245                 250                 255

Thr Asn Ala Asp Tyr Thr Thr Gly Gln Val Phe Asp Leu Ser Glu Lys
            260                 265                 270

Leu Glu Gln Ser Glu Ala Gln Leu Gly Arg Gly Ser Phe Met Leu Gly
        275                 280                 285

Leu Glu Thr His Asp Arg Lys Ser Glu Asp Lys Leu Ala Lys Ala Thr
    290                 295                 300

Arg Asp Ser Cys Lys Thr Thr Ile Glu Ala Ile His Gly Leu Met Ser
305                 310                 315                 320

Gln Val Ile Lys Asp Lys Leu Phe Asn Gln Ile Asn Ile Ser
                325                 330
```

-continued

```
<210> SEQ ID NO 11
<211> LENGTH: 35
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

Leu Ala Lys Ala Thr Arg Asp Ser Cys Lys Thr Thr Ile Glu Ala Ile
  1               5                  10                  15

His Gly Leu Met Ser Gln Val Ile Lys Asp Lys Leu Phe Asn Gln Ile
             20                  25                  30

Asn Ile Ser
         35

<210> SEQ ID NO 12
<211> LENGTH: 45
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 12

His His Tyr Phe Lys Tyr Cys Lys Ile Ser Ala Leu Ala Leu Leu Lys
  1               5                  10                  15

Met Val Met His Ala Arg Ser Gly Gly Asn Leu Glu Val Met Gly Leu
             20                  25                  30

Met Leu Gly Lys Val Asp Gly Glu Thr Met Ile Ile Met
         35                  40                  45

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 13

Leu Ala Lys Ala Thr Arg Asp Ser Cys Lys Thr Thr Ile Glu Ala Ile
  1               5                  10                  15

His Gly

<210> SEQ ID NO 14
<211> LENGTH: 1288
<212> TYPE: DNA
<213> ORGANISM: Homo sapiens

<400> SEQUENCE: 14
ctaggtaaga gtttgttccc gtggtgcgga gggtcaaggc ccacacccgg aaacctagcg      60
aggtaaagtt gcgtcttggt tgtagagacg acaacttctc cgcttcctcg gcgatggcgg    120
cgtccgggag cggtatggcc cagaaaacct gggaactggc caacaacatg caggaagctc    180
agagtatcga tgaaatctac aaatacgaca agaaacagca gcaagaaatc ctggcggcga    240
agccctggac taaggatcac cattacttta gtactgcaa aatctcagca ttggctctgc     300
tgaagatggt gatgcatgcc agatcgggag gcaacttgga agtgatgggt ctgatgctag    360
gaaaggtgga tggtgaaacc atgatcatta tggacagttt tgctttgcct gtggagggca    420
ctgaaacccg agtaaatgct caggctgctg catatgaata catggctgca tacatagaaa    480
atgcaaaaca ggttggccgc cttgaaaatg caatcgggtg gtatcatagc caccctggct    540
```

| | | |
|---|---|---|
| atggctgctg gctttctggg attgatgtta gtactcagat gctcaatcag cagttccagg | 600 |
| aaccatttgt agcagtggtg attgatccaa caagaacaat atccgcaggg aaagtgaatc | 660 |
| ttggcgcctt taggacatac ccaaagggct acaaacctcc tgatgaagga ccttctgagt | 720 |
| accagactat tccacttaat aaaatagaag attttggtgt acactgcaaa caatattatg | 780 |
| ccttagaagt ctcatatttc aaatcctctt tggatcgcaa attgcttgag ctgttgtgga | 840 |
| ataaatactg ggtgaatacg ttgagttctt ctagcttgct tactaatgca gactatacca | 900 |
| ctggtcaggt cttttgatttg tctgaaaagt tagagcagtc agaagcccag ctgggacgag | 960 |
| ggagtttcat gttgggttta gaaacgcatg accgaaaatc agaagacaaa cttgccaaag | 1020 |
| ctacaagaga cagctgtaaa actaccatag aagctatcca tggattgatg tctcaggtta | 1080 |
| ttaaggataa actgtttaat caaattaaca tctcttaaac agtctctgag aagtacttta | 1140 |
| cctgaaagac agtatgagaa aaatattcaa gtaacacttt aaaaccagtt acccaaaatc | 1200 |
| tgattagaag tataaggtgc tctgaagtgt cctaaatatt aatatcctgt aataaagctc | 1260 |
| tttaaaatga aaaaaaaaaa aaaaaaaa | 1288 |

<210> SEQ ID NO 15
<211> LENGTH: 1288
<212> TYPE: DNA
<213> ORGANISM: Homo sapiens

<400> SEQUENCE: 15

| | | |
|---|---|---|
| gtaagagttt gttcccgtgg tgcggagggt caaggcccac acccggaaac ctagcgaggt | 60 |
| aaagttgcgt cttggttgta gagacgacaa cttctccgct tcctcggcga tggcggcgtc | 120 |
| cgggagcggt atggcccaga aacctgggga actggccaac aacatgcagg aagctcagag | 180 |
| tatcgatgaa atctacaaat acgacaagaa acagcagcaa gaaatcctgg cggcgaagcc | 240 |
| ctggactaag gatcaccatt actttaagta ctgcaaaatc tcagcattgg ctctgctgaa | 300 |
| gatggtgatg catgccagat cgggaggcaa cttggaagtg atgggtctga tgctaggaaa | 360 |
| ggtggatggt gaaaccatga tcattatgga cagttttgct ttgcctgtgg agggcactga | 420 |
| aacccgagta atgctcagg ctgctgcata tgaatacatg gctgcataca tagaaaatgc | 480 |
| aaaacaggtt ggccgccttg aaaatgcaat cgggtggtat catagccacc tggctatgg | 540 |
| ctgctggctt tctgggattg atgttagtac tcagatgctc aatcagcagt tccaggaacc | 600 |
| atttgtagca gtggtgattg atccaacaag aacaatatcc gcagggaaag tgaatcttgg | 660 |
| cgcctttagg acatacccaa agggctacaa acctcctgat gaaggacctt ctgagtacca | 720 |
| gactattcca cttaataaaa tagaagattt tggtgtacac tgcaaacaat attatgcctt | 780 |
| agaagtctca tatttcaaat cctctttgga tcgcaaattg cttgagctgt tgtggaataa | 840 |
| atactgggtg aatacgttga gttcttctag cttgcttact aatgcagact ataccactgg | 900 |
| tcaggtcttt gatttgtctg aaaagttaga gcagtcagaa gcccagctgg gacgagggag | 960 |
| tttcatgttg ggtttagaaa cgcatgaccg aaaatcagaa gacaaacttg ccaaagctac | 1020 |
| aagagacagc tgtaaaacta ccatagaagc tatccatgga ttgatgtctc aggttattaa | 1080 |
| ggataaactg tttaatcaaa ttaacatctc ttaaacagtc tctgagaagt actttacctg | 1140 |
| aaagacagta tgagaaaaat attcaagtaa cactttaaaa ccagttaccc aaaatctgat | 1200 |
| tagaagtata aggtgctctg aagtgtccta aatattaata tcctgtaata aagctcttta | 1260 |
| aaatgaaaaa aaaaaaaaaa aaaaaaaa | 1288 |

<210> SEQ ID NO 16
<211> LENGTH: 1309
<212> TYPE: DNA
<213> ORGANISM: Homo sapiens

<400> SEQUENCE: 16

| | | | | | |
|---|---|---|---|---|---|
| gtgtcatggc | tgccccaaga | gtctaggtaa | gagtttgttc | ccgtggtgcg | gagggtcaag | 60 |
| gcccacaccc | ggaaacctag | cgaggtaaag | ttgcgtcttg | gttgtagaga | cgacaacttc | 120 |
| tccgcttcct | cggcgatggc | ggcgtccggg | agcggtatgg | cccagaaaac | ctgggaactg | 180 |
| gccaacaaca | tgcaggaagc | tcagagtatc | gatgaaatct | acaaatacga | caagaaacag | 240 |
| cagcaagaaa | tcctggcggc | gaagccctgg | actaaggatc | accattactt | taagtactgc | 300 |
| aaaatctcag | cattggctct | gctgaagatg | gtgatgcatg | ccagatcggg | aggcaacttg | 360 |
| gaagtgatgg | gtctgatgct | aggaaaggtg | gatggtgaaa | ccatgatcat | tatggacagt | 420 |
| tttgctttgc | ctgtggaggg | cactgaaacc | cgagtaaatg | ctcaggctgc | tgcatatgaa | 480 |
| tacatggctg | catacataga | aaatgcaaaa | caggttggcc | gccttgaaaa | tgcaatcggg | 540 |
| tggtatcata | gccaccctgg | ctatggctgc | tggctttctg | ggattgatgt | tagtactcag | 600 |
| atgctcaatc | agcagttcca | ggaaccattt | gtagcagtgg | tgattgatcc | aacaagaaca | 660 |
| atatccgcag | ggaaagtgaa | tcttggcgcc | tttaggacat | acccaaaggg | ctacaaacct | 720 |
| cctgatgaag | gaccttctga | gtaccagact | attccactta | taaaataga | agattttggt | 780 |
| gtacactgca | acaatatta | tgccttagaa | gtctcatatt | tcaaatcctc | tttggatcgc | 840 |
| aaattgcttg | agctgttgtg | gaataaatac | tgggtaatca | cgttgagttc | ttctagcttg | 900 |
| cttactaatg | cagactatac | cactggtcag | gtctttgatt | tgtctgaaaa | gttagagcag | 960 |
| tcagaagccc | agctgggacg | agggagtttc | atgttgggtt | tagaaacgca | tgaccgaaaa | 1020 |
| tcagaagaca | aacttgccaa | agctacaaga | gacagctgta | aaactaccat | agaagctatc | 1080 |
| catggattga | tgtctcaggt | tattaaggat | aaactgttta | atcaaattaa | catctcttaa | 1140 |
| acagtctctg | agaagtactt | tacctgaaag | acagtatgag | aaaaatattc | aagtaacact | 1200 |
| ttaaaaccag | ttacccaaaa | tctgattaga | agtataaggt | gctctgaagt | gtcctaaata | 1260 |
| ttaatatcct | gtaataaagc | tctttaaaat | gaaaaaaaaa | aaaaaaaa | | 1309 |

<210> SEQ ID NO 17
<211> LENGTH: 873
<212> TYPE: DNA
<213> ORGANISM: Homo sapiens

<400> SEQUENCE: 17

| | | | | | |
|---|---|---|---|---|---|
| taataaaaaa | attaaacatt | gtattaactg | taggaagaaa | acaaaccagt | tacccagatt | 60 |
| aattacgctt | tgggaacaaa | tgcggttcac | aggagtgcca | aagatttaac | tgtaacctgt | 120 |
| tacgagaact | gagtactgga | cattttcaga | tcagtaatgg | cacattatat | atacgtagat | 180 |
| gttaactttt | aaccaagcgc | aaaaaagcaa | tcaaggagta | cccactgcct | cctcgcatcg | 240 |
| atagaaaaag | cccatctgca | agtgaagtgc | caagccacca | cgagcccgtt | atcttttacg | 300 |
| catgtacagt | gagtcatctt | gaagtaaacg | ggaatgccat | gtttatcttc | ctctcaacca | 360 |
| gcttccagaa | cgacttttag | ctcagttgta | caacagacag | ccttaccttt | tagtctttca | 420 |
| acaaacttat | ctccatttaag | gtacctatac | ccacacaaaa | acactttccg | ccctccacat | 480 |
| cccgctctta | aggctccagc | tacctttaat | atggcggagg | ccgagcctgc | gcattagaag | 540 |
| cagagaaggc | aaataccagt | ttctggaata | acgttacatg | cccttcttcc | ggttttccg | 600 |
| agacaagatg | ttctcatttta | agcaacaaga | agattcgtct | ctcgctatta | ctgtaactgc | 660 |

| | |
|---|---|
| tgtttatatc gtcatgtccc ggaaaggtcc ctgtcttccc tgaatggtct ctaccaactt | 720 |
| cacctccggt tctaggtgtc atggctgccc caagagtcta ggtaagagtt tgttcccgtg | 780 |
| gtgcggaggg tcaaggccca cacccggaaa cctagcgagg taaagttgcg tcttggttgt | 840 |
| agagacgaca acttctccgc ttcctcggcg tac | 873 |

<210> SEQ ID NO 18
<211> LENGTH: 3067
<212> TYPE: DNA
<213> ORGANISM: Homo sapiens

<400> SEQUENCE: 18

| | |
|---|---|
| gacggagcag gggggggcctg ccgttgggg agagaaggcg catgggaacc aaggaaccgc | 60 |
| tcgcccccgg gccctggagg tggctgacta ggaagcgtcg tcaggcaacc agctatcaac | 120 |
| aacaccgcgg gcagcagcga ccgcagtggc ccaggaatcc ggaccgtgta accagggaac | 180 |
| ctccccgacc ccggcagctg caagacccct gctcacagaa ctcccgcccc caaccctcat | 240 |
| aactcgtagt caccgatgcc ggcctcacgg cggcgaaatc ccaactctcc acacccttaa | 300 |
| ctcgggcacc tcccccaccg cacccagccg ccacgagacc cctgccgac aagaaacccc | 360 |
| accccccaccc ccagattcca gagcctgtaa ctctggcacg tcgccggcct agttgcctcg | 420 |
| agacctacgc cccgagggag ccactgcccc tgccccgct ccggggcagc gaatgcagcc | 480 |
| ccaggaccct ccaccctcaa cctacaccac cccaggccac acctcgccac tcacgctccc | 540 |
| catccgcggc tggctgactc ttactcaggg gagcgggctc cgtccggggg agacacacag | 600 |
| tgctctagag gatcgtcgcg gaccgaagag gttacagcgg ccacctggag cgggaacagc | 660 |
| atgacagacc tccgggccgg ggctccgccc ctcaggccca gccctccgct cgcccttcgc | 720 |
| caaccgccgg gtacggcccc gccccactg caggcggccg cgcggcaaga catcgccccc | 780 |
| tgctgtcctg gaggccgcat agctgccgc tgctctcggt tcgccagtac gctggccggg | 840 |
| gacttggtca actcgttctc ctgctgtgcc caggggctat aaactgtgg gggccacttc | 900 |
| tcaggctaaa tctattgcag cctctccagc ctcccatgca ccagccagct taggaacagt | 960 |
| gtaagagcct ggaaagaaaa atggggaggg gtggtagtga gaggaaaagt gttggcatac | 1020 |
| ctctcagggc attactccta gcccaggagt gtggtcaacg ttgggtcctg ggctttcatt | 1080 |
| accattttca acatattatt cagttcaccc caatacaatc gcatatggcc atatgctacc | 1140 |
| actagaaaag agacctctag tttcccagga gagtggaact aagggtaggt attaatgtac | 1200 |
| tattttaccc taaatttctt tgtaagatgg ttttaaagga aattttcttc aacgaaagt | 1260 |
| cagtgccaaa acagcaagct gtggtgtgga ttcaataatt ctaatgtttt tgtcttaact | 1320 |
| gattattaca acgcattgta acagttatag aagcacctac ggagacttac agacataatg | 1380 |
| gaaggaatgg taattggagc gtcaagaaag agttcgtggt cgatctcact ggactgcatt | 1440 |
| tttaaagatt aataggagtt cccaggcaga aaatttacga aagagcgttt caagcaatgc | 1500 |
| tgaccacata tgcaaagcca agtaaagat atctgcattg ctagaatgaa agtttcaag | 1560 |
| gggggactaa aaagagatga agctggaaga ggtgcatagg ggccaggttg ttaacagctg | 1620 |
| tggtgctatc ttttcttttt tcttcttttt tctttctttc tttctttttt tttttttttt | 1680 |
| ttttttttgag actggctctg tctaacaggc tggagtggcg caatctcgga tcactgcaac | 1740 |
| ttccgcctcc tgggttcaaa cgattctcct gcctcagcct catgagtagc cgggactaca | 1800 |
| ggcgcacatc atcacgcccg gctaattttt ttttgtatt ttttagtaga cgggggttt | 1860 |
| caccatgttg gccaggctgg tcttgaactc ccgacctcaa gtgatcagcc cgcctcggct | 1920 |

```
gcccaaagtg ctgggattac aggcgtgagc caccgcgcct ggcctgtcat gctatctttt    1980
caggaaataa aagaaaaaaa aatcttgaac acctatgcta ggtgctagga gataaaacaa    2040
ggaacgcaga cctgctccct gtgtcttgaa acttaaaatc ttgcacggat ggaagaatga    2100
gatggagaaa aagaaaacc taaaacacgt gaactaataa aaaaattaaa cattgtatta    2160
actgtaggaa gaaacaaac cagttaccca gattaattac gctttgggaa caaatgcggt    2220
tcacaggagt gccaaagatt taactgtaac ctgttacgag aactgagtac tggacatttt    2280
cagatcagta atggcacatt atatatacgt agatgttaac ttttaccaaa gcgcaaaaaa    2340
gcaatcaagg agtacccact gcctcctcgc atcgatagaa aaagcccatc tgcaagtgaa    2400
gtgccaagcc accacgagcc cgttagcttt tacgcatgta cagtgagtca tcttgaagta    2460
aacgggaatg ccatgtttat cttcctctca accagcttcc agaacgactt ttagctcagt    2520
tgtacaacag acagccttac cttttagtct ttcaacaaac ttatctcatt taaggtacct    2580 atcccacac aaaaacactt tccgccctcc acatcccgct cttaaggctc cagctacctt     2640
taatatggcg gaggccgagc ctgcgcatta gaagcagaga aggcaaatac cagtttctgg    2700
aataacgtta catgcccttc ttccggtgcg gaagactata ccactcccat accctataac    2760
tttgtttgtt ctatttcaca catataattt tccgagacaa gatgttctca tttaagcaac    2820
aagaagattc gtctctcgct attactgtaa ctgctgttta tatcgtcatg tcccggaaag    2880
gtccctgtct tccctgaatg gtctctacca acttcacctc cggttctagg tgtcatggct    2940
gccccaagag tctaggtaag agtttgttcc cgtggtgcgg agggtcaagg cccacacccg    3000
gaaacctagc gaggtaaagt tgcgtcttgg ttgtagagac gacaacttct ccgcttcctc    3060
ggcgtac                                                              3067
```

JAB1 AS A PROGNOSTIC MARKER AND A THERAPEUTIC TARGET FOR HUMAN CANCER

CROSS-REFERENCE TO RELATED APPLICATIONS

This application is a divisional of co-pending U.S. patent application Ser. No. 10/858,869 filed Jun. 1, 2004 now abandoned, which claims priority to U.S. Provisional Patent Application 60/474,048 filed May 29, 2003, all of which are incorporated by reference herein in their entirety.

STATEMENT REGARDING FEDERALLY SPONSORED RESEARCH OR DEVELOPMENT

This invention was made with U.S. Government support from the National Cancer Institute/National Institutes of Health Grant number 1RO1CA90853-01A1. The U.S. Government may have certain rights in this invention.

FIELD OF THE INVENTION

The present invention relates generally to methods of diagnosing, prognosticating and treating human cancers, as well as assaying for therapeutic agents for treating human cancers. More specifically, the invention regards JUN activation binding protein 1 (JAB1)-associated embodiments for cancer diagnosis and therapy, such as breast cancer.

BACKGROUND OF THE INVENTION

Cancer can be caused by a wide variety of genetic abnormalities, such as hereditary or non-hereditary mutations. However, many of the known genetic causes of cancer are caused by mutations in or overexpression of genes that belong to a class encoding proteins having similar functional characteristics. For example, cell cycle regulatory genes are a class of genes that have been found to be mutated or differentially expressed in some cancers.

Cell cycle regulatory genes include genes that encode for cyclins and cyclin-dependent kinases (CDKs). Different cyclins are expressed and degraded at different stages of the eukaryotic cell cycle. Cyclins are positive cell cycle regulators, as they bind and activate CDKs, which contribute to the progression of the cell cycle from one stage of the cell cycle to the next stage of the cell cycle. CDK inhibitors are negative cell cycle regulators that bind cyclin-CDK complexes and inhibit the activity of CDKs in the cyclin-CDK complexes.

One example of a CDK inhibitor gene is the p27 gene, which encodes p27 protein, also known as $p27^{Kip1}$. The p27 protein inhibits the activity of CDKs that are involved in the G1 to S phase transition of the cell cycle, contributing to G1 arrest of the cell cycle and prevention of unregulated, abnormal cell division.

While mutations in the p27 gene have not been found to date in human tumors, the level of p27 protein in many human tumors has been found to be below the level of p27 protein typically found in healthy human tissue. As the level of p27 protein in cells is regulated primarily at the post-transcriptional level, it is believed that factors that contribute to the degradation of p27 protein play a key role in regulating the level of p27 protein in cells.

HER-2 protein is a protein that is believed to be involved in the degradation of p27 protein. An inverse relationship between the amount of HER-2 protein and the amount of p27 protein has been found in primary breast tumor samples. Overexpression of HER-2 protein in a breast cancer cell line resulted in reduced levels of p27 protein in the cell line (Yang, et al., Journal of Biological Chemistry 275:24735-24739 (2000)).

Methods of using the HER-2 gene or protein in breast cancer diagnostics and therapeutic agents for breast cancer have been proposed (see, e.g., U.S. Pat. No. 6,251,601 and Herceptin® antibody, available from Genentech, San Francisco, Calif.). However, overexpression of HER-2 protein via gene amplification of the HER-2 gene has been found to date in only approximately 25% of breast cancer patients. Furthermore, one study has shown that less than half of the HER-2 overexpressing breast cancer patients in the study responded to HER-2 antibody-based treatment (Vogel, et al., Journal of Clinical Oncology 20: 719-726 (2002); Baselga J et al., Seminars in Oncology, Vol 26(4): Suppl. 12 pp 78-83, 1999; Slamon D. J., et al., The New England Journal of Medicine, Vol 344 pp 783-792, 2001; Vogel C. L et al., Journal of Clinical Oncology, Vol 20, pp 719-726, 2002).

In vitro studies of JAB1 protein (also referred to as CSN5 or $p38^{JAB1}$) demonstrate that JAB1 protein contributes to the degradation of p27 protein, as overexpression of JAB1 protein in cultured cell lines resulted in decreased levels of p27 protein in the cell lines (see, Tomoda, et al., Nature 398:160-165 (1999), and Tomoda, et al., Journal of Biological Chemistry 277:2302-2310 (2002)).

To date, JAB1 protein has been studied in several types of human cancer (see, Tsuchida, et al., Jpn J Cancer Res. 93:1000-6 (2002), and Shen, et al., International Journal of Oncology 17:749-754 (2000)). In one study, it was found that the amount of JAB1 protein was inversely related to the amount of p27 protein in tumors of ovarian carcinomas; however, no correlation was found between JAB1 protein overexpression and the histological characteristics of the tumors, such as the stage of the patients' cancer and the grade of the tumors (Sui, et al., Clinical Cancer Research 7:4130-4135 (2001)). Shen et al. (2000) describe high levels of p27 in neuroblastomas, particularly in differentiated tumors. Localization of subcellular JAB1 expression was determined to be in both the nucleus and cytoplasm of undifferentiated and differentiating tumors, whereas predominantly nuclear localization was identified in differentiated tumor cells.

In another study, no difference was found between JAB1 protein levels in human pituitary tumors, such as corticotroph tumors or other pituitary adenomas, compared to normal pituitary tissue; however, a small but significant increase in JAB1 protein was detected in pituitary carcinomas compared to normal pituitary tissue (Korbonits, et al., Journal of Clinical Endocrinology and Metabolism 87:2635-2649 (2002)). The same study also examined p27 protein levels in human pituitary tumors. Low p27 protein levels were found in corticotroph adenomas and pituitary carcinomas. The study concluded that the low p27 protein levels found in corticotroph adenomas were not caused by JAB1 overexpression, as JAB1 overexpression was not found in corticotroph adenomas. Thus, it appears that JAB1 protein levels are elevated in some tumors in certain tissues, but are not elevated in tumors in other tissues, and that low p27 protein levels in cancer cells are not always correlated with a high level of JAB1 protein expression.

Previous studies have found that low p27 protein levels in breast tumors are often correlated with a poor prognosis and survival rate (Catzavelos, et al. (1997) Nat. Med. 3:227-230, Porter, et al. (1997) Nat. Med. 3:222-225). However, the investigations described herein indicate that JAB1 protein expression is frequently found in breast tumor cells and that JAB1 protein expression is prognostic of a lower survival rate and a lower progression-free survival rate. As discussed above, embodiments described herein also indicate that JAB1 protein levels and p27 protein levels are often inversely related in breast carcinomas and in T-cell lymphoma.

EP0856582 describes an inhibitor of the transcription factor activator protein-1 and a DNA encoding same. In particular embodiments, the inhibitor is the exportin protein.

United States Patent Application Publications US 20020156012; US 20030166243; and US 20030153097 relate to the peptidase activity of the JAB subunit or JAM domain. Compositions comprising the JAM domain are disclosed therein, and in some embodiments they are utilized to screen for agents that affect the peptidase activity. These agents may be further utilized for rational drug design. In specific embodiments, a screen entails in part the contact of a target protein to a JAB subunit, and there is also provided amelioration of a pathological condition by modulating the activity and agents directed thereto.

United States Patent Application Publication US 20030148954 describes agents for modulating AP-1 mediated gene expression, such as those comprising an internalization moiety and a peptide from the intracellular domain of Notch-1 or an analog or peptidomimetic thereof.

There remains a need for biological markers that can be used as a basis for diagnosing and prognosticating different types of cancer, as well as a need for therapeutic agents for treating such cancers.

BRIEF SUMMARY OF THE INVENTION

The human JAB1 (Jun activation domain-binding protein 1) protein was originally identified as a binder of the c-Jun activation domain. JAB1 protein selectively binds and activates several members of the Jun family of proteins. Jun proteins heterodimerize with Fos proteins to form the transcription factor AP-1, the activity of which is believed to play a role in cellular transformation and invasion in cancer.

As noted above, JAB1, aside from being an AP-1-coactivator, is involved in degradation of the cyclin-dependent kinase inhibitor p27. The present inventors examined JAB1 and p27 protein expression in the exemplary invasive breast carcinomas, colon cancer, and pancreatic cancer, for example, and identified the association of this expression with clinical outcome. JAB1 was detected immunohistochemically in the vast majority of tumors, with breast carcinomas showing high JAB1 expression and reduced or absent p27 levels. Tumors with high p27 expression were rarely positive for JAB1. Furthermore, all tested patients with JAB1-negative tumors had no evidence of relapse or disease progression at a median follow-up of 70 months. Immunoblotting showed strong JAB1 expression in breast carcinoma samples but not in paired normal breast epithelial samples, and JAB1 upregulation paralleled HER2/neu overexpression. Targeted overexpression of JAB1 by regulated adenovirus in breast cancer cell lines also reduced p27 levels by accelerating its degradation. Thus, the JAB1/p27 ratio is a novel indicator of aggressive, high-grade tumor behavior, and control of JAB1 provides a novel target for cancer therapy.

Thus, aspects of the invention provide methods of detecting the expression of JAB1 protein and methods of altering the expression of JAB1 protein in human cells. Aspects of the invention also provide compositions that express JAB1 protein in cells or alter the endogenous expression of JAB1 protein in cells. In addition, aspects of the invention include methods for screening for agents that alter JAB1 expression.

In one particular aspect of the invention, the ratio of JAB1 to another gene product is utilized for diagnosis, prognosis, or therapeutic applications for cancer. The other gene product may be of any kind such that in conjunction with the assessment of JAB1 expression it can be indicative of particular presence of disease and/or particular stage of disease. In specific embodiments, the other gene product is one in which JAB1 indirectly or directly is associated with, such as, for example, in a complex with JAB1. In particular embodiments, the other gene product binds to JAB1, such as directly to JAB1. In a specific embodiment, the other gene product is considered a JAB1 target. Specific examples of other gene products include p27, c-Jun, p53, cyclin D1, or any gene product involved in the COP9 signalosome. In particular aspects of the invention, the binding of JAB1 to p27 is involved with the disparity of their expression levels, given that JAB1 causes the translocation of p27 from the nucleus to the cytoplasm, decreasing the amount of $p27^{Kip1}$ in the cell by accelerating its degradation (Tomoda et al., 1999). In additional aspects, JAB1 is also associated with subcellular transport of other targets.

Thus, as JAB1 protein is involved in the degradation of p27 protein, and p27 protein activity is important in protecting a cell from becoming cancerous, JAB1 protein expression levels and/or the ratio of JAB1 expression levels to p27 expression levels are useful for detecting certain types of cancer and for prognosticating the progression of certain cancers. In addition, altering the expression of JAB1 is useful in treating certain cancers.

In a specific aspect, the ratio of JAB1 to p27, which is provided for exemplary purposes given the variety of gene products that may be utilized in association with JAB1, is determined. The levels of JAB1 and p27 may be determined based on their respective chromosome amplification, RNA levels or polypeptide levels, for example. In particular embodiments, the expression levels of JAB1 and p27 are determined as polypeptide levels, and the respective levels are considered in association with one another, such as in the form of a ratio JAB1/p27. In particular aspects of the invention, a ratio comprising high levels of JAB1 to low levels of p27 is indicative of cancer, and in particular embodiments it is indicative of particular stages of cancer. In other embodiments, the ratio provides information regarding a predisposition to developing cancer and/or a predisposition to developing aggressive cancer, which may be considered metastatic or invasive cancer.

In specific embodiments, the term "high" refers to expression levels that are detectably higher (increased) in cancer tissue or tissue suspected to be cancerous compared to normal tissue, such as adjacent normal tissue (paired tissue). The term "low" refers to expression levels that are detectably lower in cancer tissue or tissue suspected to be cancerous compared to normal tissue, such as adjacent normal tissue (paired tissue). These terms may refer to JAB1 expression alone, p27 alone, or to the ratio of JAB1/p27, for example. The assessment of levels may be qualitative or quantitative. That is, an unknown sample compared to a known standard may be assessed as having positive or negative expression in relation to one another. Alternatively, a percentage of positive cells may be represented quantitatively, wherein, for example, numbers of cells are counted and scored for expression level. In a specific embodiment, the tissue or cells for comparison which are considered normal (non-cancerous) are obtained from or are derived from the individual for which the cancerous tissue is obtained.

In accordance with known statistical assessments (Kouvaraki et al., 2003), a labeling index may be employed that provides a continuous variable. In specific embodiments, the labeling index for JAB1 and p27 is utilized as being indicative of expression states. For example, a labeling index may be considered high if it is greater than 50%, and the labeling index may be considered low if it is lower than 50%. In other specific embodiments, expression of JAB1 being higher than that of p27 for a particular tissue is indicative of cancer and/or indicative of a particular stage of cancer, such as late stage. Thus, in specific aspects of the invention, the JAB1/p27 ratio is utilized as a marker for cancer. In other embodiments, the ratio of JAB1 expression in the nucleus compared to the JAB1 expression in the cytoplasm of a cell is determined. When the ratio is high (greater than about 1), the presence of cancer is identified.

In particular embodiments, JAB1 being at high levels and p27 being at low levels corresponds to a detection of cancer in at least one cell or tissue. In further embodiments, a high JAB1/p27 ratio corresponds to detecting particular stages of cancer. For example, a high JAB1/p27 ratio may be indicative of late stages of cancer, which may be further defined as aggressive cancer, invasive cancer, or metastatic cancer. For example, in the exemplary form of cancer being breast cancer, a high JAB1/p27 ratio may be indicative of stage II, stage III, or stage IV cancer, for example. The JAB1/p27 ratio may correlate with progression of cancer, such as there being a low ratio for normal or benign tissue, and there being a higher ratio for hyperplasias, increasing to the highest ratios for metastatic, invasive cancer. In further specific embodiments, the JAB1/p27 ratio is utilized for determining a cancer treatment regimen.

In other embodiments, there is a correlation between JAB1 localization in the nucleus with stage progression, such as the exemplary cancer being breast cancer. In specific embodiments, Stage I may be represented by a ratio of JAB1 nuclear vs. cytoplasmic staining at about 3.0; Stage II may be represented by a ratio of JAB1 nuclear vs. cytoplasmic staining at about 4.5; and Stage III may be represented by a ratio of JAB1 nuclear vs. cytoplasmic staining at about 5. Thus, by determining JAB1 levels and its subcellular localization (nuclear versus cytoplasmic, for example), there is an indicator of tumor progression.

In other aspects of the invention, the level and/or localization of expression of JAB1, including high nuclear localization levels, and/or the JAB1/p27 ratio is utilized as a means to monitor therapy for cancer associated with high levels of JAB1, including high nuclear localization levels, or high levels of the JAB1/p27 ratio, respectively. That is, the level or localization of expression or ratio may be determined prior to therapy, such as upon or following diagnosis, and this level is monitored during therapy to observe the efficacy of the treatment. If the level of JAB1 expression or JAB1/p27 ratio continues to be high following treatment, an alternative treatment may be employed.

In additional aspects of the invention, blocking the interaction between JAB1 and p27 provides a mechanism for therapy of cancer. In particular embodiments, inhibiting this interaction facilitates arrest of cells and stops tumor growth. An agent to block the interaction may be of any kind, such as, for example, a polynucleotide, such as an RNA, a polypeptide, a peptide, a small molecule, and so forth. For example, the agent may be an inhibitor or ligand that binds to a pocket on JAB1 that is responsible at least in part for binding to its respective target, such as p27.

RNA agents include antisense RNA, such as RNAi or siRNA, for example. Peptide inhibitors may be of any kind, but in specific embodiments, they comprise at least part of a binding region between JAB1 and a gene product to which it binds, such as p27. For example, the peptide inhibitor may comprise at least part of the JAB1 sequence that binds p27, or the peptide inhibitor may comprise at least part of the p27 sequence that binds JAB1. In particular embodiments, a peptide inhibitor or any polypeptide or peptide further comprises a protein transduction domain, such as, for example, HIV Tat (Schwarze et al., 1999) or synthetic derivatives thereof (Ho et al., 2001).

Screens for agents that inhibit the binding of JAB1 to its target, such as p27, may be of any suitable kind. Multiple screens may be used in succession to narrow a pool of candidate inhibitors. In specific aspects of the invention, an in vitro screen may include ELISA, such as to monitor by dye visualization the absence of binding of p27 to JAB1 in the presence of a potential inhibitor. An example of an in vivo screen is a cell-based assay, in which binding of JAB1 to p27 in the presence of potential inhibitors is visualized from within the cell, such as by fluorescence or X-ray. Another screen utilizes the p27 binding domain of JAB1 and/or the JAB1 binding domain of p27, for example, immobilized to a substrate such that when a potential inhibitor binds the immobilized domain, the binding is visualized, such as by presence or absence of color, fluorescence, or radioactivity, for example. Finally, another screen that may be utilized is a two-hybrid screen wherein the JAB1 binding domain of p27 or the p27 binding domain of JAB1 are used as bait to identify peptides or polypeptides that bind at least in part thereto.

In a particular aspect of the invention, there is a method of diagnosing cancer or determining a prognosis for cancer in an individual, comprising assessing the JAB1 level in a cell of the individual. In a particular aspect of the invention, there is a method of diagnosing cancer or determining a prognosis for cancer in an individual, comprising obtaining a sample from the individual; assessing the JAB1 level in the sample; and diagnosing or prognosticating cancer based on the assessment, wherein the cancer is breast cancer, non-Hodgkins lymphoma, Hodgkins lymphoma, colon cancer, prostate cancer, pancreatic cancer, or lung cancer. The breast cancer may be ductal carcinoma or lobular carcinoma.

In a specific embodiment, the cancer is HER2 positive. The assessing step may comprise comparing the JAB1 level in the sample from the individual to the JAB1 level in a non-cancerous sample, such as a non-cancerous standard, including a known standard. In specific embodiments, the non-cancerous sample may be obtained from the individual, such as from a distant region of the same tissue or from adjacent normal tissue, for example. In particular aspects of the invention, when the JAB1 expression level is higher in the sample from the individual compared to the JAB1 expression level in the non-cancerous sample, the sample from the individual comprises at least one cancerous cell, and the diagnosis may thus be considered positive for cancer.

In a particular aspect of the invention, the assessing step may be further defined as assessing the ratio of JAB1/p27 level in a sample from an individual. When the ratio of JAB1/p27 comprises high JAB1 expression and low p27 expression, the sample may be considered to comprise at least one cancerous cell. This may be further defined as when the ratio of JAB1/p27 expression is greater than 1, the sample comprises at least one cancerous cell. This may be further defined as when there is high JAB1 expression and low p27 expression compared to that identified in normal cells, preferably from the same or analogous tissue, the sample comprises at least one cancerous cell.

In a particular aspect of the invention, the assessing step may be further defined as assessing the subcellular localization of JAB1 in a sample from an individual, such as the nuclear localization. When the ratio of nuclearly localized JAB1 compared to cytoplasmically localized JAB1 is high, the sample may be considered to comprise at least one cancerous cell. This may be further defined as when the ratio of nuclearly localized JAB1 to cytoplasmically localized JAB1 is greater than at least 1, the sample comprises at least one cancerous cell. This may be further defined as when the ratio of nuclearly localized JAB1 to cytoplasmically localized JAB1 is greater than at least about 3, the sample comprises at least one cancerous cell and is at least in stage III, for breast cancer embodiments.

The assessing step may be further defined as assessing the ratio of JAB1 polypeptide/p27 polypeptide and/or assessing the ratio of JAB1 polynucleotide/p27 polynucleotide. Although any suitable means of assessing the levels of JAB1 and p27 may be employed, in specific embodiments the assessing comprises hybridization, western blotting, ELISA, immunohistology, polymerase chain reaction, or a combination thereof. The hybridization may include in situ hybridization, such as with radioactive or non-radioactive means, including by fluorescence. Polymerase chain reaction methods may include RT-PCR and/or real time PCR.

Samples to be obtained from individuals may be of any kind, so long as they provide information as to the level or localization of expression of JAB1 and/or p27, particularly for cancer diagnosis and prognosis. In specific embodiments, the sample comprises at least one cancer cell, and although the sample may be from any tissue, in specific embodiments the sample comprises a biopsy, nipple aspirate, blood, urine, saliva, or feces.

In particular aspects of the invention, the diagnosing or prognosticating step provides information of the stage of the cancer and also may facilitate determining a therapy based on the stage of the cancer. In specific aspects, when the JAB1 level is greater in the sample from the individual compared to a non-cancerous sample, the sample from the individual comprises advanced stage cancer, or when the ratio of JAB1/p27 comprises high JAB1 expression and low p27 expression, the sample comprises advanced stage cancer.

In specific embodiments, the diagnosing and prognosticating methods described herein further comprise the step of treating the cancer, although treatments provided herein may be administered to an individual with cancer following diagnosis and/or prognosis through another means. Treatment may comprise delivering a JAB1-inhibiting agent to the individual, such as by delivering the JAB1-inhibiting agent directly to the cancerous cell, and this delivery may comprise microinjection, electroporation, liposomal delivery, by catheter, or a combination thereof, although other suitable means may be utilized.

In a particular aspect of the invention, a JAB1-inhibiting agent comprises a polynucleotide, a polypeptide, a peptide, a small molecule, or a mixture thereof. In specific aspects, the polynucleotide comprises antisense JAB1 sequence, which may be further defined as being comprised on a vector, wherein the polynucleotide is operably linked to a promoter suitable for regulation of the polynucleotide in the cancerous cell. The vector may be a viral vector, such as an adenoviral vector, a retroviral vector, an adeno-associated viral vector, a lentiviral vector, or a herpesviral vector, or it may be a non-viral vector, such as a plasmid. In some embodiments, the therapeutic composition is encapsulated in a cell, and one or more of the cells are delivered to the individual, such as directly to the tumor.

In specific aspects of the invention, antisense JAB1 polynucleotides comprise a hairpin structure having a duplex portion and a loop portion, wherein the duplex portion is about 10 base pairs (bp) to about 50 bp in length or about 15 bp to about 33 bp in length. Particular antisense JAB1 polynucleotides may comprise RNAi or siRNA compositions.

In additional aspects of the invention, there is a method for identifying the stage of a cancer in an individual, comprising obtaining a cancerous sample from the individual; assessing the ratio of JAB1/p27 level in the sample; and determining the stage of the cancer based on the assessment. In a specific embodiment, when the ratio of JAB1/p27 is high, the stage of the cancer is late stage.

In further aspects of the invention, there is a method for monitoring treatment of a cancer for an individual, wherein the cancer is characterized by a high JAB1/p27 ratio, comprising determining the JAB1/p27 ratio in a cancerous sample from a tissue from the individual prior to the treatment; administering the treatment to the individual; and determining the JAB1/p27 ratio in a sample from the tissue from individual subsequent to the treatment. The treatment may comprise delivering a JAB1-inhibiting agent to the individual. When the determination of the JAB1/p27 ratio in a sample from the individual subsequent to the treatment is lower than the JAB1/p27 ratio in the cancerous sample from the individual prior to the treatment, the treatment may be efficacious for the cancer.

In another aspect of the invention, there is a method of screening for a JAB1-inhibiting agent, comprising providing a JAB1 polypeptide; providing a p27 polypeptide; and providing a test compound, wherein when the test compound inhibits binding of the JAB1 polypeptide to the p27 polypeptide, the test compound is the JAB1-inhibiting agent. The method may further comprise the step of delivering the JAB1-inhibiting agent to an individual having cancer. The method may occur in vitro or in vivo. The providing of the JAB1 polypeptide may be further defined as providing a polynucleotide that encodes the JAB1 polypeptide, and the providing of the p27 polypeptide may be further defined as providing a polynucleotide that encodes the p27 polypeptide. Binding of the JAB1 polypeptide to the p27 polypeptide may be detected by any suitable means, although in particular aspects the detection comprises color detection, radioactivity detection, or fluorescence detection.

In specific embodiments, particular JAB1 regions are utilized in a screen. For example, agents that bind to the p27-binding domain (SEQ ID NO:13 or SEQ ID NO:11) of JAB1 are identified and utilized as inhibitors of JAB1 binding to p27. Agents that bind the c-Jun-binding domain (SEQ ID NO:12) may similarly be employed to inhibit JAB1 binding to c-Jun.

In an additional aspect of the invention, there is a kit, housed in a suitable container, comprising reagents to detect JAB1 or p27 localization or levels and/or comprising one or more JAB1-inhibiting agents identified by any suitable method, such as those exemplary methods described herein.

In another aspect of the invention, there is a composition comprising a JAB1-inhibiting agent, which may be, for example, a polynucleotide, polypeptide, peptide, small molecule, or mixture thereof. In specific embodiments, the peptide comprises SEQ ID NO:11, SEQ ID NO:12, or SEQ ID NO:13. The composition may be comprised in a pharmaceutically acceptable diluent. The composition may comprise antisense JAB sequence, or the composition may comprise at least part of a p27-binding domain of JAB1 or a c-Jun-binding domain of JAB1.

In an additional aspect of the invention, there is a method of enhancing therapy for cancer in an individual, comprising delivering to the individual a JAB1-inhibiting agent. In specific embodiments, the cancer comprises breast cancer. In additional specific embodiments, the therapy comprises a humanized antibody to the receptor HER2. The JAB1-inhibiting agent comprises a JAB1 antisense polynucleotide, in some embodiments, and in particular embodiments the JAB1 antisense polynucleotide comprises a viral vector having JAB1 siRNA, such as an adenoviral vector. In other embodiments, the JAB1-inhibiting agent comprises activity that inhibits binding of JAB1 to p27.

In specific aspects of the invention, there is a method of diagnosing cancer in an individual comprising obtaining a sample from the individual; measuring a level of JAB1 expression in the sample; and diagnosing the likelihood of cancer occurrence. The method may further comprise comparing the level of JAB1 expression in the sample to a pre-determined standard level of JAB1 expression. The method may also further comprise comparing the level of JAB1 expression in the sample to a second sample taken from another tissue from the individual. In specific embodiments, the measuring step is performed by dot blotting, Southern blotting, western blotting, ELISA, immunohistology, sandwich blotting, immunohistochemistry, polymerase chain reaction, RT-PCR, or non-radioactive in situ hybridization (NISH), for example. The method may also further comprise the steps of measuring a level of p27 in the sample; and determining a ratio of the level of JAB1 expression in the sample to the level of p27 expression in the sample. In particular embodiments, the method further comprises comparing the ratio of the level of JAB1 expression in the sample to the level of p27 expression in the sample to a pre-determined standard ratio of the level of JAB1 expression in the sample to the level of p27 expression.

In an additional aspect of the invention, there is a method for determining whether disease, such as breast cancer or non-Hodgkins lymphoma, is progressing in an individual, comprising obtaining a first sample from the individual at t=1; measuring a level of JAB1 expression in the first sample; obtaining a second sample from the individual at t=2, where t=2 is later than t=1; measuring a level of JAB1 expression in the second sample; and comparing the level of JAB1 expression in the first sample to the level of JAB1 expression in the second sample, wherein if the level of JAB1 expression in the first sample is higher than or the same as level of JAB1 expression in the second sample, disease is not progressing; and wherein if the level of JAB1 expression in the first sample is lower than level of JAB1 expression in the second sample, disease is progressing. Measuring steps may be performed by dot blotting, Southern blotting, western blotting, ELISA, immunohistology, or sandwich blotting.

In another aspect, there is a method of determining efficacy of treatment in an individual with a disease comprising obtaining a first sample from the individual at t=1; measuring a level of JAB1 expression in the first sample; treating the individual with a treatment at t=2, wherein t=2 is later than t=1; obtaining a second sample from the individual at t=3, where t=3 is later than t=2; measuring a level of JAB1 expression in the second sample; and comparing the level of JAB1 expression in the first sample to the level of JAB1 expression in the second sample, wherein if the level of JAB1 expression in the first sample is higher than or the same as level of JAB1 expression in the second sample, the treatment is efficacious; and wherein if the level of JAB1 expression in the first sample is lower than level of JAB1 expression in the second sample, the treatment is not efficacious. The measuring steps are performed by dot blotting, Southern blotting, western blotting, ELISA, immunohistology, or sandwich blotting.

In an additional aspect of the invention, there is an assay for selecting treatments effective for inhibiting a level of JAB1 expression in a cell, comprising constructing a JAB1 expression vector; transforming the cell with the JAB1 expression vector; measuring a level of JAB1 expression in the cell at t=1; treating the cell with a treatment at t=2, wherein t=2 is later than t=1; measuring a level of JAB1 expression in the cell at t=3, where t=3 is later than t=2; and comparing the level of JAB1 expression in the cell at t=1 to the level of JAB1 expression in the cell at t=3, wherein if the level of JAB1 expression in the cell at t=1 is higher than or the same as level of JAB1 expression in the cell at t=3, the treatment is efficacious; and wherein if the level of JAB1 expression in the cell at t=1 is lower than level of JAB1 expression in the cell at t=3, the treatment is not efficacious. The measuring steps are performed by dot blotting, Southern blotting, western blotting, ELISA, immunohistology, or sandwich blotting. In a specific embodiment, the cell is selected from normal human tissue or cancerous tissue.

In an additional aspect of the invention, there is a method for treating cancer in an individual comprising treating the individual with an efficacious treatment identified using the methods described herein. In another aspect of the invention, there is a method for treating a proliferative disease in an individual comprising inhibiting the expression of JAB1 in a cell, such as a proliferating cell, in the individual. The inhibition of the expression of JAB1 in the cell may be accomplished by treating the proliferating cells with an antisense agent complementary to a JAB1 gene.

In a specific embodiment, an antisense agent is complementary to at least part of GenBank Accession No. NM_006837 (SEQ ID NO:9), for example, which can be obtained at the World Wide Web site of the National Center for Biotechnology Information. Other exemplary sequences include GenBank Accession Nos.: U65928 (SEQ ID NO:8); BC001859; (SEQ ID NO:14); BC007272 (SEQ ID NO:15); and BC001187 (SEQ ID NO:16). In a specific embodiment, the treating step is accomplished by delivering the antisense agent to the proliferating cells by direct transformation of the proliferating cells with the antisense agent, or microinjection, electroporation, or liposomal delivery of the antisense agent. The inhibition of expression of JAB1 in the proliferating cells may be accomplished by treating the cancer cells with an RNAi agent complementary to a JAB1 polynucleotide. In a specific embodiment, the RNAi agent is delivered directly to the proliferating cells. The RNAi agent may be chemically modified to increase a half-life and stability of the RNAi agent in the proliferating cells. The RNAi agent may be delivered to the proliferating cells by direct transformation of the proliferating cells with the RNAi agent, or by microinjection, electroporation, by catheter or liposomal delivery of the RNAi agent.

In specific embodiments, an RNAi agent is expressed in the proliferating cells, such as from a viral vector or a non-viral vector. Particular viral vectors include, for example, adenoviral vectors, retroviral vectors, adeno-associated viral vectors, lentiviral vectors, or herpesviral vectors. Particular non-viral vectors include plasmids. The vector preferably comprises a promoter operably linked to a sequence to be transcribed, such as the siRNA, and the promoter is preferably suitable for expression in a mammalian cell. However, the promoter may be an RNA polymerase I, RNA polymerase II, or RNA polymerase III promoter. In specific embodiments, the promoter for the vector is tissue-specific, such as specific for the tissue type of cancer cell being treated. For example, when treating breast cancer, a tissue-specific breast cancer promoter may be employed. Examples of breast cancer-specific promoters include human alpha-lactalbumin (ALA) or ovine beta-lactoglobulin (BLG) promoters, for example. In particular, the promoter may be a U6 promoter, H1 promoter, 7SL promoter, human Y promoter, human MRP-7-2 promoter, Adenovirus VA1 promoter, human tRNA promoter, 5S ribosomal RNA promoter, or a functional hybrid or a combination of any of these promoters, for example. In specific embodiments, the viral vector comprises a terminator.

In specific embodiments of the invention, an RNAi agent is transcribed as a hairpin structure with a duplex portion and a loop portion. The duplex portion of the hairpin structure may be 10 to 50 bp in length. The duplex portion of the hairpin structure may be 15 to 33 bp in length. In embodiments wherein the proliferative disease is cancer, the cancer may be breast cancer, such as ductal carcinoma or lobular carcinoma, or it may be lymphoma, such as, for example, non-Hodgkins lymphoma.

In one embodiment, siRNAs and antisense constructs that reduce the expression of JAB1 protein in human cells are provided. The siRNAs and antisense constructs may be used in methods of treating human cancers. In another embodiment, a recombinant adenovirus that expresses JAB1 protein is provided.

In a further embodiment, JAB1 protein is detected and/or quantitated in human tissue samples in order to diagnose and/or prognosticate the development of human cancers. In one aspect, the detection or quantitation of JAB1 protein is used in methods of diagnosing cancer, prognosticating a cancer survival rate, and/or prognosticating the development of cancer. In specific embodiments, the cancer can be any cancer, such as breast cancer, non-Hodgkins lymphoma, colon cancer, prostate cancer, pancreatic cancer, or lung cancer, for example.

In specific embodiments the present invention encompasses any type of cancer, such as solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, Merkel cell, mucinous, non-small cell lung, oat cell, papillary, scirrhous, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), hystiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, cranio-pharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pheochromocytoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia, and other cells that have become immortalized or transformed. In specific embodiments, however, the present invention is directed to methods and compositions concerning breast, lymphoma, colon, prostate, pancreatic, and lung cancer.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIGS. 1A and 1B demonstrate survival rates JAB1-negative breast tumors vs. JAB1-positive breast tumors. FIG. 1A is a graph showing the progression-free survival (PFS) rates of breast cancer patients having JAB1-positive breast tumors or JAB1-negative breast tumors. FIG. 1B is a graph showing the overall survival (OS) rates of breast cancer patients having JAB1-positive breast tumors or JAB1-negative breast tumors.

FIGS. 3A and 3B show a western blot of four breast cancer cell lines transfected with Ad-JAB1-Myc and a chart showing the PhosphorImager quantitation of the proteins detected on the western blot, respectively.

FIG. 4A shows immunoblot analysis of cell lysates from parental NIH-3T3 cells and stable NIH-3T3 clones expressing Myc-JAB1 (Clones, #C1-4) showing various levels of exogenous Myc-JAB1 levels (Top panel). Myc-JAB1 expression corresponds to a decreased level of p27 in the stable clones but not in the control parental cells (Bottom panel). FIG. 4B shows the stable expression of Myc-JAB1 in 3T3 cells increased cellular proliferation as measured by [$^3$H]-thymidine incorporation. The increase in thymidine incorporation was directly proportional to the expression of exogenous Myc-JAB1 in the various stable clones. For thymidine incorporation, $1\times10^5$ cells of each JAB1-Myc clones and parental 3T3 cells were plated in six wells of a 24-well plate. After 24 h, the media was changed to serum-free DMEM medium and incubated at 37° C. for 24 h. The media was aspirated and replaced with DMEM with Serum, containing 1 mCiml $^3$H-thymidine (Amersham Biosciences, Piscataway, N.J., USA) and incubated at 37° C. for 1 h. Cells were washed twice with PBS and solubilized in 200 mM NaOH. Counts per minute were determined in a Liquid Scintillation Beta Analyzer (Packard Instruments Co., Meridan, Conn., USA). FIG. 4C shows morphology of parental NIH-3T3 cells and NIH-3T3-JAB1#C4. The Stable clone 3T3-JAB1#C4, expressing high levels of Myc-JAB1 exhibited morphologic transformation compared to control cells. They were spindle-shaped and display highly refractile morphology, with long protrusions and pseudopodia. A representative clonal population of cells photographed under phase-contrast microscopy is shown, with the inbox showing a single cell. FIG. 4D shows that exogenous JAB1 expression promotes S-phase progression as measured by Bromodeoxyuridine (BrdU) incorporation and propidium idodide (PI) staining. The parental cells and stable clones were serum starved for 24 hours and then replaced with DMEM with serum and labeled with Brdu for 45 minutes. The cells were then stained with fluorescent anti-Brdu antibodies and PI for Flow-cytometry analysis. FIG. 4E shows that JAB1 promotes growth in soft-agar. Stable clones #C3 and C4 along were parental control cells were plated in soft agar. After 1 week and 2 weeks plates were stained with crystal violet and foci formation were counted, and an average is shown. Summary of tumorigenesis assay (F) is shown. FIG. 4F shows that exogenous JAB1 expression induced tumorigenesis in nude mice. Stable clones, #C3, C4 and control cells (NIH-3T3) were injected s.c ($6\times10^6$ cells) into 6-week old female nude mice (BALB/C). Five mice were used for each cell line. After 35 days mice developed tumors>10 mm only with clones C3 and C4 but not with control injected clone. Pictures of each mice are shown at 35 and 42 days post-injection. FIG. 4G shows JAB1 expression promotes tumor development in nude mice. Mice were injected as in FIG. 4F, and tumor formation was scored weekly. In FIG. 4H, there is JAB1 and p27 immunostaining in mouse normal and tumor tissues. Mice-bearing JAB1 tumors (in FIG. 4F) were isolated and paraffin-embedded tissue sections obtained and stained with monoclonal antibodies for JAB1 or p27 and counterstained with hematoxylin. Representative tissue sections of the immunohistochemical analysis show low JAB1 expression and high p27 expression in normal tissue while the inverse was seen in tumor tissues. In FIG. 4I, there is a column chart representing the immunostaining above, indicating the relationship between JAB1 and p27 positive staining in normal and tissue samples. Three hundred positive and negative cells were counted in each of three fields for JAB1 and p27 in normal and four tumor tissue samples; the percent positive staining is shown.

In FIG. 6A, there is immunohistochemical staining of a breast tumor progression array for JAB1 and p27. JAB1 levels are low in normal tissue and increase with tumorigenesis. In FIG. 6B, the percent of cells staining positive for either JAB1 or p27 were quantified and graphed.

FIG. 10 shows the sequence of an exemplary double stranded siRNA (including the exemplary SEQ ID NO:3 and SEQ ID NO:4) used in a specific embodiment.

In FIG. 11A, expression of antisense JAB1 increased the endogenous level of p27. HeLa cells were transfected with a tetracycline-inducible (Tet-Off system) antisense JAB1. Cell lysates were immunoblotted with JAB1 and p27 antibodies Quantification of the immunoblots is shown on the right. In FIG. 11B, there is depletion of JAB1 by siRNA oligos in HeLa cells. Cells were transfected with siRNA targeting JAB1 (JAB1 siRNA) or a scrambled sequence (Control siRNA). Forty-eight hours after transfection, cell lysates were prepared and were subjected to western blotting analysis using anti-JAB1, anti-p27, anti.Cyclin A, anti-pRb and anti-actin antibodies. For kinase assay (last panel), Cyclin A was immunoprecipitated from cell lysates and analyzed for cyclinA/Cdk2-associated activity using Histone 1B as a substrate. In FIG. 11C, knockdown of endogenous JAB1 expression decreases the S-phase progression in cell cycle and increases 5 G1 cells. Hela cells transfected with JAB1 siRNA and Control siRNA. Progression through S-phase was measured with anti-Brdu fluorescent antibodies and propidium idodide (PI) staining for Flow cytometery analysis.

In FIG. 12A, there is a schematic of pSIREN Adeno strategy (Adeno-X viral DNA, BD-Pharmingen). In FIG. 12B, inhibition of endogenous JAB1 with Ad-JAB1siRNA but not with control Ad-LUCsiRNA, increases p27 expression levels. HeLa cells were transduced (MOI 50) with either Luciferase-RNAi pSIREN Shuttle vector or JAB1-RNAi pSIREN Shuttle vector. Cells were harvested 48 hours post-transfection and analyzed by western blotting analysis using both anti-JAB1 and anti-p27 antibodies.

In FIG. 13A, MDA-MB 231 cells were transduced with adenoviruses driven JAB1 siRNA, or Luciferase siRNA as a control, at MOI 50. Forty eight hours after, protein lysates were prepared and immunoblotted with an anti-JAB1, anti-p27 and anti-Cyclin A antibodies. Anti-β actin was used as a loading control. SiRNA ablation of JAB1 increases the steady-state level of p27Kip1 protein and decreased cyclin A levels. In FIG. 13B, siRNA ablation of JAB1 induces G1 arrest. Cells were treated same as in FIG. 13A, and cell cycle profile was determined by propidium iodine staining and FACS.

FIG. 14 demonstrates that siRNA ablation of JAB1 causes p27kip1 accumulation and prevents S-phase re-entry in Karpas 299 T-cells lymphoma. In FIG. 14A, knockdown of JAB1 protein levels by siRNA increases the steady-state level of p27 protein, decreases cyclin A and phopho-Rb levels. Karpas 299 cells were transfected with p-Siren JAB1 siRNA or luciferase siRNA as a control (5 µg each). Lysates were immunoblotted 48 h after with the indicated antibodies. In FIG. 14B, siRNA ablation prevents S-phase re-entry. Karpas 299 cells were treated as in FIG. 14A, and progression through S-phase was measured with anti-BrdU fluorescent antibodies and FACS 48 hr after. Forty-six % of control siRNA-treated cells were in S-phase compared to 15% with siRNA JAB1.

In FIG. 17A, there is a schematic representation of JAB1 full length (FL) and JAB1 N-terminal and JAB1 C-terminal sequential deletion constructs (ΔN and ΔC, respectively). Mapping of both JAB1-c-jun and JAB1-p27 interacting domains is depicted. The table summarizes the results of the below in vitro binding assays of various JAB1 recombinant protein to GST-c-Jun and GST-p27. In FIG. 17B, there is in vitro expression analysis of JAB1 full length and C- and N-terminal deletion deletions mutants. Using TnT coupled reticulocyte lysate system (Promega) full length and deletion mutants were in vitro translated and [$^{35}$S]-Methionine labelled. Ten percent of labeled products (input) were separated on SDS-PAGE. Gel was then fixed (in 50% methanol, 10% acetic acid), and dried. An autoradiography is shown. In FIG. 19C, for in vitro binding assay recombinant JAB1 and JAB1 deletion mutants prepared as in FIG. 17B were incubated with either Glutathione-S-transferase (GST) alone or GST-p27 fusion protein that was immobilized on glutathione agarose. The results of the binding assay show all N-terminal but not C-terminal deletion mutants of JAB1 binding to p27, indicating p27 binds to JAB1 (299-334 amino acids). In FIG. 17D, there is deletion analysis of JAB1-c-Jun interaction domain. Methods are the same as in FIG. 17C with recombinant JAB1 and JAB1 deletion mutants incubated with either Glutathione-S-transferase (GST) alone or GST-c-Jun (1-79 amino acids) fusion protein that was immobilized on glutathione agarose. JAB1 interaction domain on c-Jun was mapped to 1-67 amino acids (Claret et al, Nature, 1996). The results of the binding assay show all C-terminal but not N-terminal deletion mutants of JAB1 bind to c-Jun, indicating c-Jun binds to JAB1 at its N-terminus between 49-96 amino acids of JAB1.

In FIG. 20A, 1, 2 and 3 kb upstream of the mRNA start site have been amplified by PCR, and the JAB1 promoter regions were predicted by using Proscan V1.7. Primers were designed to amplify 1, 2, and 3 kb upstream of the ATG. In FIG. 20B, PCR amplification products of the predicted regions are identified on the agarose gel. In FIG. 20C, there is the transcriptional start site of the Jab1 gene.

FIG. 21 provides the JAB1 promoter sequence and the corresponding transcription factor binding sites, as well as the transcription start site at +1 (SEQ ID NO:17).

DETAILED DESCRIPTION OF THE INVENTION

I. The Present Invention

Figure 1:
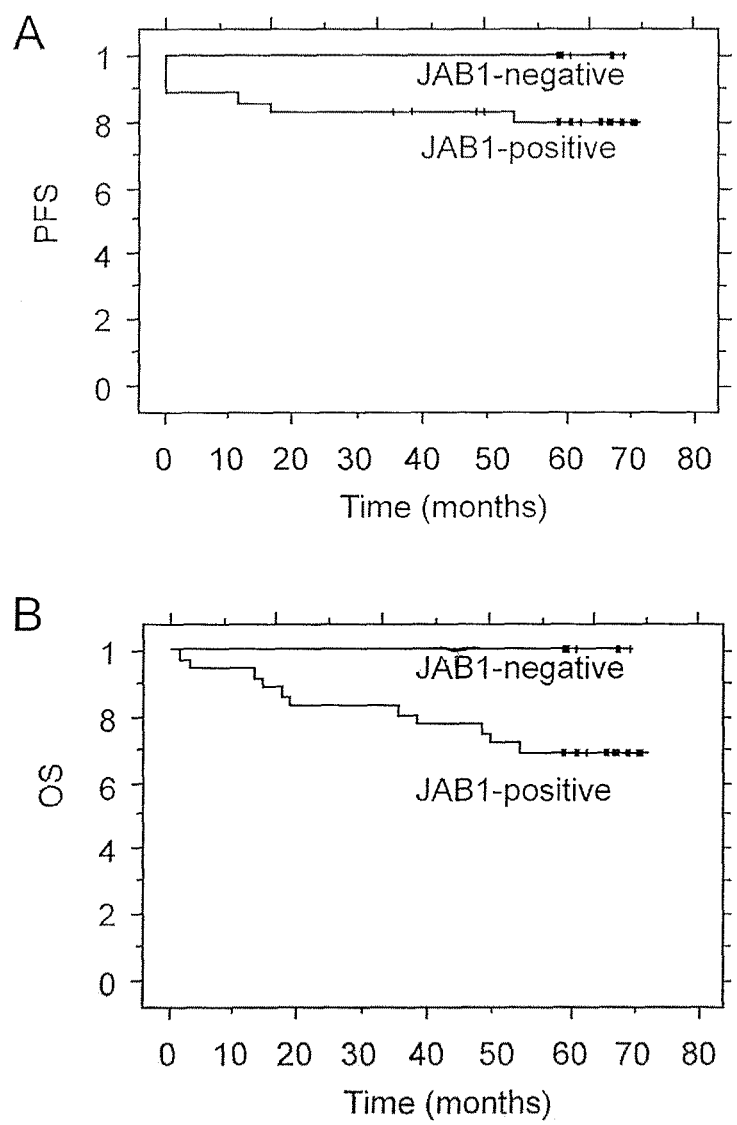

In keeping with long-standing patent law convention, the words "a" and "an" when used in the present specification in concert with the word comprising, including the claims, denote "one or more."

The practice of the present invention will employ, unless otherwise indicated, conventional techniques of molecular biology, microbiology, recombinant DNA, and so forth which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOL- OGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

In view of the unpredictable expression and significance of JAB1 protein in human cancers, the expression of JAB1 protein in several types of cancer, including breast cancer, non-Hodgkins lymphoma, colon cancer, pancreatic cancer, and others was studied. The present invention provides methods of diagnosing and prognosticating the development of human cancer, as well as methods for reducing the expression or altering the subcellular localization of JAB1 protein in cells to treat certain cancers. The present invention also provides assays that may be employed to screen for compounds that affect JAB1 expression.

In particular aspects of the invention, the level of JAB1 expression is diagnostic for cancer. When the level of JAB1 is high in a sample suspected of comprising at least one cancer cell compared to the level in a normal cell from the same or similar tissue, this is indicative of cancer. In particular, the ratio of JAB1 level to the level of one of its targets may be indicative of cancer. Although a variety of targets may provide diagnostic molecular indicia in conjunction with JAB1, such as c-Jun, p53, and cyclin D1, in specific and illustrative embodiments the ratio of JAB1 to p27 is utilized. A skilled artisan recognizes that although in specific embodiments there are p27-associated embodiments described herein, these methods and reagents also apply to any suitable target that provides diagnostic and/or prognostic cancer information, but for the sake of brevity only the present inventors herein focus on p27 aspects.

To facilitate the diagnosis and/or prognosis of cancer, there are provided herein methods of identifying the stage of a cancer in an individual, such as by determining the level and/or subcellular localization of JAB1 and/or the ratio of JAB1/p27 in a sample from the individual. When the level and/or nuclear localization of JAB1 and/or the ratio of JAB1/p27 is high in the sample, the stage of the cancer is thus determined. In specific aspects, when the level of JAB1 and/or the ratio of JAB1/p27 is high, the stage of the cancer is a late stage or advanced stage, such as being metastatic or invasive cancer.

In particular embodiments, cancer treatments may be monitored via assessment of JAB1 localization and/or levels, such as assessment of JAB1/p27 ratio levels. The level and/or localization of JAB1 or its ratio to p27 is determined prior to treatment, a treatment is delivered to the individual, and thereafter the level and/or localization of JAB1 or its ratio to p27 is determined. The treatment may or may not target JAB1, although in particular embodiments the treatment modulates JAB1 expression, such as by decreasing it. If the level of JAB1 expression or its ratio to p27 is reduced following the treatment, the cancer treatment may be considered efficacious.

Treatments that target JAB1 are employed herein. The treatment may comprise reducing the expression level or localization of JAB1 itself or it may comprise inhibiting the binding of JAB1 to p27, or a combination of the treatments may be used. In specific embodiments, JAB1 expression is reduced by employing antisense JAB1 sequence to target the JAB1 transcripts. Treatments may also comprise inhibiting the binding of JAB1 to p27, such as by delivering agents that inhibit the binding of JAB1 to its target, p27. These may be polypeptides, peptides, or small molecules, for example. JAB1-inhibiting agents may directly or indirectly affect the binding of JAB1 to its target, but in specific embodiments the agents interfere physically with the binding of JAB1 to its target domain on p27. Specifically, an agent may bind JAB1 and inhibit its binding to p27, or the agent may bind p27 and inhibit its binding to JAB1.

In vitro and in vivo screens to identify JAB1-inhibiting agents are described herein. In specific embodiments, the screens employ providing JAB1 and p27 polypeptides, and the interference of their respective binding to each other is assayed in the presence of a test compound. When the binding is inhibited, the test compound is useful as a JAB1-inhibiting agent and may be utilized in cancer treatment methods. Assessment of the binding of JAB1 and p27 may be by any suitable means, although in specific embodiments colorimetric, radioactive, or fluorescent methods are utilized.

Kits for the diagnosis, prognosis, and/or treatment of cancer are provided herein, particularly those reagents suitable for detection of JAB1 and p27 levels and/or those kits comprising JAB1-inhibiting agents suitable for cancer treatment.

II. Diagnostic Uses

JAB1 nucleic acid, antibody, and/or polypeptide compositions may be used to analyze patient samples for a level of JAB1 and/or p27 expression associated with a disease state or predisposition to a disease state. In a first step, patient sample is obtained. Samples, as used herein, include biological fluids such as semen, blood, cerebrospinal fluid, tears, saliva, lymph, dialysis fluid and the like; organ or tissue-derived fluids; or derivatives and fractions of such fluids. The cells may be dissociated, in the case of solid tissues, or tissue sections may be analyzed. Once patient samples are obtained, the level or localization of JAB1 expression in the sample is assessed. Optionally, the level of expression of a target, such as p27, is assessed. Assessing JAB1 and/or p27 expression can be performed in various ways well known in the art. For example, the level of JAB1 expression may be determined by assaying the amount of JAB1 mRNA present in a patient sample by Southern blotting, dot blots, or other such techniques (see, e.g., Maniatis, Fritsch & Sambrook, Molecular Cloning: A Laboratory Manual (1982 and recent editions)).

Alternatively, levels of expression for JAB1 in patient samples can be determined by assaying the amount of JAB1 protein present in the patient samples, such as wherein antibodies specific for JAB1 are used for detecting the JAB1 protein and/or respective antibodies are utilized for p27. Assays used to detect levels of JAB1 protein in a sample derived from a host are well-known to those of skill in the art and include western blot analysis, ELISA assays, "sandwich" assays and radioimmunoassays (see, e.g., Coligan et al., Current Protocols in Immunology 1(2), Chapter 6, (1991)), for example. Generally, western blotting is a technique for blotting proteins onto nitrocellulose, nylon or other transfer membrane after the proteins have been resolved by gel electrophoresis. The proteins can be detected by one of several methods, including autoradiography (if labeled), or through binding to labeled, $^{125}$I-labeled or enzyme-linked antibodies, lectin or other specific binding agents, for example.

An ELISA assay may be employed, which initially comprises preparing an antibody specific to the JAB1 antigen, preferably a monoclonal antibody. Next, a reporter antibody typically is prepared against the monoclonal antibody. To the reporter antibody is attached a detectable reagent such as a radioactive moiety, fluorescent moiety or horseradish peroxidase enzyme, for example. A sample is removed from the host and incubated on a solid support, e.g., a polystyrene dish, binding the proteins in the sample. Any free protein binding sites on the dish are then blocked by incubating with a non-specific protein, such as bovine serum albumen or milk proteins. Next, the monoclonal antibody is incubated in the dish during which time the monoclonal antibodies attach to any JAB1 proteins from the sample attached to the polystyrene dish. Unbound monoclonal antibody is washed out with buffer. The reporter antibody is then placed in the dish resulting in binding of the reporter antibody to any monoclonal antibody bound to JAB1. Unattached reporter antibody is then washed out, JAB1 protein is then detected and the amount of JAB1 protein present in a given volume of patient sample is compared against a standard curve.

A "sandwich" assay is similar to an ELISA assay and may also be used in the invention. In a "sandwich" assay, JAB1 is passed over a solid support and allowed to bind to antibody attached to the solid support. A second antibody is then allowed to bind to the JAB1. A third antibody specific to the second antibody is labeled and is passed over the solid support, and binding to the second antibody is detected.

Alternatively, detection may utilize staining of cells or histological sections, performed in accordance with conventional methods. Generally in such techniques, cells are permeabilized to stain cytoplasmic molecules. The antibodies of interest are added to the cell sample and incubated for a period of time sufficient to allow binding to the epitope, usually at least about 10 minutes. Again, the antibody may be labeled with radioisotopes, enzymes, fluorophores, chemiluminophores, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody may be conjugated to a fluorescent compound, e.g. fluorescein, rhodamine, Texas red, etc. Final detection typically uses a substrate that undergoes a color change in the presence of the peroxidase. The absence or presence of antibody binding may be determined by various methods, including flow cytometry of dissociated cells, microscopy, radiography, scintillation counting, etc.

Once the levels of expression for JAB1 in the patient sample is determined, the sample JAB1 expression level may be compared to the JAB1 expression level in normal samples, such as samples of undiseased tissue from the patient or to standardized levels of expression established in a population, for example. If the nuclear localization and/or level of expression for JAB1 in the patient sample is higher than the respective nuclear localization or level of expression for JAB1 in a normal sample or an established standard, a disease state may be diagnosed, and further diagnostic procedures may be administered and/or appropriate therapeutic measures may be taken. On the other hand, if the level of expression for JAB1 in the patient sample is lower than or substantially the same level as the level of expression for JAB1 in a normal sample or an established standard, a disease state may not be diagnosed.

In an alternative aspect to the method of using JAB1 expression for diagnosing a disease state as described above, the levels of expression of both JAB1 and p27 are measured. A ratio of JAB1 expression to p27 expression is determined for the patient sample and is then compared to the JAB1/p27 ratio from a normal sample of undiseased tissue from the patient or to a standardized level of expression established in a population, for example. It should be noted that a ratio of expression does not need to be made before comparison, since the level of JAB1 expression and the level of p27 expression in the patient sample may each be compared separately to the level of JAB1 expression and the level of p27 expression in the normal sample or standard. In any case, if the ratio of the level of expression of JAB1 to p27 in the patient sample is higher than the ratio of the level of expression of JAB1 to p27 in the normal sample or an established standard, a disease state may be diagnosed and appropriate further action can be taken. On the other hand, if the ratio of the level of expression of JAB1 to p27 in the patient sample is lower than or substantially the same as the ratio of the level of expression of JAB1 to p27 in the normal sample or an established standard, a disease state may not be diagnosed and appropriate further action or no action may be taken.

III. Disease Prognosis

In addition and related to diagnostic methods, the present invention provides embodiments for prognostic methods. Two exemplary aspects of this embodiment are provided. A patient sample may be obtained at a time=1. Next, the level of JAB1 expression or the ratio of JAB1 expression to p27 expression for this first sample is determined. As described above, the sample can be of virtually any biological origin and the level of JAB1 expression (or the ratio of JAB1 expression to p27 expression) can be performed in any one of many different methods well known in the art. At time=2, another sample is obtained from the same patient, and the level JAB1 expression (or the ratio of JAB1 expression to p27 expression) for this second sample is determined. Next, the level of expression of JAB1 or the ratio of JAB1 expression to p27 expression of the first and second samples may be compared.

Similar to the diagnosis methods described supra, if the nuclear localization or overall level of expression of JAB1 or the ratio of the level of expression of JAB1 to p27 in the second sample is higher than the nuclear localization or level of expression of JAB1 or the ratio of the level of expression of JAB1 to p27 in the first sample, the prognosis would indicate an increasing state of disease, such as a poorer prognosis, and the necessity for appropriate intervention. On the other hand, if the level of expression of JAB1 or the ratio of the level of expression of JAB1 to p27 in the second sample is lower than or is substantially the same as the level of expression of JAB1 or the ratio of the level of expression of JAB1 to p27 in the first sample, the prognosis would indicate a stabilized or decreasing state of disease, and is a more favorable prognosis compared to that for a higher level of JAB1 expression or ratio of JAB1/p27.

In another embodiment, a patient sample is obtained from an individual at a time=1. Next, the level of JAB1 expression or the ratio of JAB1 expression to p27 expression for this first sample is determined. As described above, the sample can be of virtually any biological origin and the level of JAB1 expression (or the ratio of JAB1 expression to p27 expression) can be performed in any one of many different ways well known in the art. Next, the individual is treated with a therapeutic at time=2. At time=3, another patient sample is obtained from the individual, and the level JAB1 expression (or the ratio of JAB1 expression to p27 expression) for this second sample is determined. The level of expression of JAB1 or the ratio of JAB1 expression to p27 expression of the first and second samples are compared. As with the method described above, if the level of expression of JAB1 or the ratio of the level of expression of JAB1 to p27 in the second sample is higher than the level of expression of JAB1 or the ratio of the level of expression of JAB1 to p27 in the first sample, it would indicate that the therapeutic is not effective. On the other hand, if level of expression of JAB1 or the ratio of the level of expression of JAB1 to p27 in the second sample is lower than or is substantially the same as the level of expression of JAB1 or the ratio of the level of expression of JAB1 to p27 in the first sample, it would indicate that the therapeutic is effective.

Levels of expression of JAB1 and/or of JAB1 compared to p27 may identify tumor progression, aggressiveness, or invasiveness of the tumor, and/or it may be indicative of the stage of the cancer, which may provide prognosis for an individual. For example, when the JAB1 and/or JAB1/p27 level is increased compared to normal tissue, the stage of the cancer may be identified, and the higher the increase in expression level there is, the later the stage the cancer may be. In particular embodiments, an increased level of JAB1 or JAB1/p27 ratio may identify a late stage cancer, such as a metastatic cancer. For the particular embodiment of breast cancer, an increased JAB1 expression or JAB1/p27 ratio may identify the cancer as at least at stage II, such as stage III or IV.

Reagents useful for the diagnostic and prognostic methods of the present invention may be conveniently provided in kit form. Thus, the present invention encompasses kits that comprise JAB1 polypeptides, antibodies, and polynucleotides. In one embodiment, the kit comprises one or more of the following exemplary components in a suitable container: (1) one or more JAB1 polynucleotides (e.g., oligonucleotide primers or probes corresponding to the JAB1 cDNA sequence and capable of amplifying the target polynucleotides, or siRNA) or fragments thereof; (2) anti-JAB1 antibodies, which may be polyclonal or monoclonal; (3) JAB1 polypeptides or fragments thereof, optionally coated on a solid surface (such as a slide, multiple well plate, or test tube) for use as a standard or control; (4) a JAB1 polynucleotide (e.g., for use as positive controls in assays); (5) fluorescent or non-radioactive JAB1 oligonucleotide or probe corresponding to the JAB1 genomic sequence that can be used for in situ hybridization (FISH or NISH); (6) other necessary reagents or buffers, (7) and tubes or multiple well plates. Instructions for carrying out the detection methods of the invention and optionally calibration curves can also be included.

IV. Screening Assays

In yet another aspect, the present invention contemplates a method of screening candidate substances for their ability to affect or modulate JAB1 expression to thereby affect or modulate the growth, proliferation, or nonproliferation of cells, such as cancer cells.

A. Screening for Modulators of the Protein Function

The present invention further comprises methods for identifying modulators of the function of JAB1, such as the exemplary function of JAB1 interaction with a target, for example p27. These assays may comprise random screening of large libraries of candidate substances; alternatively, the assays may be used to focus on particular classes of compounds selected with an eye towards structural attributes that are believed to make them more likely to modulate the function of JAB1.

By function, it is meant that one may assay for the binding of JAB1 to its target, such as p27; one may assay the ability of JAB1 to function in a COP9 signalosome; one may assay for the ability of JAB1 to translocate a target subcellularly, such as between the nucleus and cytoplasm; or one may assay for any function of JAB1 that directly or indirectly affects proliferation of a cell in which it resides.

In specific embodiments, to identify a JAB1 modulator one generally will determine the binding of JAB1 to its target in the presence and absence of the candidate substance, a modulator defined as any substance that alters the binding. For example, a method generally comprises:

(a) providing a candidate modulator;
(b) admixing the candidate modulator with an isolated compound or cell, or a suitable experimental animal;
(c) measuring one or more characteristics of the compound, cell or animal in step (b); and
(d) comparing the characteristic measured in step (c) with the characteristic of the compound, cell or animal in the absence of said candidate modulator, wherein a difference between the measured characteristics indicates that said candidate modulator is, indeed, a modulator of the compound, cell or animal.

Assays may be conducted in cell free systems, in isolated cells, or in organisms including transgenic animals.

It will, of course, be understood that all the screening methods of the present invention are useful in themselves notwithstanding the fact that effective candidates may not be identified. The invention provides methods for screening for such candidates, not solely methods of finding them.

1. Modulators

As used herein the term "candidate substance" refers to any molecule that may potentially inhibit or enhance JAB1 activity. The candidate substance may be a protein or fragment thereof, a small molecule, or even a nucleic acid molecule. It may prove to be the case that the most useful pharmacological compounds will be compounds that are structurally related to the respective binding domain of JAB1, such as the p27-binding domain of JAB1. Using lead compounds to help develop improved compounds is know as "rational drug design" and includes not only comparisons with known inhibitors and activators, but predictions relating to the structure of target molecules.

The goal of rational drug design is to produce structural analogs of biologically active polypeptides or target compounds. By creating such analogs, it is possible to fashion drugs that are more active or stable than the natural molecules; that have different susceptibility to alteration; or that may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, for example, small molecule libraries that are believed to meet the basic criteria for useful drugs in an effort to "brute force" the identification of useful compounds. Screening of such libraries, including combinatorially-generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one that exerts its inhibitory or activating effect upstream, downstream or directly on JAB1. Regardless of the type of inhibitor or activator identified by the present screening methods, the effect of the inhibition or activator by such a compound results in, for example, inhibition of JAB1 binding to its target or reduction in expression of JAB1 as compared to that observed in the absence of the added candidate substance.

2. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

3. In Cyto Assays

The present invention also contemplates the screening of compounds for their ability to modulate JAB1 expression in cells. Various cell lines can be utilized for such screening assays, including cells specifically engineered for this purpose. For example, cells transfected with JAB1, such as cells comprising a labeled JAB1 polypeptide or a JAB1 polynucleotide encoding a detectable JAB1 polypeptide may be employed. The detectability of JAB1 may comprise color or fluorescence, for example.

Depending on the assay, culture may be required. The cell is examined using any of a number of different physiologic assays. Alternatively, molecular analysis may be performed, for example, looking at protein expression, mRNA expression (including differential display of whole cell or polyA RNA) and others. In specific embodiments, those of skill in the art may refer to in cyto assays as in vivo assays.

4. In Vivo Assays

In vivo assays may involve the use of various animal models, including non-human transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species, and mammals are preferred.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

Thus, the present invention in some embodiments provides methods of screening for a candidate substance that reduces JAB1 expression or inhibits binding of JAB1 to a target, such as p27. In some specific embodiments, the present invention is directed to a method for determining the ability of a candidate substance to inhibiting binding of JAB1 to a target, generally including the steps of administering a candidate substance to an animal; and determining the ability of the candidate substance to reduce the binding.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

Thus, creens for agents that inhibit the binding of JAB1 to its target, such as p27, may be of any suitable kind. Multiple screens may be used in succession to narrow a pool of candidate inhibitors. In specific aspects of the invention, an in vitro screen may include ELISA, such as to monitor by dye visualization the absence of binding of p27 to JAB1 in the presence of a potential inhibitor. An example of an in vivo screen is a cell-based assay, in which binding of JAB1 to p27 in the presence of potential inhibitors is visualized from within the cell, such as by fluorescence or X-ray. Another screen utilizes the p27 binding domain of JAB1 and/or the JAB1 binding domain of p27, for example, immobilized to a substrate such that when a potential inhibitor binds the immobilized domain, the binding is visualized, such as by presence or absence of color or fluorescence, for example. Finally, another screen that may be utilized is a two-hybrid screen wherein the JAB1 binding domain of p27 or the p27 binding domain of JAB1 are used as bait to identify peptides or polypeptides that bind at least in part thereto.

B. Two-Hybrid Screen

In yet another embodiment, proteins that interact with JAB1 may be identified by using a yeast two-hybrid system or a co-immunoprecipitation assay. The yeast two-hybrid system may be used to identify new protein targets for pharmaceutical intervention, determine the specific residues involved in a given protein-protein interaction, and find compounds that modulate protein interactions. The yeast two-hybrid system can also be used to identify previously unknown proteins that interact with a target protein by screening a two-hybrid library. The yeast two-hybrid system is outlined in U.S. Pat. No. 5,283,173 (incorporated herein by reference), and is a technique well known to those of skill in the art. Briefly, the method is designed to detect an interaction between a first test protein and a second test protein, in vivo, using reconstitution of the activity of a transcriptional activator. Two chimeric proteins that express hybrid proteins are prepared. The first hybrid protein contains the DNA-binding domain of a transcriptional activator fused to the first test protein, while the second hybrid protein contains a transcriptional activation domain fused to the second test protein. If the two test proteins interact, the two domains of the transcriptional activator are brought into close proximity, resulting in the transcription of a marker gene that contains a binding site for the DNA-binding domain. An assay can be performed to detect activity of the marker gene.

All yeast two-hybrid systems share a set of common elements: 1) a plasmid that directs the synthesis of a "bait"; the bait is a known protein which is fused to a DNA binding domain, 2) one or more reporter genes ("reporters") with upstream DNA binding sites for the bait, and 3) a plasmid that directs the synthesis of proteins fused to activation domains and other useful moieties ("activation tagged proteins" or "prey"). All current systems direct the synthesis of proteins that carry the activation domain at the amino terminus of the fusion, facilitating the expression of open reading frames encoded by cDNAs. DNA binding domains used in the yeast two-hybrid systems include the native *E. coli* LexA repressor protein (Gyuris et al., 1993), and the GAL4 protein (Chien et al., 1991). Some reporter genes that may be utilized in the yeast system included HIS3, LEU2, and lacZ.

Although most two-hybrid systems use yeast, mammalian variants may also be utilized. In one system, interaction of activation tagged VP16 derivatives with a Gal4-derived bait drives expression of reporters that direct the synthesis of Hygromycin B phosphotransferase, Chloramphenicol acetyl-transferase, or CD4 cell surface antigen (Fearon et al., 1992). In another system, interaction of VP16-tagged derivatives with Gal4-derived baits drives the synthesis of SV40 T antigen, which in turn promotes the replication of the prey plasmid, because the plasmid carries a SV40 origin (Vasavada et al., 1991).

Protein-protein interactions may also be studied by using biochemical techniques such as cross-linking, co-immunoprecipitation, and co-fractionation by chromatography, which are well known to those skilled in the art. The co-immunoprecipitation technique consists of (i) generating a cell lysate; (ii) adding an antibody to the cell lysate; (iii) precipitating and washing the antigen; and (iv) eluting and analyzing the bound proteins (Phizicky and Fields, 1995). The antigen used to generate the antibody can be a purified protein, or a synthetic peptide coupled to a carrier. Both monoclonal and polyclonal antibodies can be utilized in co-immunoprecipitation, or alternatively, a protein can be used which carries an epitope tag recognized by a commercially available antibody.

In specific embodiments of the present invention, JAB1 two hybrid baits identify enolase and glucose-6-phosphate dehydrogenase as interactors.

C. Screening for Modulators of JAB1 Expression

In some aspects of the invention, compositions that modulate JAB1 expression are screened. In specific embodiments, these modulators decrease JAB1 expression, although in alternative embodiments the modulators increase JAB1 expression. Particular characteristics that may be screened for include the ability of the modulator to indirectly or directly decrease JAB1 expression, such as by negatively affecting transcription of JAB1 or translation of a JAB1 message. In particular embodiments, the modulator physically binds to a JAB1 transcript, thereby inhibiting completion of its transcription, targeting the transcript for degradation, or inhibiting the translation of the transcript into a polypeptide. The physical binding may comprise hybridization of the modulator to the transcript through at least some complementary sequences.

An exemplary method of screening candidate substances for their ability to modulate JAB1 expression may comprise the steps of constructing or obtaining a JAB1 expression vector; transfecting cells of interest with the JAB1 expression vector; assaying for JAB1 expression level or the ratio of expression of JAB1 to p27 in the transfected cells at time=1; treating the transfected cells with a therapeutic agent at time=2; assaying for JAB1 expression level or the ratio of expression of JAB1 to p27 at time=3; comparing the expression level of JAB1 or the ratio of expression of JAB1 to p27 at time=1 and time=3; and determining the efficacy of the therapeutic agent to modulate JAB1 expression. The present invention also provides a recombinant cell line suitable for use in the exemplary method. The candidate therapeutic agent identified to modulate JAB1 expression according to a screening assay described herein may have utility in the treatment of proliferative disorders, particularly cancer, such as breast cancer or lymphoma. In addition, by choosing specific cell types for transfection, the screening method can be used to identify the types of cancers that are affected by JAB1 expression, and which may be treated by altering JAB1 expression levels.

Transformation or transfection techniques are well known in the art and can be found generally in Maniatis, Fritsch and Sambrook, Molecular Cloning: A Laboratory Manual. In general, when the host is a eukaryote, methods of transfection of DNA include calcium phosphate co-precipitates; or conventional mechanical procedures such as microinjection, electroporation, insertion of a plasmid encased in liposomes, or transduction using viral-based vectors. To monitor transfection efficiency, the cells may be cotransformed with a DNA molecule encoding a gene for a selectable phenotype, such as the herpes simplex thymidine kinase, green fluorescent protein and the like.

The transformed JAB1 cells used in certain of the assays according to the present invention may be any cells of interest including any cells from normal human tissues such as liver, heart, kidney, skin, prostate, and the like. Also, the transformed JAB1 cells used in aspects of the present invention may be those from solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, Merkel cell, mucinous, non-small cell lung, oat cell, papillary, scirrhous, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), hystiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, cranio-pharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pheochromocytoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia, and other cells that have become immortalized or transformed.

With respect to a representative method for the preparation of a transgenic mouse, cloned recombinant or synthetic DNA sequences or DNA segments encoding a JAB1 gene product are injected into fertilized mouse eggs (e.g. an embryo). The injected eggs are implanted in pseudo pregnant females and are grown to term to provide transgenic mice whose cells express a JAB1 gene product. Because the expression of JAB1 may be deleterious to the animal, JAB1 expression in the chimera or transgenic offspring produced by germ line transmission of the DNA sequence may be established through incorporation of the JAB1 gene under the control of an inducible promoter. The expression of the JAB1 protein is then induced by treatment of the chimera or transgenic offspring thereof with the inducing agent.

V. Therapeutics

A particularly important aspect of the present invention is treatment of cancers characterized by increased JAB1 expression compared to expression in normal tissue or a high ratio of JAB1/p27 compared to a normal cell or tissue. JAB1-inhibiting agents may be provided to inhibit the binding of JAB1 to a target, or the expression of JAB1 itself may be useful as a therapeutic target. In specific embodiments, gene therapy vectors and substances that inhibit expression of JAB1 are used as therapeutics to treat cancer. An individual with cancer at least in part resulting directly or indirectly from a high level of JAB1 expression or otherwise characterized by a high level of expression or an abnormal ratio of JAB1 expression to p27 expression is identified. One or more JAB1 expression-reducing agents is administered to the individual.

In particular embodiments, a therapeutic composition comprises a composition identified by any suitable screen, such as a screen described herein. Exemplary JAB1-inhibiting substances including antisense and RNAi agent expression constructs of the present invention, which may be used in the treatment of cancer, including solid tumors, breast cancers, pituitary carcinomas, lymphomas, prostate, pancreatic, colon, and lung, for example. In conjunction with the inventive therapy described herein, there may be additional cancer therapy provided to an individual, such as prior to the JAB1-associated treatment, during the JAB1-associated treatment, or subsequent to the JAB1-associated treatment. Additional cancer therapies include chemotherapy, hormone therapy, drug therapy, radiation, surgery, gene therapy, or immunotherapy, for example.

Therapeutics that inhibit expression of JAB1 can be identified by the screening assays described herein. The method of administration shall depend on the nature of the therapeutic, and a skilled artisan is aware of methods and reagents suitable for determining same. For example, a JAB1 nucleic acid can be used as a tool for gene therapy in humans to treat cancer. Exemplary gene therapy methods, including liposomal transfection of nucleic acids into host cells, are described in U.S. Pat. Nos. 5,279,833; 5,286,634; 5,399,346; 5,646,008; 5,651,964; 5,641,484; and 5,643,567, the contents of each of which are herein incorporated by reference. Exemplary JAB1 nucleic acids from which therapeutic antisense RNAs may be derived include GenBank Accession No. U65928 (SEQ ID NO:8) from the World Wide Web site of the National Center for Biotechnology Information or the following GenBank Accession Nos.: NM_006837 (SEQ ID NO:9); BC001859; (SEQ ID NO:14); BC007272 (SEQ ID NO: 15); and BC001187 (SEQ ID NO:16). For any embodiments of the invention wherein a JAB1 polypeptide is utilized, an example of such may be obtained from GenBank No. NP_006828 (SEQ ID NO:10).

In one aspect of a gene therapy embodiment, antisense RNAs against JAB1 provide treatment of the cancer caused by JAB1 expression. Therapeutic methods utilizing antisense oligonucleotides have been described in the art, for example in U.S. Pat. Nos. 5,627,158 and 5,734,033, the contents of each of which are herein incorporated by reference. The antisense RNAs can be delivered to the tumor or cancer cells directly or may be expressed in the cells by a gene therapy vector. Antisense gene therapy vectors include promoters, terminators and possibly other genetic elements for expression. Exemplary promoters, terminators and the like are described herein infra in the discussion of RNAi agents.

In general, the specific hybridization of an antisense RNA with its target nucleic acid interferes with the normal function of the target nucleic acid. The functions of RNA that may be interfered with include all vital functions such as, for example, translocation of the RNA to the site of protein translation, translation of protein, splicing of the RNA to yield one or more mRNA species, and catalytic activity which may be engaged in or facilitated by the RNA. The overall effect of such interference with target nucleic acid function is modulation of the expression of the JAB1 protein. In the context of the present invention, inhibition of JAB1 is the preferred form of modulation of gene expression and mRNA is the preferred target.

"Targeting" an antisense compound to a particular nucleic acid is a multistep process. The process usually begins with the identification of a nucleic acid sequence whose function is to be modulated, in this case, the target is a nucleic acid molecule encoding JAB1. The targeting process also includes determination of a site or sites within the JAB1 gene for the antisense interaction to occur such that the desired effect—inhibition of expression of the protein—will result. A preferred intragenic site may be the region encompassing the translation initiation or termination codon of the open reading frame (ORF) of the gene.

Alternatively, the ORF or "coding region," which is the region between the translation initiation codon and the translation termination codon, is also a region which may be targeted effectively. Other target regions include the 5' untranslated region (5'UTR), the portion of an mRNA in the 5' direction from the translation initiation codon including nucleotides between the 5' cap site and the translation initiation codon of the mRNA, and the 3' untranslated region (3'UTR), the portion of an mRNA in the 3' direction from the translation termination codon including nucleotides between the translation termination codon and 3' end of an mRNA. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 or so nucleotides adjacent to the cap. The 5' cap region may also be a preferred target region. Also, mRNA splice sites, i.e., intron-exon junctions, also may be preferred target regions, and are particularly useful in situations where aberrant splicing is implicated in disease, or where an overproduction of a particular mRNA splice product is implicated in disease.

Once one or more target sites have been identified, oligonucleotides are chosen which are sufficiently complementary to the target, i.e., hybridize sufficiently well and with sufficient specificity, to give the desired effect. "Hybridization" means hydrogen bonding, which may be Watson-Crick, Hoogsteen or reversed Hoogsteen hydrogen bonding, between complementary nucleoside or nucleotide bases. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired; i.e., under physiological conditions in the case of in vivo assays or therapeutic treatment, and in the case of in vitro assays, under conditions in which the assays are performed.

A. Antisense RNA, RNAi, and siRNA

In one aspect of the present invention, interfering RNAs are used. RNA interference (RNAi) is a phenomenon describing double-stranded (ds)RNA-dependent gene specific post-transcriptional silencing. Initial attempts to harness this phenomenon for experimental manipulation of mammalian cells were foiled by a robust and nonspecific antiviral defense mechanism activated in response to long dsRNA molecules; however, the field was significantly advanced upon the demonstration that synthetic duplexes of 21 nucleotide RNAs could mediate gene specific RNAi in mammalian cells without invoking generic antiviral defense mechanisms. As a result, small-interfering RNAs (siRNAs) have become powerful tools to dissect gene function. The chemical synthesis of small RNAs to be delivered directly to cells is one avenue that has produced promising results; on the other hand, numerous groups have also sought the development of DNA-based vectors capable of generating siRNA within cells.

The sequences for the RNAi agents, such as the siRNAs, are selected based upon the genetic sequence of the target JAB1 nucleic acid sequence; and preferably are based on regions of target nucleic acid sequences that are conserved. As oncogenes are known to mutate rapidly, selection of conserved sequences is likely to preserve the efficacy of the RNAi over time.

In general, inhibition of target sequences by RNAi requires a high degree of sequence homology between the target sequence and the sense strand of the RNAi molecules. In some embodiments, such homology is higher than about 70%, and may be higher than about 75%. Preferably, homology is higher than about 80%, and is higher than 85% or even 90%. More preferably, sequence homology between the target sequence and the sense strand of the RNAi is higher than about 90%, 91%, 92%, 93%, 94%, 95%, 96%, 97%, 98% or 99%.

In addition to selecting the RNAi sequences having a high degree of homology to conserved regions of a JAB1 target sequence, selection of the RNAi sequences may be based on other factors. Despite a number of attempts to devise selection criteria for identifying sequences that are effective for RNAi based on features of the desired target sequence (e.g., percent GC content, position from the translation start codon, thermodynamic pairing criteria), it is presently not possible to predict with much degree of confidence which of the myriad possible candidate RNAi sequences that correspond to a desired segment of the JAB1 sequence will, in fact, elicit an RNA silencing response. Instead, individual specific candidate RNAi polynucleotide sequences typically are generated and tested.

There is no particular limitation in the length of the RNAi agents of the present invention as long as they are effective in inhibiting JAB1 expression. The RNAi agents can be, for example, 10 to 50 bp in length, preferably 12 to 40 bp in length, and are more preferably 15 to 33 bp in length. The double-stranded RNA portions of RNAis may be completely homologous, or may contain non-paired portions due to sequence mismatch (the corresponding nucleotides on each strand are not complementary), bulge (lack of a corresponding complementary nucleotide on one strand), and the like. Such non-paired portions can be tolerated to the extent that they do not significantly interfere with RNAi duplex formation or efficacy. In embodiments wherein siRNAs are employed, these molecules are preferably about 21 nt in length.

The termini of an RNAi agents according to the present invention may be blunt or cohesive (overhanging) as long as the RNAi effectively silences the JAB1 target gene. The cohesive (overhanging) end structure is not limited only to a 3' overhang, but a 5' overhanging structure may be included as long as the resulting RNAi is capable of inhibiting the expression of JAB1. In addition, the number of overhanging nucleotides may be any number as long as the resulting RNAi agent is capable of inducing the RNAi effect. For example, if present, the overhang may consist of 1 to 8 nucleotides, preferably it consists of 2 to 4 nucleotides.

As stated, RNAi polynucleotide sequences (RNAi agents) may be delivered directly to the cell or tissue, or may be expressed in the cell by an expression vector. Various chemical modifications have been made to short-interfering RNAs (siRNAs) for direct delivery into a cell or tissue to stabilize and optimize the biochemical properties required for RNA interference (RNAi). Modifications at the 2'-position of pentose sugars in siRNAs showed the 2'-OHs were not required for RNAi, indicating that RNAi machinery does not require the 2'-OH for recognition of siRNAs and catalytic ribonuclease activity of RNA-induced silencing complexes (RISCs) does not involve the 2'-OH of guide antisense RNA. However, 2' modifications increased the persistence of RNAi as compared with wild-type siRNAs.

RNAi also has been induced with chemical modifications that stabilize the interactions between A-U base pairs, demonstrating that these types of modifications may enhance mRNA targeting efficiency in allele-specific RNAi. Modifications altering the structure of the A-form major groove of antisense siRNA-mRNA duplexes abolished RNAi, suggesting that the major groove of these duplexes is required for recognition by activated RISC. Comparative analysis of the stability and RNAi activities of chemically-modified single-stranded antisense RNA and duplex siRNA suggested that some catalytic mechanism(s) other than siRNA stability were linked to RNAi efficiency. In addition, modified or mismatched ribonucleotides incorporated at internal positions in the 5' or 3' half of the siRNA duplex, as defined by the antisense strand, shows that the integrity of the 5' half, but not the 3' half, of the siRNA structure is important for RNAi, highlighting the asymmetric nature of siRNA recognition for initiation of unwinding.

In addition, it has been found that RNA duplexes containing either phosphodiester or varying numbers of phosphorothioate linkages are remarkably stable during prolonged incubations in serum. Treatment of cells with RNA duplexes containing phosphorothioate linkages leads to selective inhibition of gene expression. RNAi also tolerates the introduction of 2'-deoxy-2'-fluorouridine or locked nucleic acid (LNA) nucleotides. Introduction of LNA nucleotides also increases substantially the thermal stability of modified RNA duplexes without compromising the efficiency of RNAi. Other modifications are known in the art and are currently in development.

As an alternative to directly delivering antisense or RNAi agents to cells, the antisense or RNAi agents may be genetically engineered as part of a gene therapy vector where the vector is used to transform the cancer cells and express the antisense or RNAi agents in the cells. The constructs into which the antisense or RNAi agent is inserted and used for high efficiency transduction and expression of the RNAis in various cell types preferably are derived from viruses and are compatible with viral delivery. Generation of the construct can be accomplished using any suitable genetic engineering techniques well known in the art, including without limitation, the standard techniques of PCR, oligonucleotide synthesis, restriction endonuclease digestion, ligation, transformation, plasmid purification, and DNA sequencing. The construct preferably comprises, for example, sequences necessary to package the antisense or RNAi agent expression construct into viral particles and/or sequences that allow integration of the antisense or RNAi agent expression construct into the target cell genome. The viral construct also may contain genes that allow for replication and propagation of virus, though in preferred embodiments such genes will be supplied in trans. Additionally, the viral construct may contain genes or genetic sequences from the genome of any known organism incorporated in native form or modified. For example, the preferred viral construct comprises sequences useful for replication of the construct in bacteria.

The construct also may contain additional genetic elements. The types of elements that may be included in the construct are not limited in any way and may be chosen by one with skill in the art. For example, additional genetic elements may include a reporter gene, such as one or more genes for a fluorescent marker protein such as GFP or RFP; an easily assayed enzyme such as beta-galactosidase, luciferase, beta-glucuronidase, chloramphenical acetyl transferase or secreted embryonic alkaline phosphatase; or proteins for which immunoassays are readily available such as hormones or cytokines. Other genetic elements that may find use in embodiments of the present invention include those coding for proteins which confer a selective growth advantage on cells such as adenosine deaminase, aminoglycodic phosphotransferase, dihydrofolate reductase, hygromycin-B-phosphotransferase, or those coding for proteins that provide a biosynthetic capability missing from an auxotroph. If a reporter gene is included along with the antisense or RNAi agent expression cassette, an internal ribosomal entry site (IRES) sequence can be included. Preferably, the additional genetic elements are operably linked with and controlled by an independent promoter/enhancer.

Figure 20:
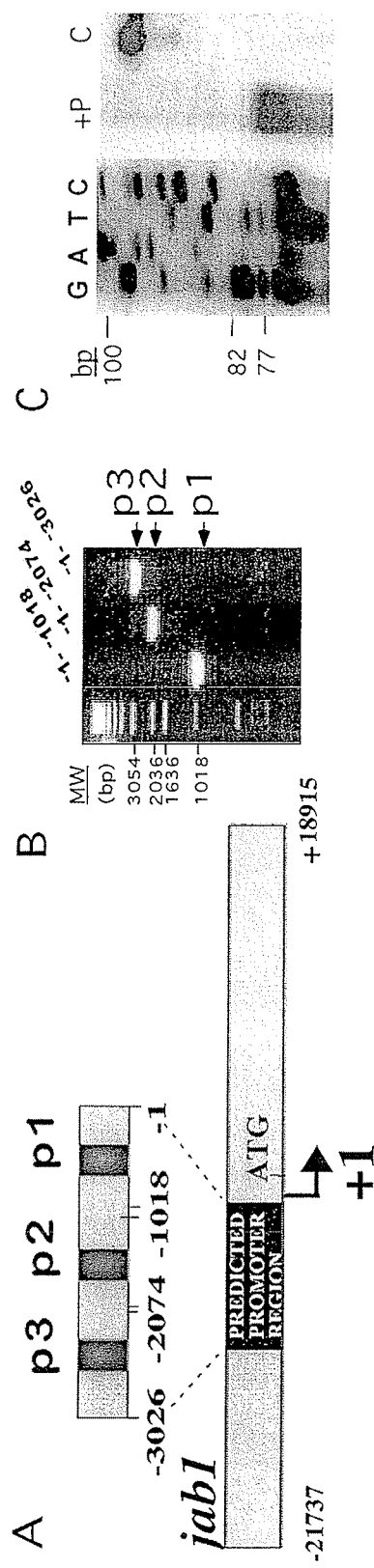
FIGS. 20A-20C demonstrate characterization of the JAB1 promoter region and its transcriptional start site.

A "promoter" or "promoter sequence" is a DNA regulatory region capable of binding RNA polymerase in a cell and initiating transcription of a polynucleotide or polypeptide coding sequence such as messenger RNA, ribosomal RNAs, small nuclear of nucleolar RNAs or any kind of RNA transcribed by any class of any RNA polymerase I, II or III. In some embodiments, promoters of variable strength may be employed, but preferably for expression of JAB1 in cells, strong promoters are used. Use of strong promoters (such as a Pol III-type promoter) not only expresses JAB1 at a high level, but may synergistically work to inhibit cancer cell progression by taxing the cell, by, e.g., depleting the pool of available nucleotides or other cellular components needed for transcription of other genes. For JAB1 promoter embodiments, see FIG. 20.

In addition, tissue-specific or cell-specific promoters may be employed. The term "tissue specific" as it applies to a promoter refers to a promoter that is capable of directing selective expression of a nucleotide sequence of interest to a specific type of tissue (e.g., liver) in the relative absence of expression of the same nucleotide sequence of interest in a different type of tissue (e.g., brain). Such tissue specific promoters include promoters such as lck, myogenin, or thy1. The term "cell-specific" as applied to a promoter refers to a promoter which is capable of directing selective expression of a nucleotide sequence of interest in a specific type of cell in the relative absence of expression of the same nucleotide sequence of interest in a different type of cell within the same tissue (see, e.g., Higashibata, et al., J. Bone Miner. Res. January 19(1):78-88 (2004); Hoggatt, et al., Circ. Res., December 91(12):1151-59 (2002); Sohal, et al., Circ. Res. July 89(1): 20-25 (2001); and Zhang, et al., Genome Res. January 14(1): 79-89 (2004)). The term "cell-specific" when applied to a promoter also means a promoter capable of promoting selective expression of a nucleotide sequence of interest in a region within a single tissue. Alternatively, promoters may be constitutive or regulatable. Additionally, promoters may be modified so as to possess different specificities.

The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a coding sequence in substantially any cell and any tissue. The promoters used to transcribe the JAB1 RNAi species preferably are constitutive promoters, such as the promoters for ubiquitin, CMV, β-actin, histone H4, EF-1alfa or pgk genes controlled by RNA polymerase II, or promoter elements controlled by RNA polymerase I. In preferred embodiments, promoter elements controlled by RNA polymerase III are used, such as the U6 promoters (U6-1, U6-8, U6-9, e.g.), H1 promoter, 7SL promoter, the human Y promoters (hY1, hY3, hY4 (see Maraia, et al., Nucleic Acids Res 22(15):3045-52 (1994)) and hY5 (see Maraia, et al., Nucleic Acids Res 24(18):3552-59 (1994)), the human MRP-7-2 promoter, Adenovirus VA1 promoter, human tRNA promoters, the 5s ribosomal RNA promoters, as well as functional hybrids and combinations of any of these promoters.

Alternatively in some embodiments it may be optimal to select promoters that allow for inducible expression of the JAB1 RNAi species. A number of systems for the inducible expression using such promoters are known in the art, including but not limited to the tetracycline responsive system and the lac operator-repressor system (see WO 03/022052 A1; and US 2002/0162126 A1), the ecdyson regulated system, or promoters regulated by glucocorticoids, progestins, estrogen, RU-486, steroids, thyroid hormones, cyclic AMP, cytokines, the calciferol family of regulators, or the metallothionein promoter (regulated by inorganic metals).

As stated, the JAB1 RNAi coding regions of the RNAi expression vector are operatively linked to terminator elements. In one embodiment, the terminators comprise stretches of four or more thymidine residues. In another embodiment, the terminator elements used are matched to the promoter elements from the gene from which the terminator is derived. Such terminators include the SV40 poly A, the Ad VA1 gene, the 5S ribosomal RNA gene, and the terminators for human t-RNAs. In addition, promoters and terminators may be mixed and matched, as is commonly done with RNA pol II promoters and terminators.

The termini of an RNAi species according to the present invention may be blunt or cohesive (overhanging) as long as the RNAi effectively silences the target gene. The cohesive (overhanging) end structure is not limited only to a 3' overhang, but a 5' overhanging structure may be included as long as the resulting RNAi is capable of inducing the RNAi effect. In addition, the number of overhanging nucleotides may be any number as long as the resulting RNAi is capable of inducing the RNAi effect. For example, if present, the overhang may consist of 1 to 8 nucleotides, preferably it consists of 2 to 4 nucleotides.

B. Delivery Systems

Any delivery system suitable in the art may be employed to provide to a cancer cell of an individual a therapeutic composition in accordance with the present invention. Vectors may be utilized, including viral or non-viral vectors. One vector that may be useful comprises one or more encapsulated cells expressing the therapeutic compound (an siRNA, for example), which could be used also as implant in solid tumor (e.g. for brain tumor, spinal cord, etc.) to treat cancer.

A viral delivery system based on any appropriate virus may be used to deliver the antisense or RNAi agent expression constructs of the present invention. In addition, hybrid viral systems may be of use. The choice of viral delivery system will depend on various parameters, such as the tissue targeted for delivery, transduction efficiency of the system, pathogenicity, immunological and toxicity concerns, and the like. Given the diversity of cancers and proliferative disease that are amenable to interference by the antisense or RNAi agent expression constructs of the present invention, it is clear that there is no single viral system that is suitable for all applications. When selecting a viral delivery system to use in the present invention, it is important to choose a system where the antisense or RNAi agent expression construct-containing viral particles are preferably: 1) reproducibly and stably propagated; 2) able to be purified to high titers; and 3) able to mediate targeted delivery (delivery of the antisense or RNAi agent expression construct to the tissue or organ of interest without widespread dissemination).

In general, the five most commonly used classes of viral systems used in gene therapy can be categorized into two groups according to whether their genomes integrate into host cellular chromatin (oncoretroviruses and lentiviruses) or persist in the cell nucleus predominantly as extrachromosomal episomes (adeno-associated virus, adenoviruses and herpesviruses). This distinction is an important determinant of the suitability of each vector for particular applications; non-integrating vectors can, under certain circumstances, mediate persistent gene expression in non-proliferating cells, but integrating vectors are the tools of choice if stable genetic alteration needs to be maintained in dividing cells, particularly in the present invention where the target cells are rapidly proliferating cancer cells.

For example, in one embodiment of the present invention, viruses from the Parvoviridae family are utilized. The Parvoviridae is a family of small single-stranded, non-enveloped DNA viruses with genomes approximately 5000 nucleotides long. Included among the family members is adeno-associated virus (AAV), a dependent parvovirus that by definition requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells.

Once in the nucleus, the virus uncoats and the transgene is expressed from a number of different forms—the most persistent of which are circular monomers. AAV will integrate into the genome of 1-5% of cells that are stably transduced (Nakai, et al., *J. Virol.* 76:11343-349 (2002). Expression of the transgene can be exceptionally stable and in one study with AAV delivery of Factor IX, a dog model continues to express therapeutic levels of the protein 4.5 years after a single direct infusion with the virus. Because progeny virus is not produced from AAV infection in the absence of helper virus, the extent of transduction is restricted only to the initial cells that are infected with the virus. It is this feature which makes AAV a non-preferred gene therapy vector for the present invention. However, unlike retrovirus, adenovirus, and herpes simplex virus, AAV appears to lack human pathogenicity and toxicity (Kay, et al., *Nature*. 424: 251 (2003) and Thomas, et al., *Nature Reviews Genetics* 4:346-58 (2003)).

Typically, the genome of AAV contains only two genes. The "rep" gene codes for at least four separate proteins utilized in DNA replication. The "cap" gene product is spliced differentially to generate the three proteins that comprise the capsid of the virus. When packaging the genome into nascent virus, only the Inverted Terminal Repeats (ITRs) are obligate sequences; rep and cap can be deleted from the genome and be replaced with heterologous sequences of choice. However, in order produce the proteins needed to replicate and package the AAV-based heterologous construct into nascent virion, the rep and cap proteins must be provided in trans. The helper functions normally provided by co-infection with the helper virus, such as adenovirus or herpesvirus mentioned above, also can be provided in trans in the form of one or more DNA expression plasmids. Since the genome normally encodes only two genes it is not surprising that, as a delivery vehicle, AAV is limited by a packaging capacity of 4.5 single stranded kilobases (kb). However, although this size restriction may limit the genes that can be delivered for replacement gene therapies, it does not adversely affect the packaging and expression of shorter sequences such as RNAi nucleic acids.

However, technical hurdles must be addressed when using AAV as a vehicle for antisense or RNAi agent expression constructs. For example, various percentages of the human population may possess neutralizing antibodies against certain AAV serotypes. However, since there are several AAV serotypes, some of which the percentage of individuals harboring neutralizing antibodies is vastly reduced, other serotypes can be used or pseudo-typing may be employed. There are at least eight different serotypes that have been characterized, with dozens of others which have been isolated but have been less well described. Another limitation is that as a result of a possible immune response to AAV, AAV-based therapy may only be administered once; however, use of alternate, non-human derived serotypes may allow for repeat administrations. Administration route, serotype, and composition of the delivered genome all influence tissue specificity.

Another limitation in using unmodified AAV systems with the antisense or RNAi agent expression constructs is that transduction can be inefficient. Stable transduction in vivo may be limited to 5-10% of cells. Yet, different methods are known in the art to boost stable transduction levels. One approach is utilizing pseudotyping, where AAV-2 genomes are packaged using cap proteins derived from other serotypes. One group of investigators exhaustively pseudotyped AAV-2 with AAV-1, AAV-3B, AAV-4, AAV-5, and AAV-6 for tissue culture studies. The highest levels of transgene expression were induced by virion which had been pseudotyped with AAV-6; producing nearly 2000% higher transgene expression than AAV-2. Thus, the present invention contemplates use of a pseudotyped AAV virus to achieve high transduction levels, with a corresponding increase in the expression of the RNAi multiple-promoter expression constructs.

Another viral delivery system useful with the multiple-promoter RNAi expression constructs of the present invention is a system based on viruses from the family Retroviridae. Retroviruses comprise single-stranded RNA animal viruses that are characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus can then integrate into the host genome and be passed from parent cell to progeny cells as a stably-integrated component of the host genome.

In some embodiments, lentiviruses are the preferred members of the retrovirus family for use in the present invention. Lentivirus vectors are often pseudotyped with vesicular stomatitis virus glycoprotein (VSV-G), and have been derived from the human immunodeficiency virus (HIV), the etiologic agent of the human acquired immunodeficiency syndrome (AIDS); visan-maedi, which causes encephalitis (visna) or pneumonia in sheep; equine infectious anemia virus (EIAV), which causes autoimmune hemolytic anemia and encephalopathy in horses; feline immunodeficiency virus (FIV), which causes immune deficiency in cats; bovine immunodeficiency virus (BIV) which causes lymphadenopathy and lymphocytosis in cattle; and simian immunodeficiency virus (SIV), which causes immune deficiency and encephalopathy in non-human primates. Vectors that are based on HIV generally retain <5% of the parental genome, and <25% of the genome is incorporated into packaging constructs, which minimizes the possibility of the generation of reverting replication-competent HIV. Biosafety has been further increased by the development of self-inactivating vectors that contain deletions of the regulatory elements in the downstream long-terminal-repeat sequence, eliminating transcription of the packaging signal that is required for vector mobilization.

Reverse transcription of the retroviral RNA genome occurs in the cytoplasm. Unlike C-type retroviruses, the lentiviral cDNA complexed with other viral factors—known as the pre-initiation complex—is able to translocate across the nuclear membrane and transduce non-dividing cells. A structural feature of the viral cDNA—a DNA flap—seems to contribute to efficient nuclear import. This flap is dependent on the integrity of a central polypurine tract (cPPT) that is located in the viral polymerase gene, so most lentiviral-derived vectors retain this sequence. Lentiviruses have broad tropism, low inflammatory potential, and result in an integrated vector. The main limitations are that integration might induce oncogenesis in some applications. The main advantage to the use of lentiviral vectors is that gene transfer is persistent in most tissues or cell types.

A lentiviral-based construct used to express the antisense or RNAi agent agents preferably comprises sequences from the 5' and 3' LTRs of a lentivirus. More preferably the viral construct comprises an inactivated or self-inactivating 3' LTR from a lentivirus. The 3' LTR may be made self-inactivating by any method known in the art. In a preferred embodiment, the U3 element of the 3' LTR contains a deletion of its enhancer sequence, preferably the TATA box, Sp1 and NF-kappa B sites. As a result of the self-inactivating 3' LTR, the provirus that is integrated into the host ell genome will comprise an inactivated 5' LTR. The LTR sequences may be LTR sequences from any lentivirus from any species. The lentiviral-based construct also may incorporate sequences for MMLV or MSCV, RSV or mammalian genes. In addition, the U3 sequence from the lentiviral 5' LTR may be replaced with a promoter sequence in the viral construct. This may increase the titer of virus recovered from the packaging cell line. An enhancer sequence may also be included.

Adenoviruses are non-enveloped viruses containing a linear double-stranded DNA genome. While there are over 40 serotype strains of adenovirus—most of which cause benign respiratory tract infections in humans—subgroup C serotypes 2 or 5 are predominantly used as vectors. The adenovirus life cycle normally does not involve integration into the host genome, rather it replicates as episomal elements in the nucleus of the host cell and consequently there is no risk of insertional mutagenesis. The wildtype adenovirus genome is approximately 35 kb of which up to 30 kb can be replaced with foreign DNA. There are four early transcriptional units (E1, E2, E3 and E4), which have regulatory functions, and a late transcript, which codes for structural proteins. Progenitor vectors have either the E1 or E3 gene inactivated, with the missing gene being supplied in trans either by a helper virus, plasmid or by an integrated gene in a helper cell genome. Second generation vectors additionally use an E2a temperature sensitive mutant or an E4 deletion. The most recent "gutless" vectors contain only the inverted terminal repeats (ITRs) and a packaging sequence around the transgene, all the necessary viral genes being provided in trans by a helper virus.

Adenoviral vestors are very efficient at transducing target cells in vitro and in vivo, and can be produced at high titres ($>10^{11}$/ml). With the exception of one study that showed prolonged transgene expression in rat brains using an E1 deletion vector, transgene expression in vivo from progenitor vectors tends to be transient. Following intravenous injection, 90% of the administered vector is degraded in the liver by a non-immune mediated mechanism. Thereafter, an MHC class I restricted immune response occurs, using CD8+ CTLs to eliminate virus infected cells and CD4+ cells to secrete IFN-alpha which results in anti-adenoviral antibody. Alteration of the adenoviral vector can remove some CTL epitopes; however, the epitopes recognized differ with the host MHC haplotype. The remaining vectors, in those cells that are not destroyed, have their promoter inactivated and persisting antibody prevents subsequent administration of the vector.

Approaches to avoid the immune response involving transient immunosuppressive therapies have been successful in prolonging transgene expression and achieving secondary gene transfer. A less interventionist method has been to induce oral tolerance by feeding the host UV inactivated vector. However, it is more desirable to manipulate the vector rather than it is to manipulate the host through immunosuppression. Although only replication deficient vectors are used, viral proteins are expressed at a very low level, which are then presented to the immune system. The development of vectors containing fewer genes—culminating in the "gutless" vectors which contain no viral coding sequences—has resulted in prolonged in vivo transgene expression in liver tissue. However, the initial delivery of DNA packaged within adenovirus proteins—the majority of which will be degraded and presented to the immune system—may still cause problems for clinical trials.

Until recently, the mechanism by which the adenovirus targeted the host cell was poorly understood. Tissue-specific expression was therefore only possible by using cellular promoter/enhancers, e.g., the myosin light chain 1 promoter or the smooth muscle cell SM22a promoter, or by direct delivery to a local area. Uptake of the adenovirus particle has been shown to be a two-stage process involving an initial interaction of a fiber coat protein in the adenovirus with a cellular receptor or receptors, which include the MHC class I molecule and the coxsackievirus-adenovirus receptor. The penton base protein of the adenovirus particle then binds to the integrin family of cell surface heterodimers allowing internalization via receptor mediated endocytosis. Most cells express primary receptors for the adenovirus fiber coat protein, however internalization is more selective. Methods of increasing viral uptake include stimulating the target cells to express an appropriate integrin and conjugating an antibody with specificity for the target cell type to the adenovirus. However, the use of antibodies increases the production difficulties of the vector and the potential risk of activating the complement system.

Another virus that may be used as a basis for a viral delivery vector in the present invention is the Herpes simplex virus-1. HSV-1 is a double-stranded DNA virus with a packaging capacity of 40 kb, or up to 150 kb (helper dependent). HSV-1 has strong tropism for neurons, but also has a high inflammatory potential. HSV-1 is maintained episomally. Replication defective HSV-1 vectors generally are produced by deleting all, or a combination, of the five immediate-early genes (ICP0, ICP4, ICP22, ICP27 and ICP47), which are required for lytic infection and expression of all other viral proteins. Unfortunately, the ICP0 gene product is both cytotoxic and required for high level and sustained transgene expression. As such, the production of non-toxic quintuple immediate-early mutant vectors is a trade-off against efficient and persistent transgene expression. An HSV-1 protein that is activated during latency has recently be shown to complement mutations in ICP0 and overcome the repression of transgene expression that occurs in the absence of ICP0, Substitution of this protein in place of ICP0 might facilitate efficient transgene expression without cytotoxicity in non-neuronal cells. Long-term expression can be achieved in the nervous system by using one of the HSV-1 neuron-specific latency-activated promoters to drive transgene expression.

Other viral or non-viral systems known to those skilled in the art may be used to deliver the antisense or RNAi agent expression cassettes of the present invention to cells of interest, including but not limited to gene-deleted adenovirus-transposon vectors that stably maintain virus-encoded transgenes in vivo through integration into host cells (see, Yant, et al., *Nature Biotech.* 20:999-1004 (2002)); systems derived from Sindbis virus or Semliki forest virus (see Perri, et al, *J. Virol.* 74(20):9802-07 (2002)); systems derived from Newcastle disease virus or Sendai virus; or mini-circle DNA vectors devoid of bacterial DNA sequences (see Chen, et al., *Molecular Therapy.* 8(3):495-500 (2003)). In addition, hybrid viral systems may be used to combine useful properties of two or more viral systems.

To deliver a viral-based antisense or RNAi agent expression construct into target cells, the expression construct first must be packaged into viral particles. Any method known in the art may be used to produce infectious viral particles whose genome comprises a copy of the viral antisense or RNAi agent expression construct. For example, certain methods utilize packaging cells that stably express in trans the viral proteins that are required for the incorporation of the viral antisense or RNAi agent expression construct into viral particles, as well as other sequences necessary or preferred for a particular viral delivery system (for example, sequences needed for replication, structural proteins and viral assembly) and either viral-derived or artificial ligands for tissue entry. In such a method, an antisense or RNAi agent expression cassette is ligated to a viral delivery vector and the resulting viral antisense or RNAi agent expression construct is used to transfect packaging cells. The packaging cells then replicate viral sequences, express viral proteins and package the viral antisense or RNAi agent expression constructs into infectious viral particles (step 420). The packaging cell line may be any cell line that is capable of expressing viral proteins, including but not limited to 293, HeLa, A549, PerC6, D17, MDCK, BHK, bing cherry, phoenix, Cf2Th, or any other line known to or developed by those skilled in the art. One packaging cell line is described, for example, in U.S. Pat. No. 6,218,181.

Alternatively, a cell line that does not stably express necessary viral proteins may be co-transfected with two or more constructs to achieve efficient production of functional particles. One of the constructs comprises the viral antisense or RNAi agent expression construct, and the other plasmid(s) comprises nucleic acids encoding the proteins necessary to allow the cells to produce functional virus (replication and packaging construct) as well as other helper functions. This method utilizes cells for packaging that do not stably express viral replication and packaging genes. In this case, the antisense or RNAi agent expression construct is ligated to the viral delivery vector and then co-transfected with one or more vectors that express the viral sequences necessary for replication and production of infectious viral particles. The cells replicate viral sequences, express viral proteins and package the viral antisense or RNAi agent expression constructs into infectious viral particles.

The packaging cell line or replication and packaging construct may not express envelope gene products. In these embodiments, the gene encoding the envelope gene can be provided on a separate construct that is co-transfected with the viral antisense or RNAi agent expression construct. As the envelope protein is responsible, in part, for the host range of the viral particles, the viruses may be pseudotyped. As described supra, a "pseudotyped" virus is a viral particle having an envelope protein that is from a virus other than the virus from which the genome is derived. One with skill in the art can choose an appropriate pseudotype for the viral delivery system used and cell to be targeted. In addition to conferring a specific host range, a chosen pseudotype may permit the virus to be concentrated to a very high titer. Viruses alternatively can be pseudotyped with ecotropic envelope proteins that limit infection to a specific species (e.g., ecotropic envelopes allow infection of, e.g., murine cells only, where amphotropic envelopes allow infection of, e.g., both human and murine cells.) In addition, genetically-modified ligands can be used for cell-specific targeting.

After production in a packaging cell line, the viral particles containing the antisense or RNAi agent expression cassettes are purified and quantified (titered). Purification strategies include density gradient centrifugation, or, preferably, column chromatographic methods.

In a further embodiment of the invention, expression constructs, vectors, polypeptides, or peptides may be entrapped in a liposome. Liposomes are vesicular structures characterized by a phospholipid bilayer membrane and/or an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and/or entrap water and/or dissolved solutes between the lipid bilayers (Ghosh and Bachhawat, 1991). Also contemplated is an expression construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and/or expression of foreign DNA in cultured chick embryo, HeLa and hepatoma cells.

In certain embodiments of the invention, the liposome may be complexed with a hemagglutinatin virus (HVJ). This has been shown to facilitate fusion with the cell membrane and/or promote cell entry of liposome-encapsulated DNA (Kaneda et al., 1989), for example. In other embodiments, the liposome may be complexed and/or employed in conjunction with nuclear non-histone chromosomal proteins (HMG-1) (Kato et al., 1991). In yet further embodiments, the liposome may be complexed and/or employed in conjunction with both HVJ and HMG-1. In other embodiments, the delivery vehicle may comprise a ligand and a liposome.

In another embodiment of the present invention, the direct introduction of a JAB1 inhibiting protein ligand into a diseased tissue is contemplated to provide a therapeutic effect. Such a JAB1 inhibiting ligand may be identified by the screening methods of the present invention described herein. This therapeutic method comprises administering to a subject a therapeutic composition which comprises a JAB1 inhibiting ligand in amount effective to decrease JAB1-mediated biological activity in the subject. In specific embodiments, polypeptide or peptide compositions are delivered in liposomes.

In one embodiment, a polypeptide for use in such a JAB1 inhibiting ligand composition comprises no more than about 100 amino acid residues, preferably no more than about 60 residues, more preferably no more than about 30 residues. Peptides may be considered as having fewer than about 30 residues and can be linear or cyclic. Additionally, the JAB1-inhibiting ligand can be in any of a variety of forms of peptide derivatives, that include amides, conjugates with proteins, cyclized peptides, polymerized peptides, analogs, fragments, chemically modified peptides, and the like derivatives.

C. Pharmaceutical Compositions

Pharmaceutical compositions of the present invention comprise an effective amount of one or more JAB1-inhibiting agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one JAB1-inhibiting agent or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards. As used herein, the term "JAB1-inhibiting agent" refers to an agent that modulates, such as by reducing, expression of JAB1 or that inhibits the activity of a JAB1 polypeptide, such as by inhibiting binding of JAB1 to a target, including p27.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The JAB1-inhibiting agent may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, mouthwashes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

Any of the JAB1 inhibiting ligands of the present invention may be used in the form of a pharmaceutically acceptable salt or inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Alternatively, suitable bases capable of forming salts may be used with the peptides of the present invention and include inorganic bases such as sodium hydroxide, ammonium hydroxide, potassium hydroxide and the like; and organic bases such as mono- di- and tri-alkyl and aryl amines (e.g. triethylamine, diisopropyl amine, methyl amine, dimethyl amine and the like), and optionally substituted ethanolamines (e.g. ethanolamine, diethanolamine and the like).

A JAB1 inhibiting ligand of the present invention can be synthesized by any of the techniques that are known to those skilled in art. If the ligand is a polypeptide, synthetic chemistry techniques, such as a solid-phase Merrifield-type synthesis, are preferred for reasons of purity, antigenic specificity, freedom from undesired side products, ease of production and the like.

The JAB1 inhibiting ligands and/or gene therapy vectors as described above are adapted for administration as a pharmaceutical compositions. Formulation and dose preparation techniques have been described in the art, for example, those described in U.S. Pat. No. 5,326,902 issued to Seipp et al; U.S. Pat. No. 5,234,933 issued to Marnett et al.; and PCT Publication WO 93/25521 of Johnson et al., the entire contents of each of which are herein incorporated by reference.

The therapeutic agents of the present invention may be administered systemically or parenterally, for example. The doses to be administered are determined depending upon age, body weight, symptom, the desired therapeutic effect, the route of administration, the nature of the therapeutic agent and the duration of the treatment etc. In a human adult, the doses per person per administration are generally between 1 mg and 500 mg, by oral administration, up to several times per day, and between 1 mg and 100 mg, by parenteral administration up to several times per day. Since the doses to be used depend upon various conditions, as mentioned above, there may be a case in which doses are lower than or greater than the ranges specified above.

A composition of the present invention that is to be administered parenterally typically is in dosage unit formulations containing standard, well-known nontoxic physiologically acceptable carriers, adjuvants, and vehicles as desired. The term "parenteral" as used herein includes intravenous, intramuscular, intra-arterial injection, or infusion techniques. Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed in conjunction with the therapeutic agents are water, Ringer's solution, and isotonic sodium chloride solution. In addition, sterile, fixed oils are conventionally employed as a solvent or suspending medium. For this purpose any bland, fixed oil can be employed including synthetic mono- or di-glycerides. In addition, fatty acids such as oleic acid find use in the preparation of injectables. Preferred carriers include neutral saline solutions buffered with phosphate, lactate, Tris, and the like.

Solid compositions for oral administration include compressed tablets, pills, dispersible powders, capsules, and granules. In such compositions, one or more of the active substance(s) is or are, admixed with at least one inert diluent (lactose, mannitol, glucose, hydroxypropylcellulose, microcrystalline cellulose, starch, polyvinylpyrrolidone, magnesium metasilicate alminate, etc.). The compositions may also comprise, as is normal practice, additional substances other than inert diluents: e.g. lubricating agents (magnesium stearate, etc.), disintegrating agents (cellulose, calcium glycolate etc.), and agents that assist in dissolving (glutamic acid, aspartic acid, etc.) or stabilizing (lactose etc.). The tablets or pills may, if desired, be coated with gastric or enteric material (sugar, gelatin, hydroxypropylcellulose or hydroxypropylmethyl cellulose phthalate, etc.). Capsules include soft ones and hard ones.

Liquid compositions for oral administration include pharmaceutically-acceptable emulsions, solutions, suspensions, syrups and elixirs. In such compositions, one or more of the active substance(s) is or are admixed with inert diluent(s) commonly used in the art (purified water, ethanol etc.). Besides inert diluents, such compositions may also comprise adjuvants (wetting agents, suspending agents, etc.), sweetening agents, flavoring agents, perfuming agents and preserving agents. Other compositions for oral administration include spray compositions which may be prepared by known methods and which comprise one or more of the active substance(s). Spray compositions may comprise additional substances other than inert diluents: e.g. preserving agents (sodium sulfite, etc.), isotonic buffer (sodium chloride, sodium citrate, citric acid, etc.). For preparation of such spray compositions, for example, the method described in U.S. Pat. No. 2,868,691 or 3,095,355 may be used.

In further embodiments, the present invention may concern the use of a pharmaceutical lipid vehicle compositions that include a JAB1-inhibiting agent, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the JAB1-inhibiting agent may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In addition, the JAB1 inhibiting ligands and/or gene therapy vectors of the present invention may be used in combination with other treatment modalities, such as chemotherapy, surgical intervention, cryotherapy, hyperthermia, radiation therapy, and the like.

VI. Transgenic Animals

It is also contemplated to be within the scope of the present invention to prepare a transgenic non-human animal that expresses JAB1. The term "transgene" refers to exogenous genetic material which does not naturally form part of the genetic material of an animal to be genetically altered but can be incorporated into the germ and/or somatic cells of that animal by standard transgenic techniques. The term "transgenic" refers to cells, tissues, embryos, fetuses or animals which carry one or more transgenes. The term "chimeric" refers to an embryo, fetus or animal which consists of two or more tissues of different genetic composition.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), the entire contents of each of which are herein incorporated by reference.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

JAB1 and p27 Expression Profiles in Breast Tumors

Breast tumor samples were obtained from a study group of 53 women with invasive breast carcinoma. The women were 35 to 90 years old and had a mean age of 63.2±13.3 years and a median age of 65. None of the women had a family history of breast cancer. The patients had not undergone any chemotherapy or radiotherapy before surgery. Patient selection was based on the availability of archived paraffin blocks for immunohistochemical studies, which are described below. Six cases (11%) were stage I, 28 (53%) were stage II, 13 (25%) were stage III, and 6 (11%) were stage IV. Five tumors (9%) were grade 1, 29 (55%) were grade 2, and 19 (36%) were grade 3. The tumors were surgically staged according to the American Joint Committee on Cancer's tumor-nodes-metastasis system and graded according to the Nottingham modification of the Bloom-Richardson system. All of tumors excepted for one had a maximum diameter larger than 1 cm. 47 of the breast cancer carcinomas were ductal carcinomas, 3 were lobular carcinomas, and 3 were mixed invasive carcinomas. The cut-off level for considering a tumor estrogen- or progesterone-receptor positive was 10 fmol/mg.

Consecutive sections were cut from each tumor specimen and processed for immunohistochemical analysis with the LSAB+ kit available from DAKO as described below. The following monoclonal antibodies were used in the immunohistochemical analysis of the tumor sections: JAB1 antibody from clone 4D11D8, available from Zymed, San Francisco, Calif., at a dilution of 1:400; p27 antibody from DAKO clone SX53K8, available from DAKO, Carpinteria, Calif., at a dilution of 1:200; and a Ki-67 antibody, MIB-1, available from Immunotech, Westbrook, Me., at a dilution of 1:100. The specificity of the JAB1 antibody was tested in normal tonsil tissue samples by competition with a specific JAB1 peptide and a non-specific peptide.

The sections from the tumor specimens were fixed in buffered formalin and embedded in paraffin. 5-μm thick paraffin-embedded sections were mounted on poly-L-lysine-coated slides, dewaxed in xylene, rehydrated in a graded series of ethanol, and incubated for 15 minutes with 0.3% hydrogen peroxide. For the unmasking of the JAB1 and p27 antigens, the sections were incubated in plastic Coplin jars containing preheated target retrieval solution, Dako Catalog #S1699, and heated for 35 minutes in a household vegetable steamer (Model Sunbeam 4713/5710, 900 W, available from Sunbeam-Oster) and allowed to cool at room temperature for at least 15 minutes. After incubation in endogenous protein blocking solution, Dako Catalog #X0909, the sections were incubated with the monoclonal antibodies at the aforementioned dilutions at 4° C. overnight. The sections were washed three times with pH 8.0 TBS/0.05% Tween-20 for 5-10 minutes. The sections were then incubated with biotin-conjugated secondary antibody, Dako Catalog #K0690, for 30 minutes at room temperature. The sections were then incubated with streptavidin-horseradish peroxidase complex, Catalog #K0690, for 20 minutes. 3,3-diaminobenzidine tetrahydrochloride (DAB) was used as the chromogen and hematoxylin was used as the counterstain, according the LSAB+ kit instructions. To eliminate false-positive staining, i.e., background staining, a control assay was performed in which each immunostaining-assay step was sequentially eliminated. Tissue sections stained with immunoglobulin G isotype, available from Dako, were used as negative controls in all immunostainings.

Evaluation of all immunostained slides was performed independently by a pathologist who counted at least 1000 tumor cells in 10 representative high-power fields. Epithelial cells of the adjacent normal breast ducts were used as internal positive controls for JAB1 and p27 expression. Cells were considered JAB1-positive when nuclear staining of JAB1 protein was detected, and cells were considered p27-positive when nuclear staining of p27 protein was detected. Serial tissue sections from the same areas of the breast were used to examine JAB1, p27, and Ki-67 protein expression levels. Ki-67 was used as a marker of cell proliferation. The proliferation index (PI) was defined as the percentage of MIB-1-positive tumor cells. Breast tumors in which 50% or greater of the cells assayed had a detected level of JAB1 protein were described as high JAB1 protein breast tumors, while breast tumors in which less than 50% of the cells assayed had a detectable level of JAB1 protein were described as low JAB1 protein breast tumors.

Table 1 shows characteristics of the high JAB1 protein breast tumors and of the low JAB1 protein breast tumors.

TABLE 1

| Tumor Characteristics | Low JAB1 expression (n = 21) | | High JAB1 expression (n = 32) | | P value |
|---|---|---|---|---|---|
| | Number | % | Number | % | |
| Histologic Type | | | | | |
| Ductal Carcinoma | 18 of 47 | 38 | 29 of 47 | 62 | 0.7[1] |
| Lobular carcinoma | 2 of 3 | 67 | 1 of 3 | 33 | |
| Mixed | 1 of 3 | 33 | 2 of 3 | 67 | |
| Grade | | | | | |
| 1 | 1 of 5 | 20 | 4 of 5 | 80 | 0.2[1] |
| 2 | 10 of 29 | 34 | 19 of 29 | 66 | |
| 3 | 10 of 29 | 53 | 9 of 19 | 47 | |
| Stage | | | | | |
| I | 2 of 6 | 33 | 4 of 6 | 67 | 0.2[1] |
| II | 9 of 28 | 32 | 19 of 28 | 68 | |
| III | 7 of 13 | 54 | 6 of 13 | 46 | |
| IV | 3 of 6 | 50 | 3 of 6 | 50 | |
| Lymph - node metastasis | | | | | |
| Positive | 16 of 34 | 47 | 18 of 34 | 53 | 0.15[2] |
| Negative | 5 of 19 | 26 | 14 of 19 | 74 | |
| Estrogen Receptor Status | | | | | |
| Positive | 14 of 33 | 42 | 19 of 33 | 58 | 0.3[2] |
| Negative | 2 of 10 | 10 | 8 of 10 | 80 | |
| Progesterone Receptor Status | | | | | |
| Positive | 10 of 27 | 37 | 17 of 27 | 63 | >0.9[1] |
| Negative | 6 of 16 | 38 | 10 of 16 | 62 | |

[1]Chi-square test
[2]Fisher's exact test

JAB1 was detected in 43 (81%) of the 53 breast tumors. In 37 of the JAB1-positive tumors, JAB1 was predominantly found in the nucleus, although weak cytoplasmic immunoreaction was also observed in some cells. In the other 6 JAB1-positive tumors, JAB1 was predominantly found in the cytoplasm, with weaker nuclear immunoreactivity. The percentage of JAB1-positive tumor cells ranged from 20% to 98%, with a mean of 65.6%±24.5 and a median of 70%. Thirty two (60%) of the 53 tumors showed high JAB1 protein expression. JAB1 was not associated with the proliferation index. Non-cancerous breast cells were also tested for the expression of JAB1 protein. JAB1 was detected in about 10 to 30% of non-cancerous breast cells, including ductal epithelial cells in proximate normal and hyperplastic breast tissues.

p27 protein expression was examined in 49 of the breast tumors included in this study. The percentage of cells assayed in breast tumor cells with detected p27 protein ranged from 0.1% to 85%, with a mean±s.d. of 33.5%±24.5% and a median of 34.1%. p27 protein was also expressed in the nuclei of nearby normal epithelial, myoepithelial, and stromal cells. Breast tumors in which 50% or greater of the cells assayed had a detected level of p27 protein were described as high p27 protein breast tumors, while breast tumors in which less than 50% of the cells assayed had a detected level of p27 protein were described as low p27 protein breast tumors. High p27 protein expression was found in 13 (27%) of the 49 carcinomas.

Table 2 summarizes the relationship between JAB1 protein levels and p27 protein levels in the 49 breast tumors. The Mann-Whitney U test and Fisher's exact test were used in the statistical analysis. An average of 27.2% of the breast tumor cells examined in high JAB1 protein tumors had a detected level of p27, while an average of 44.5% of the breast tumor cells examined in low JAB1 protein tumors had a detected level of p27 (P=0.02, Mann-Whitney U test). Of the 31 tumors that were high JAB1 protein tumors, 26 of the tumors were low p27 protein tumors. Thus, it appears that a high JAB1 protein level is correlated with a low p27 protein level in breast tumors.

TABLE 2

| | JAB1 level | | |
|---|---|---|---|
| | High | Low | P value |
| p27 LI | | | |
| (mean % ± SD) p27 expression | 27.2 ± 23.2 | 44.5 ± 23.2 | 0.02[1] |
| High | 5 | 8 | 0.04[2] |
| Low | 26 | 10 | |

[1]Mann-Whitney U test
[2]Fisher's exact test

Example 2

Survival Rates

The available clinical data on the survival rate of the female patients with breast carcinomas discussed above was examined and is summarized in FIGS. 1A and 1B. FIG. 1B shows that a significant difference in overall survival rates was found between women with breast tumors that had a detected level of JAB1 protein and women with breast tumors that did not have a detected level of JAB1 protein. As defined herein, the "5-year overall survival rate" is the percentage of surviving patients five years after the patients' treatment or cancer diagnosis. The 5-year survival rate includes patients that have experienced relapses or cancer progression. After an average of 70 months, there was a 69% 5-year overall survival rate among the women with breast tumors that had a detected level of JAB1 protein, while there was a 100% 5-year overall survival rate among the women with breast tumors that did not have a detected level of JAB1 protein. In addition, there was also a difference in progression-free survival rates between women with breast tumors that had a detected level of JAB1 protein and women with breast tumors that did not have a detected level of JAB1 protein.

"Progression-free survival rate" is the percentage of survivors whose breast cancer had not progressed since the patients' treatment or cancer diagnosis, which was about five years earlier, in this case. There was an 80% 5-year progression-free survival rate among the women with breast carcinomas that had a detected level of JAB1 protein, while there was a 100% 5-year progression-free survival rate among the women with breast tumors that did not have a detected level of JAB1 protein. As all of the women (that were studied over the five year period) that did not have detected JAB1 protein in their breast tumors at the beginning of the period survived and did not experience cancer progression, while of the women that had detected JAB1 protein in their breast tumors, 31% did not survive and 20% of the survivors experienced breast cancer progression, testing a breast tumor sample for JAB1 protein expression provides a method of prognosticating a survival rate after a specified period of time of a patient having breast cancer. Furthermore, testing a breast tumor sample for JAB1 protein provides a method of prognosticating a progression-free survival rate after a specified period of time. The methods of prognosticating survival rates may further include measuring or estimating an amount of JAB1 protein in the sample.

Example 3

High JAB1 Expression is Directly Proportional to HER-2 Expression

JAB1 protein levels were examined in eight pairs of non-cancerous and cancerous breast tissue samples from eight of the patients of Example 1. The samples were obtained in a biopsy. The samples were washed twice in cold 1×PBS that was diluted from 10×PBS, (Catalog #M6505, available from Fisher) and lysed at 4° C. in lysis buffer (25 mM Hepes, pH 7.7, 400 mM NaCl, 0.5% Triton X-100, 1.5 mM $MgCl_2$, 2 mM EDTA, 2 mM DTT, 0.1 mM PMSF, protease inhibitors [including the following protease inhibitors at the following final concentrations: leupeptin 10 µg/ml, peptstatin 2 µg/ml, antipain 50 µg/ml, aprotinin 2 µg/ml, chymostatin 20 µg/ml, and benzamidine 2 µg/ml] and phosphatase inhibitors [including the following phosphatase inhibitors at the following final concentrations: 50 mM NaF, 0.1 mM $Na_3VO_4$, and 20 mM β-glycerophosphate]). Aliquots of cell lysates containing about 70 mg of total protein were run on 10-12% SDS-PAGE, transferred to polyvinylidene difluoride membranes (Immobilon-P Transfer Membrane, Catalog #IPVH00010, available from Millipore of Bedford, Mass.), and probed with primary polyclonal antibodies to JAB1, available from Zymed, p27 antibodies available from BD-Pharmingen, San Diego, Calif., and to HER-2, available from Neomarkers of Fremont, Calif., all at 1:1000 dilutions. Goat anti-mouse IgG (H&L)-HRP conjugate, Catalog #1706516, available from Bio-Rad of Hercules, Calif. was used as the secondary antibody for p27 and HER-2. HRP-protein A, Catalog #NA9120, from Amersham of Piscataway, N.J. was used as the secondary antibody for JAB1. An enhanced chemiluminescence (ECL) kit, Catalog #RPN2106, available from Amersham Pharmacia, Piscataway, N.J. was used to detect the proteins. Vinculin or β-actin antibodies, available from Sigma Chemical Co., St. Louis, Mo., served as internal positive controls for the immunoblots.

Figure 2A:
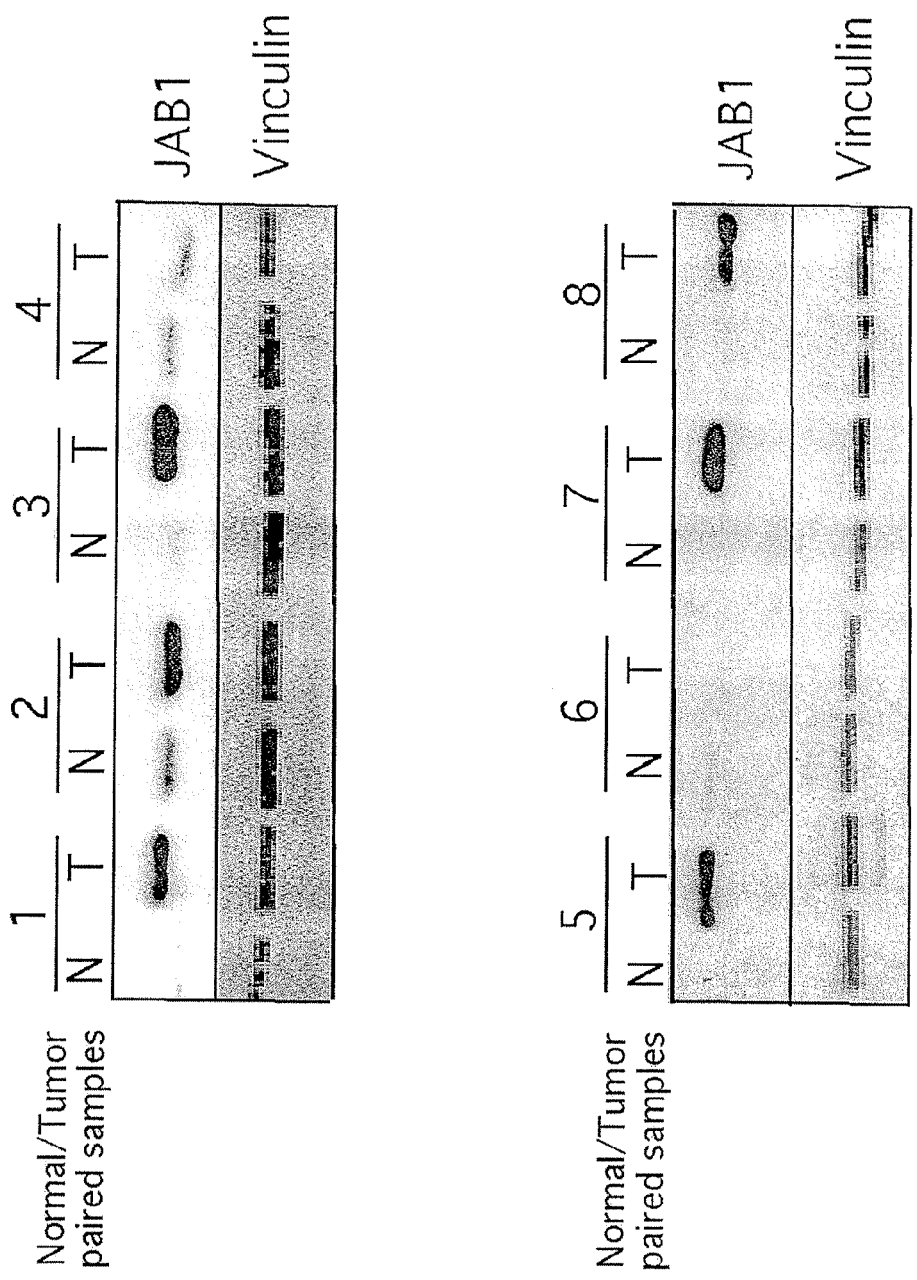
FIG. 2A shows JAB1 and p27 expression in normal breast tissue and breast tumors. Western blots of paired samples of noneoplastic breast tissue (N) and tumor tissue (T) immunoblotted against JAB1 or vinculin (used as a loading control). JAB1 and p27 expression in normal breast tissue and breast tumors. Western blots of paired samples of noneoplastic breast tissue (N) and tumor tissue (T) immunoblotted against JAB1, and HER2, with vinculin used as a loading control.
Figure 2B:
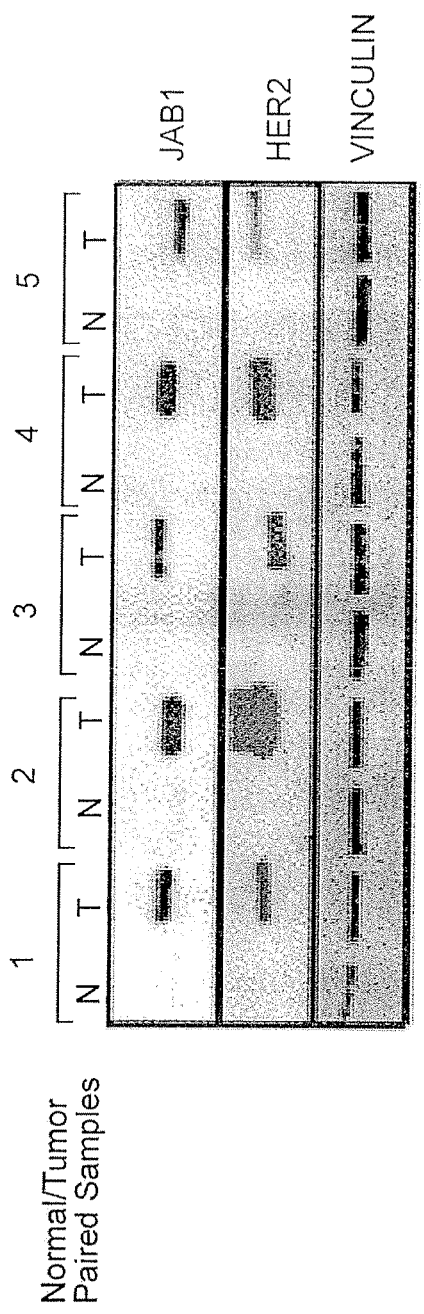
FIG. 2B shows JAB1 and p27 expression in normal breast tissue and breast tumors. Western blots of paired samples of noneoplastic breast tissue (N) and tumor tissue (T) immunoblotted against JAB1, and HER2, with vinculin used as a loading control.

The results of the western blots for the pairs of non-cancerous and cancerous breast tissue samples revealed that JAB1 protein levels were significantly higher in the cancerous breast tissue samples than in the non-cancerous breast tissue samples (FIG. 2A). It was also found that the level of JAB1 protein in the cancerous breast tissue was directly proportional to the amount of HER-2 protein in paired cancerous breast tissue samples (FIG. 2B). HER-2 is a receptor tyrosine kinase that is often copy number amplified and/or overexpressed in human cancers, including breast cancer (see, Hung, et al., *Gene* 159:65-71 (1995), Slamon, et al, *Science* 244:707-712 (1989), Berchuk, et al., *Cancer Res.* 50:4087-4091 (1990)). Overexpression of HER-2 has been associated with tumor aggressiveness (Slamon, et al, *Science* 235:674-7 (1987)) and poor prognosis in breast cancer (Varley, et al., *Oncogene* 1:423-30 (1987)).

Example 4

Regulated Expression of JAB1 Affects Expression of p27

Four human breast cancer cell lines were used to examine the effect of ectopic expression of JAB1 in breast cancer cells. The following four breast cancer cell lines were used: BT-474, MDA-MB-468, MDA-MB-231, and BT-549, all of which are available from the ATCC. The BT-474 cells were cultured in Dulbeccos' minimal Eagle medium supplemented with 10% fetal calf serum and 1% penicillin-streptomycin, and the MDA-MB-468, MDA-MB-231, and BT-549 cells were cultured in RPMI-1640 supplemented with 10% fetal calf serum and 1% penicillin-streptomycin. The cell lines were incubated at 37° C. in a humidified atmosphere containing 5% $CO_2$.

The cell lines were transduced with a recombinant adenovirus vector expressing a doxycycline-regulated (Tet-Off) form of JAB1. The presence of doxycyline represses the expression of JAB1 by the vector, while the absence of doxycycline allows the overexpression of JAB1 by the vector. The recombinant vector was constructed using the Adeno-X Tet-Off Expression System, Catalog #K1651-1, available from Clontech, Palo Alto, Calif., according to the manufacturer's recommendations. The full-length cDNA encoding for human JAB1, an exemplary sequence which may be found at the National Center for Biotechnology Information's GenBank database Accession number U65928 (SEQ ID NO:8), was fused to a C-terminal Myc epitope tag by introducing an Xba I site 1129 nucleotides downstream fro the JAB1 ATG and inserting the EcoR1/Xba I fragment of the JAB1 cDNA into an EcoR1/Xbu I digested pcDNA3.1-Myc.His vector, Catalog #V800-20, available from Invitrogen, Inc., Carlsbad, Calif. A BamH1I site and an Afl II site were introduced at the ends of the JAB1-Myc sequence, and the resulting BamH1/Afl II fragment was inserted into the BamH1/Afl II restriction sites of the pTRE-shuttle vector to generate a pTRE-JAB1-Myc construct.

Figure 3:
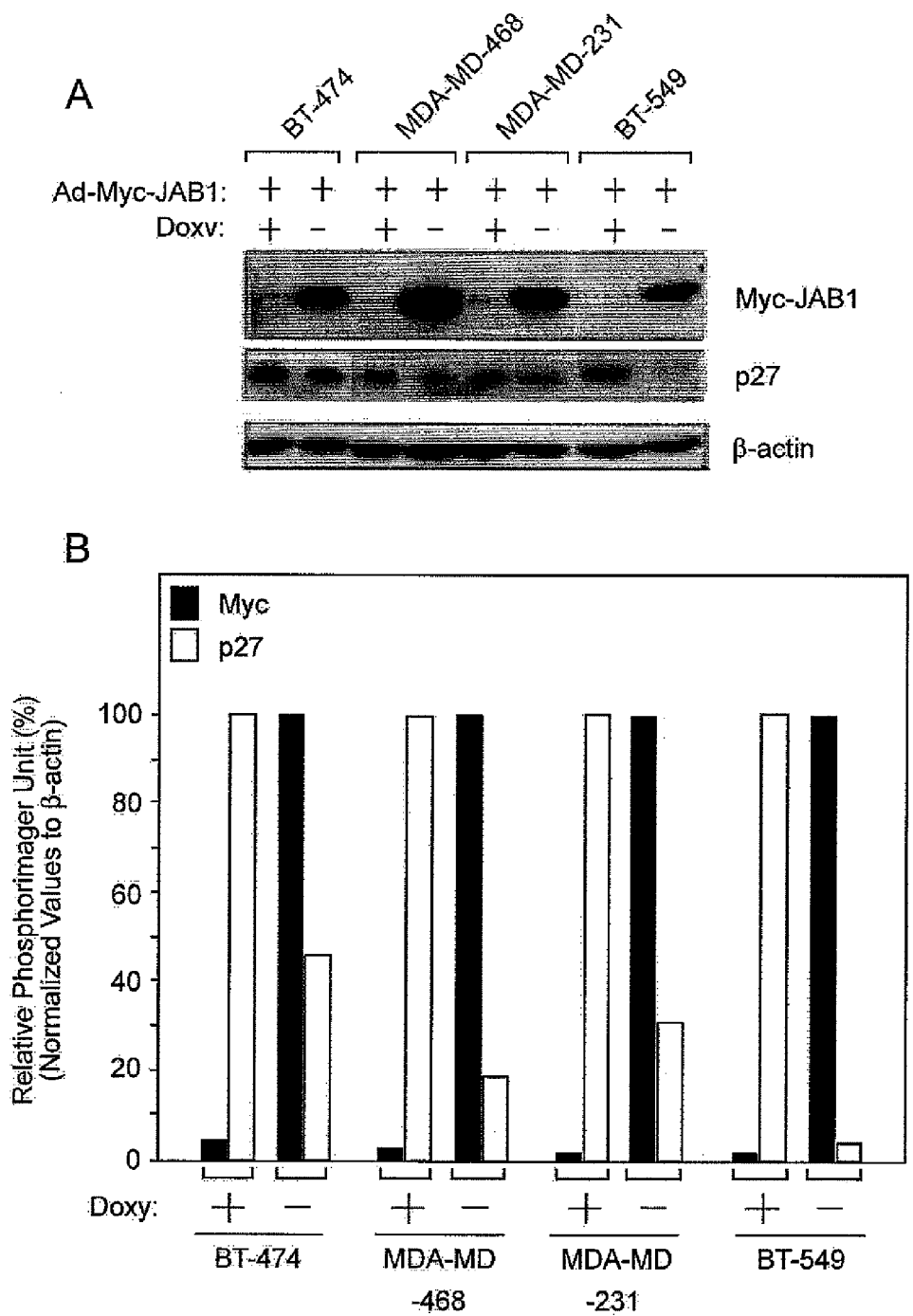

The PI-SceI and I-Ceu I digestion product of the pTRE-JAB1-Myc shuttle vector was cloned into a pAdeno-X Viral DNA vector via ligation. Recombinant infectious adenoviruses were then produced by transfecting HEK (human embryonic kidney) 293 cells with pAdeno-X-JAB1-Myc viral DNA. Successful transfection was confirmed by detecting synthesis of a JAB1-Myc fusion protein by immunoblotting with anti-Myc antibodies. Adenoviruses were collected from the cells by centrifugation of the cell culture medium from the plates at 1200 rpm for 10 minutes. Recipient cells from the breast cancer cell lines BT-474, MDA-MD-468, MDA-MD 231, and BT-549 that had been plated 12 to 24 hours before infection were then co-transfected with a regulatory virus, adeno-X Tet-Off, and the Ad-JAB1-Myc virus at a multiplicity of infection of 50 in the presence or absence of 1 μg/ml doxycycline, a tetracycline analogue, in a tetracycline-free serum medium, Catalog #8630-1, available from Clontech, Palo Alto, Calif. After 48 hours, cell lysates from the transfected cells were prepared as described in Example 3, and immunoblotting was performed as described in Example 3. Anti-Myc antibodies were used to detect the JAB1-Myc fusion protein and anti-p 27 antibodies were used to detect p27 protein. β-actin antibodies were used as a loading control. Protein amounts were quantified by PhosphorImager analysis. FIG. 3A shows the western blot and FIG. 3B shows the quantitative results from a western blot demonstrating that the breast cancer cell lines transfected with the Ad-JAB1-Myc construct produced high levels of Myc-JAB1 protein in the absence of doxycycline, and that p27 protein levels decreased when high levels of Myc-JAB1 protein were produced. Thus, it appears that high levels of JAB1 in breast cancer cells result in reduced levels of p27 protein in breast cancer cells.

Example 5

Tumor Induction in Mice

Figure 4:
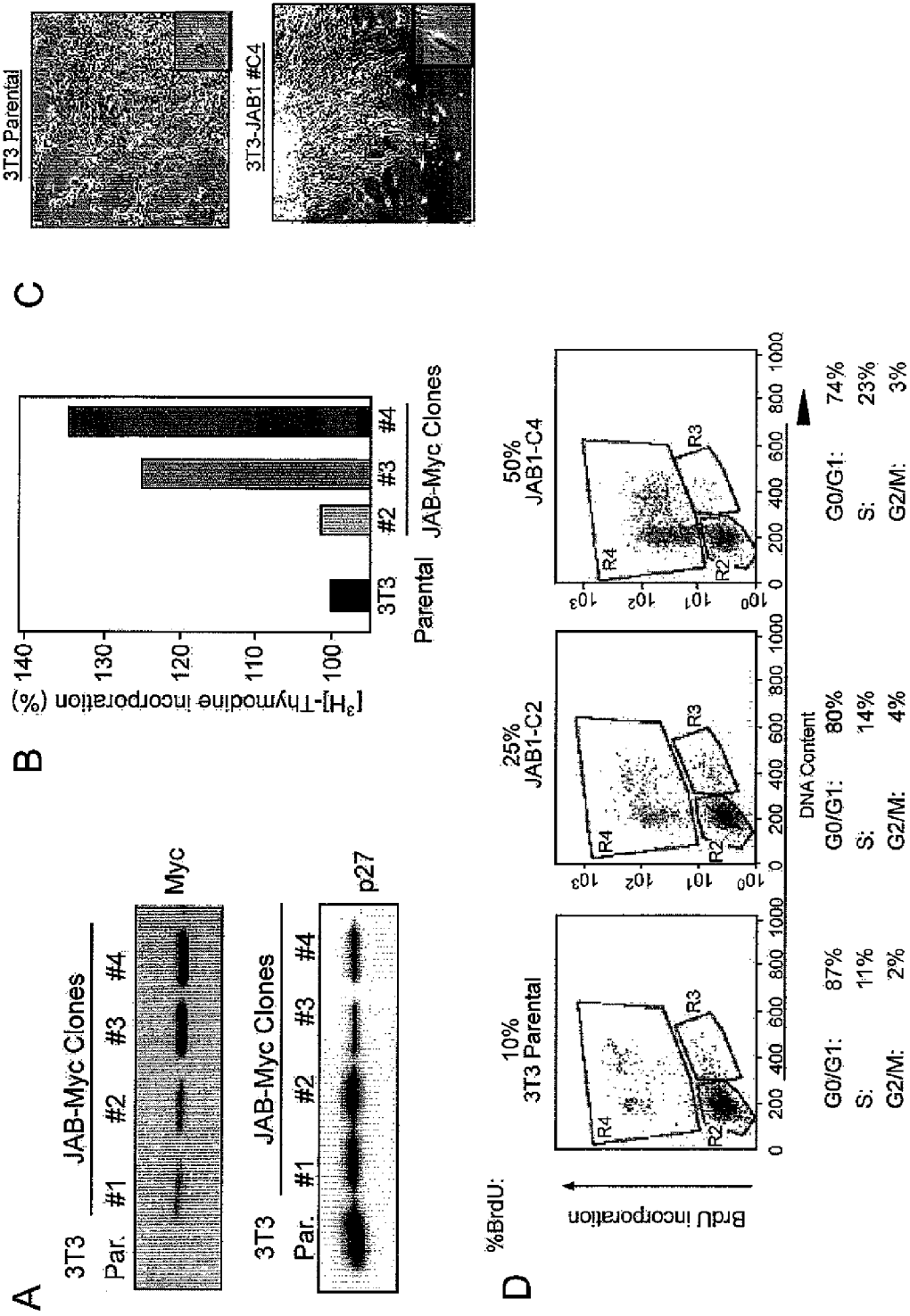
FIGS. 4A-4I show an exemplary in vivo mouse tumor model wherein JAB1 promotes cell cycle progression through S-phase and induces tumorigenesis.
Figure 4:
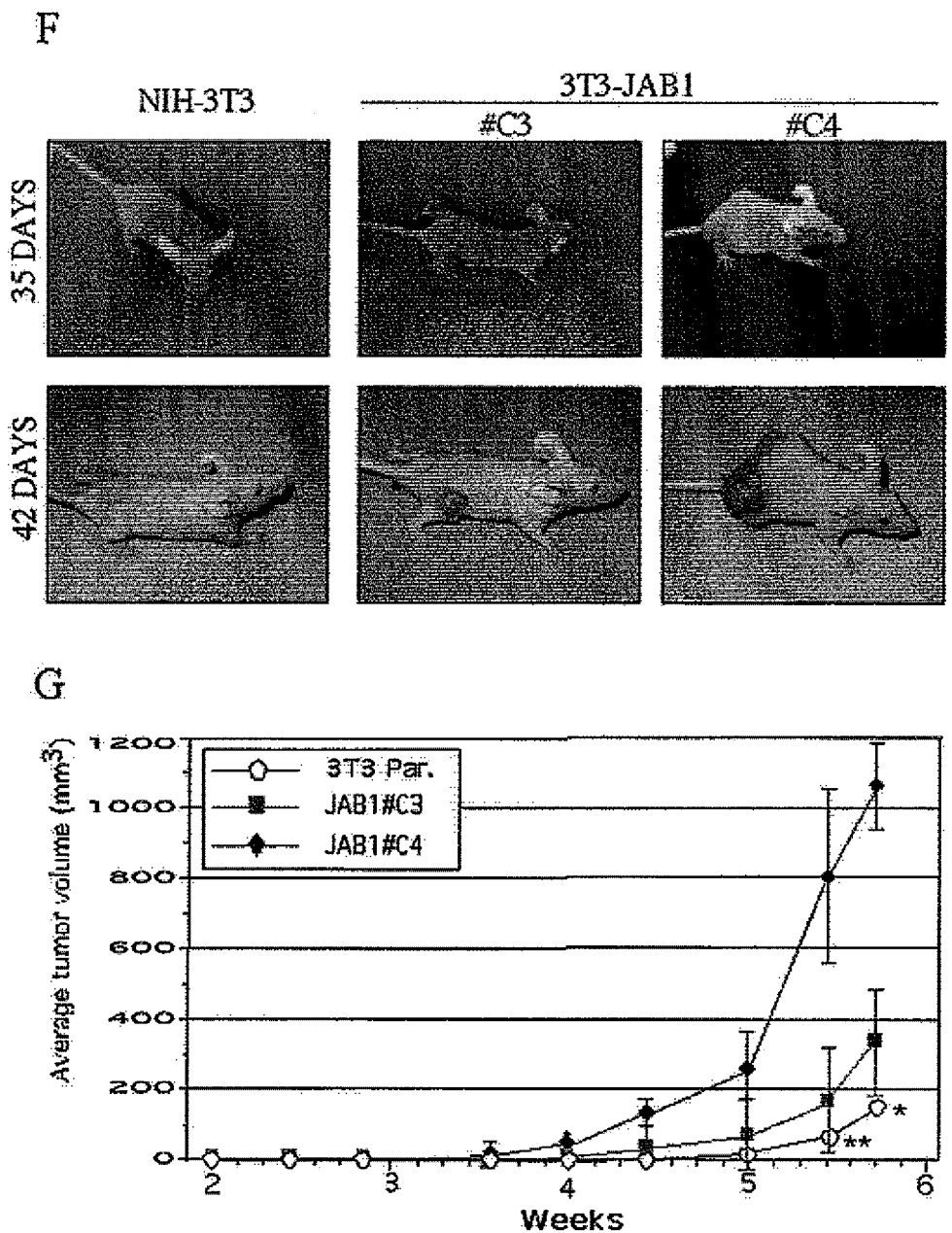
Figure 4:
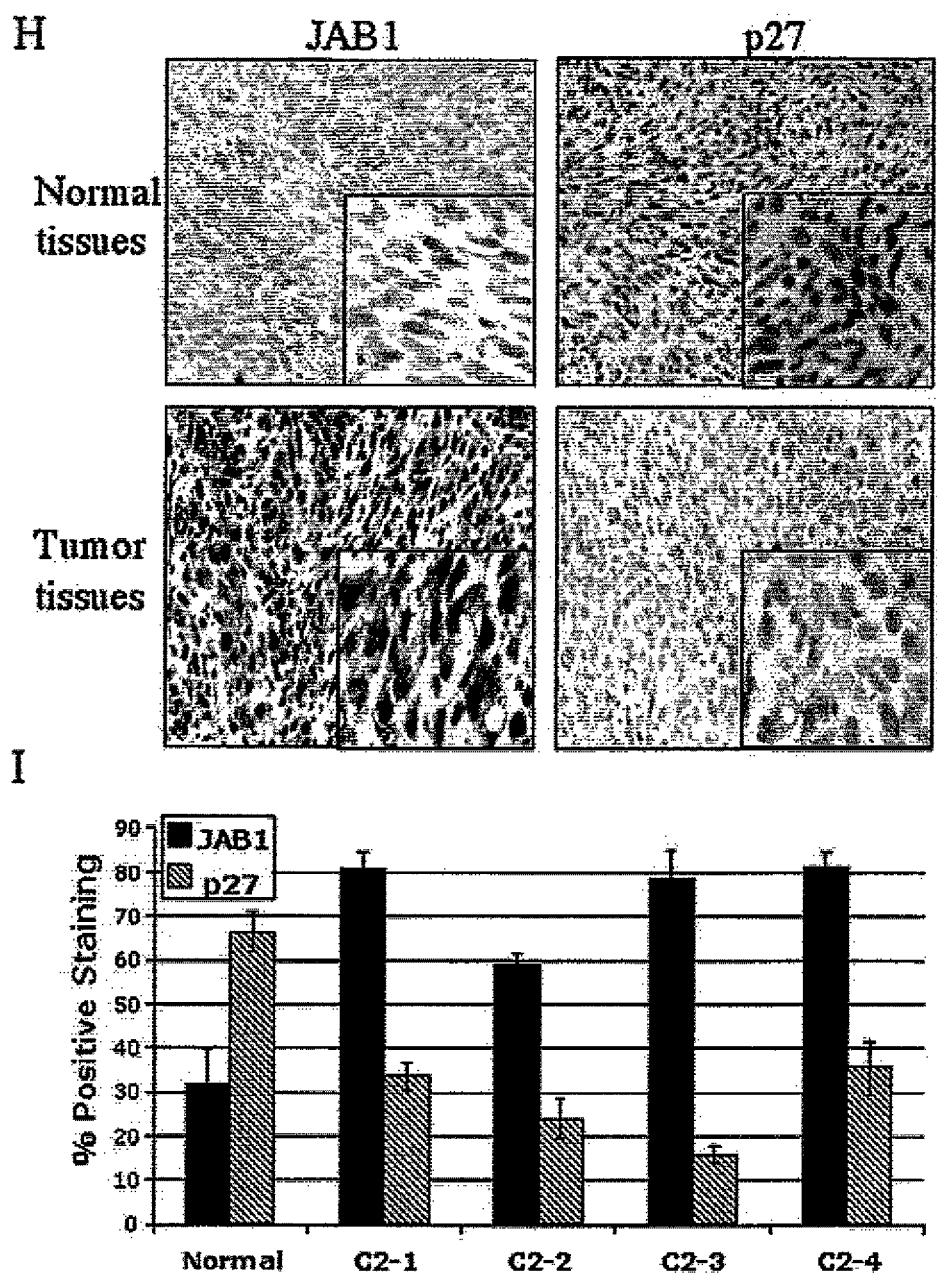

The activity of the Ad-JAB1-Myc virus was also studied in NIH3T3 cells transfected with the Ad-JAB1-Myc virus and in mice that were injected with the transfected NIH3T3 cells. The NIH3T3 cells were transfected using the method described above for the transfection of the HeLa cells, and western blots were performed on the cell lysates of four transfected cell lines, JAB-myc clones #1-4. FIG. 4A shows the results of the western blots. JAB-myc clones #3 and #4 expressed a high level of Myc-JAB1 protein and a low level of p27 protein.

In addition, it was found that the stable expression of Myc-JAB1 in 3T3 cells increased cellular proliferation as measured by [$^3$H]-thymidine incorporation. As can be seen in FIG. 4B, the increase in thymidine incorporation was directly proportional to the expression of exogenous Myc-JAB1 in the various stable clones. For thymidine incorporation, $1\times10^5$ cells of each Myc-JAB1 clone and the parental 3T3 cells were plated in six wells of a 24-well plate. After 24 hours, the media was changed to serum-free DMEM and incubated at 37° C. for 24 hours. The media was aspirated and replaced with DMEM containing serum and 1 mCu/ml [$^3$H]-thymidine (Amersham Biosciences, Piscataway, N.J.), and incubated at 37° C. for 1 hour. Cells were washed twice sith PBS and solubilized in 200 mM NaOH. Counts per minute were determined in a Liquid Scintillation Beta Analyzer (Packard Instruments Co., Meridan, Conn.).

Additionally, morphology of parental NIH-3T3 cells and NIH-3T3-JAB1C#4 were observed (FIG. 4C). NIH-3T3-JAB1C#4, expression high levels of Myc-JAB1, exhibited morphologic transformation compared to the control cells. The NIH-3T3-JAB1C#4 cells were spindle-shaped and displayed highly refractile morphology, with long protrusions and pseudopodia. In other experiments, exogenous JAB1 expression was found to promote S-phase cell cycle progression as measured by bromodeoxyuriding (BrdU) incorporation and propidium iodide (PI) staining, the results of which can be seen in FIG. 4D. The parental cells and stable clones were serum starved and labeled with BrdU for 45 minutes. The cells were then stained with fluorescent anti-BrdU antibodies and PI for flow cytomety analysis.

The JAB-myc clones #3 and #4 experienced the formation of a large number of colonies after 1 or 2 weeks of growth on soft agar, as shown in Table 3 and in FIG. 4E.

TABLE 3

| Cells | Soft-agar growth | Average no. of colonies/ dish at 1 week; at 2 weeks | | No. of cells injected in mice | Tumors >10 mm in diameter by 42 days |
|---|---|---|---|---|---|
| 3T3 Parental (Control) | − | 0 | 0 | $4\times10^6$ | 0/5 |
| 3T3 JAB1#C3 | + | 145 | 227 | $4\times10^6$ | 3/5 |
| 3T3 JAB1#C4 | +++ | 165 | 336 | $4\times10^6$ | 9/10 |

Figure 5:
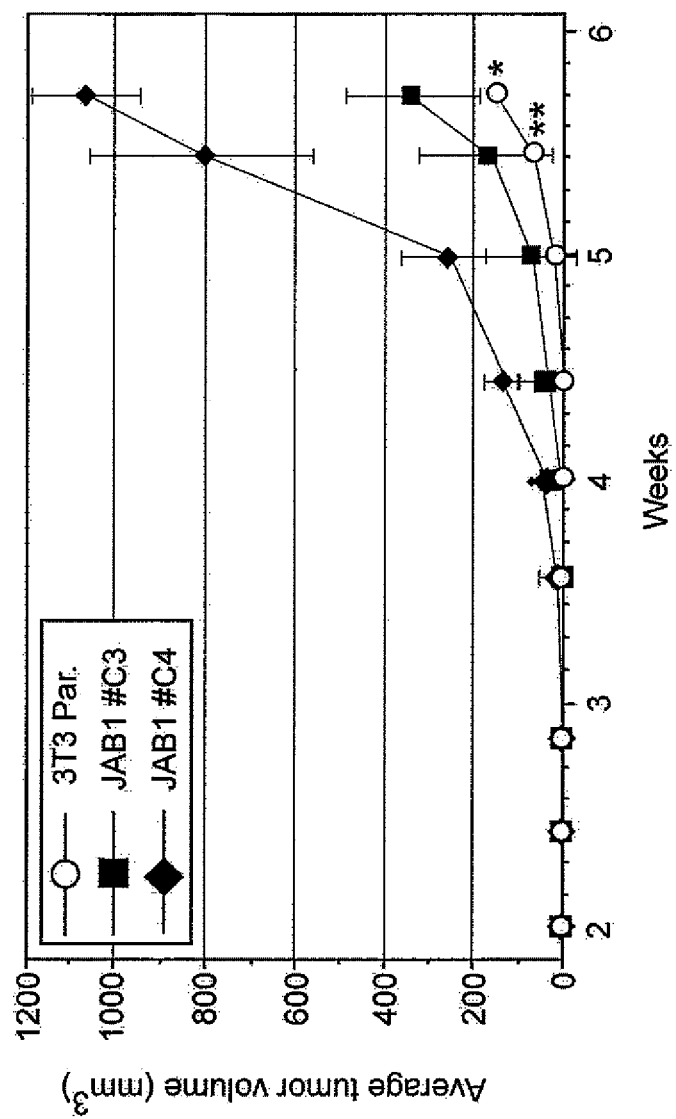
FIG. 5 is a plot of average tumor volume vs. time for JAB1 expression-induced tumors in nude mice.

Approximately 4×10⁶ NIH3T3 cells, JAB-myc clone #3 cells and JAB-myc clone #4 cells were separately injected into 5 nude mice each. The results are summarized in FIG. 5. None of the mice injected with NIH3T3 cells had developed tumors by 40 days after the injections; however, the mice injected with JAB-myc clone #3 cells developed tumors averaging greater than 350 mm³ in volume and the mice injected with JAB-myc clone #4 cells developed tumors greater than 1000 mm² in diameter. FIG. 4F demonstrates that exogenous JAB1 expression induced tumorigenesis in nude mice. Stable clones, #C3, C4 and control cells (NIH-3T3) were injected s.c (6×10⁶ cells) into 6-week old female nude mice (BALB/C). 5 mice were used for each cell line. After 35 days mice developed tumors>10 mm only with clones C3 and C4 but not with control injected clone. Pictures of each mice are shown at 35 and 42 days post-injection. FIG. 4G shows JAB1 expression promotes tumor development in nude mice. Mice were injected as in FIG. 4F, and tumor formation was scored weekly.

In addition, immunostaining for JAB1 and p27 was performed in both normal and cancerous tissues in these mice. Mice-bearing JAB1 tumors were isolated and paraffin-embedded tissue section sere obtained and stained with monoclonal antibodies for JAB1 or p27 and counterstained with hemotoxylin. In FIG. 4H, results showed low JAB1 expression and high p27 expression in normal tissue, while the inverse was seen in tumor tissues. FIG. 4I is a column chart summarizing this data. 300 positive and negative cells were counted in each of three fields for JAB1 and p27 in normal and four tumor tissue samples, and the percent positive staining for each is shown.

Example 6

Figure 6:
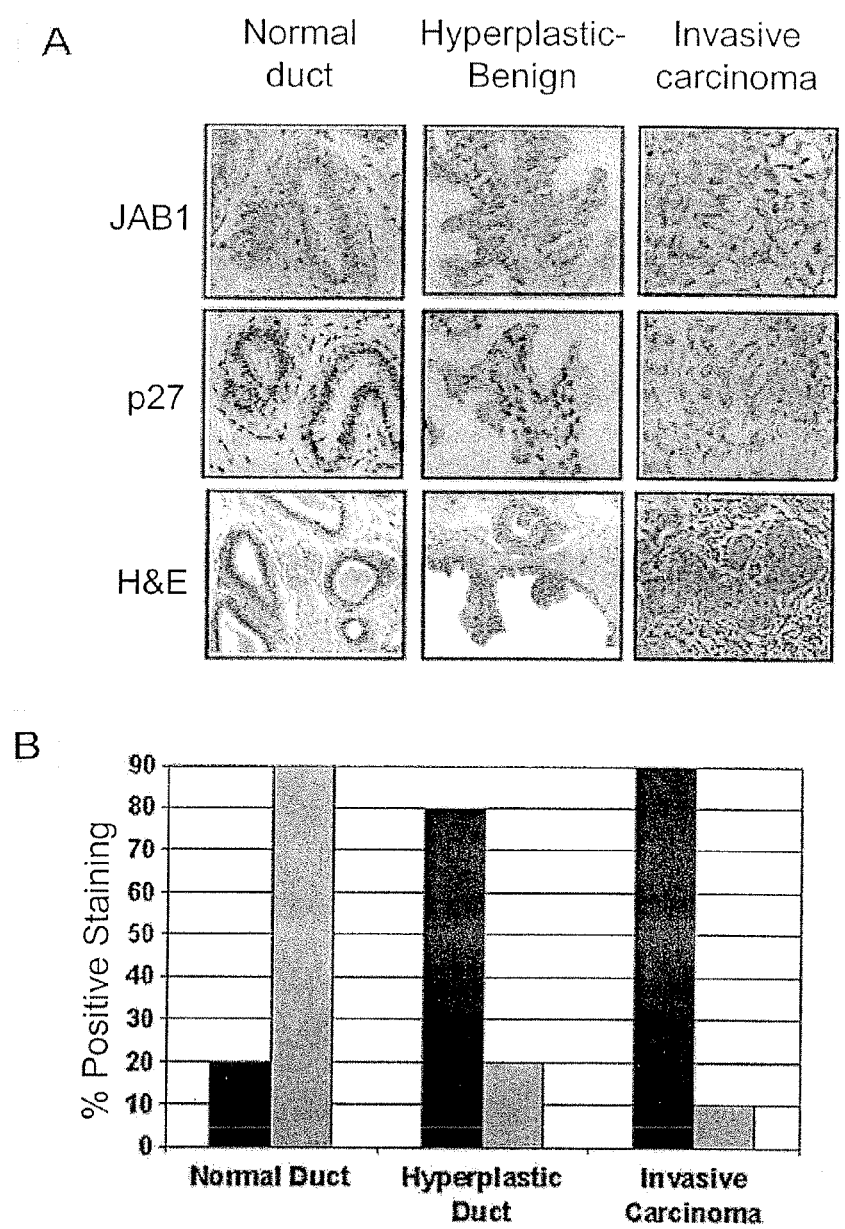
FIGS. 6A and 6B show JAB1 and p27 levels in normal, hyperplastic-benign and invasive-neoplastic lesions of human breast tissue samples. JAB1 levels increase with tumorigenicity, correlating with a decrease in p27.

JAB1 and p27 Levels in Normal, Hyperplastic-Benign and Invasive-Neoplastic Lesions of Human Breast Tissue Samples JAB1 levels increase with tumorigenicity, correlating with a decrease in p27. In FIG. 6A, immunohistochemical staining of a breast tumor progression array for JAB1 and p27. JAB1 levels are low in normal tissue and increase with tumorigenesis. In FIG. 6B, percent of cells staining positive for either JAB1 or p27 were quantified and graphed.

Example 7

JAB1 Expression in Anaplastic Large Cell Lymphomas

Lymph tumor and reactive lymph node tissues samples were obtained from a study group of 66 patients with systemic ALCL. The diagnosis of ALCL was based on morphological and immunohistologic criteria as specified by the WHO classification. Consecutive sections were cut from each sample and processed for immunohistochemical analysis as described below. The clinicopathological features of the patients are described in Rassidakis, et al., *Am. J. Pathol.* 159:527-535 (2001), which is incorporated by reference herein.

Consecutive sections were cut from each tumor specimen and processed for immunohistochemical analysis with the LSAB+ kit available from DAKO as described below. The following monoclonal antibodies were used in the immunohistochemical analysis of the tumor sections: JAB1 antibody from clone 4D11D8, available from Zymed, San Francisco, Calif., at a dilution of 1:400; p27 antibody from DAKO clone SX53K8, available from DAKO, Carpinteria, Calif., at a dilution of 1:200; and a Ki-67 antibody, MIB-1, available from Immunotech, Westbrook, Me., at a dilution of 1:120. The specificity of the JAB1 antibody was tested in a competition study by using a specific JAB1 peptide at a concentration of 100 μM and an unrelated peptide to stain full tissue sections of two normal tonsils and two reactive lymph nodes. The specific JAB1 peptide used was identical to the one used for the production of the JAB1 monoclonal antibody. Competition of the specific JAB1 peptide with the JAB1 antibody resulted in a lack of JAB1 immunostaining in control slides.

The sections from the tumor specimens were fixed in buffered formalin and embedded in paraffin. 5-μm thick paraffin-embedded sections were mounted on poly-L-lysine-coated slides, dewaxed in xylene, and rehydrated in a graded series of ethanol. Sections were placed in plastic Coplin jars containing preheated target retrieval solution available from Dako, heated in a household vegetable steamer (Model Sunbeam 4713/5710, 900 W, available from Sunbeam-Oster) and allowed to cool at room temperature for at least 15 minutes. The following steps were performed on the sections using the DAKO Autostainer at room temperature: blocking with 3% hydrogen peroxide in PBS, pH 7.4 for 5 minutes; blocking using protein blocking solution available from DAKO for 5 minutes; incubation with the monoclonal antibodies for 1 hour; incubated with the secondary biotinylated antibody, Dako Catalog #K0690, for 30 minutes at room temperature; and developed with the streptavidin/horseradish peroxidase complex of the LSAB+ kit for 20 minutes at room temperature. The sections were then incubated with streptavidin-hyperoxidase complex. 3,3-diaminobenzidine tetrahydrochloride (DAB), available from Biogenex, San Ramon, Calif., was used as the chromogen and hematoxylin was used as the counterstain, according the LSAB+ kit instructions.

Tissue sections from normal tonsil were used as external positive controls for p27, JAB1, and MIB-1 immunostaining. Reactive small lymphocytes in all tissue sections served as internal positive controls for each antibody. Slides stained with normal rabbit serum, available from DAKO, without primary antibody were used as negative controls.

Expression of JAB1 and p27 was evaluated in at least 1,000 tumor cells. Cells were considered JAB1-positive when nuclear staining of JAB1 protein was detected, and cells were considered p27-positive when nuclear staining of p27 protein was detected. p27 was detected mostly in the mantle and marginal zones of reactive lymphoid follicles. The highly proliferating germinal center cells were almost all p27 negative.

In ALCLs, the percentage of tumor cells having detected p27 protein in the nucleus varied from 0 to 82.6% with a mean±SD of 9.3±19.6% and a median of 0.8%. p27 was localized principally in the nucleus of tumor cells with variable staining intensity. 12 (82%) of the tumors were p27-positive, i.e., tumors that had detected p27 protein in greater than 10% of the tumor cells examined, while 44 (81.8%) of the tumors were p27-negative, i.e., tumors that had detected p27 protein in 10% or less of the tumor cells examined. Of the 12 p27-positive ALCLs, 5 were anaplastic lymphoma kinase (ALK)-positive, and 7 were ALK negative (P=0.7, Fisher's exact test). ALK overexpression is often found in ALCLs, and is associated with a favorable clinical outcome. p27 expression was not statistically associated with clinical and laboratory features. In a subset of 20 ALCLs (8 ALK-positive and 12 ALK-negative), 3 were p27-positive, and 17 were p27-negative.

As almost 89% of the tumors had a high detected level of JAB1 protein, it is believed that testing a lymph tissue sample for the presence and amount of JAB1 protein, as described above with respect to breast tissue, may provide a method of diagnosing or prognosticating the development of lymphoma.

JAB1 was detected in a large number of germinal center cells as well as a number of lymphocytes in interfollicular areas. JAB1 immunoreactivity was predominantly localized in the nucleus of lymphocytes, but a weaker cytoplasmic reaction was also observed in a variable number of lymphocytes.

The percentage of tumor cells having detected JAB1 protein in the nucleus ranged from 0 to 100% with a mean of 70.8±29.7% and a median of 85%. 47 of 53 (88.7%) tumors were JAB1-positive, i.e., tumors that had detected JAB1 protein in greater than 10% of the tumor cells examined, while 6 (11.3%) of the tumors were JAB1-negative, i.e., tumors that had detected JAB1 protein in 10% or less of the tumor cells examined. Of the 47 JAB1-positive tumors, 15 were ALK-positive, and 32 were ALK-negative (P>0.9, Fisher's exact test). JAB1 expression (>10% positive tumor cells) was inversely associated with p27 expression. More specifically, 40 of 47 (85.1%) JAB1-positive tumors were p27 negative, and 4 of 6 (66.7%) JAB1-negative tumors were p27 positive (P=0.01 by Fisher's exact test).

p27 protein expression in the tumors was significantly correlated with a lower 5-year survival rate and a lower 5-year progression-free survival rate. The 5-year survival rate of patients having p27-positive tumors was 45.7%, while the 5-year survival rate of patients have p27-negative tumors was 90.1%. The 5-year progression-free survival rate of patients having p27-positive tumors was 39.5%, while the 5-year progression-free survival rate of patients having p27-negative tumors was 66.8%.

p27 protein expression in the tumors was inversely related to JAB1 protein expression in the tumors. 85.1% of the JAB1-positive tumors were p27-negative tumors and 66.7% of the JAB1-negative tumors were p27 positive.

The relationship between p27 and JAB1 protein expression in ALCL was further examined by performing western blots on 5 ALCL cell lines. Two of the cell lines had a detected level of p27 protein and little or no detected JAB1 protein, where two other cell lines had a detected level of JAB1 protein and little or no detected p27 protein. One other cell line expressed a low level of p27 protein and a high level of JAB1 protein. The results of the western blots are further described in Example 7.

Example 8

Western Blots of Anaplastic Large Cell Lymphoma Cells

Five ALK-positive ALCL cell lines were used to examine the amount of JAB1 protein and p27 protein in ALCL cells. The following cell lines were used: Karpas 299, which was obtained from Dr. M. Kadin, Boston, Mass., SR-786 and SU-SHL-1, which were obtained from DSMZ, Braunschweig, Germany, JB-6, and TS-G$_1$, which was obtained from Dr. D. Jones, Houston, Tex. The cell lines are also available from the ATCC. The cells were cultured in RPMI-1640 supplemented with 1% non-essential amino acids, 10% fetal calf serum from Invitrogen, Corp., Grand Island, N.Y., and 1% penicillin-streptomycin. The cell lines were incubated at 37° C. in a humidified atmosphere containing 5% CO$_2$.

Figure 7:
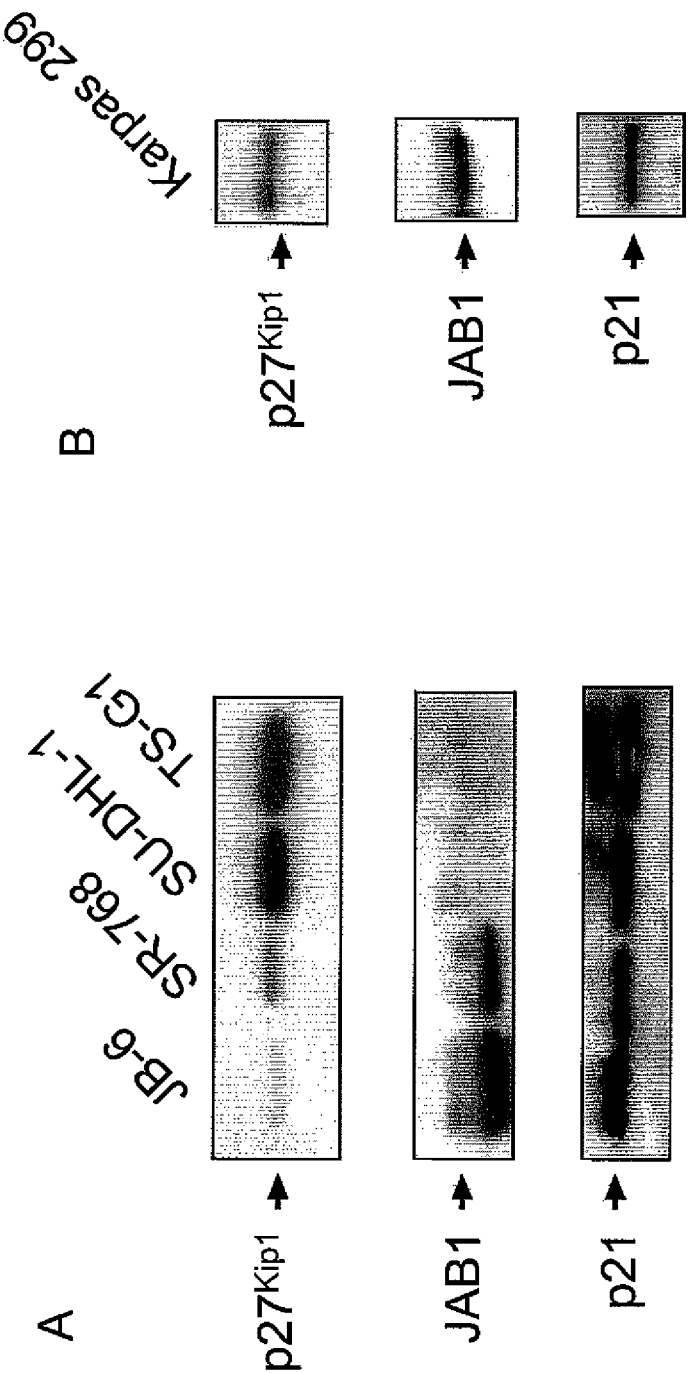
FIGS. 7A and 7B depict a western blot of five exemplary ALCL cell lines, including JB-6, SR-768, SU-DHL-1 and TS-G1 (FIG. 7A) and Karpas 299 (FIG. 7B).

Cell lysates from the ALCL cell lines were prepared and western blots were performed as described in Example 3. The results of the western blots showed that SR-786 and JB-6 cells had a detected level of JAB1 protein and little or no detected p27 protein (FIG. 7). SU-DHL-1 and TG-S1 cells had a detected level of p27 protein and little or no detected JAB1 protein. Karpas 299 cells had a relatively low detected level of p27 protein and a relatively high detected level of JAB1 protein.

Example 9

JAB1 and p27 Expression in a Variety of Cancers

Figure 8:
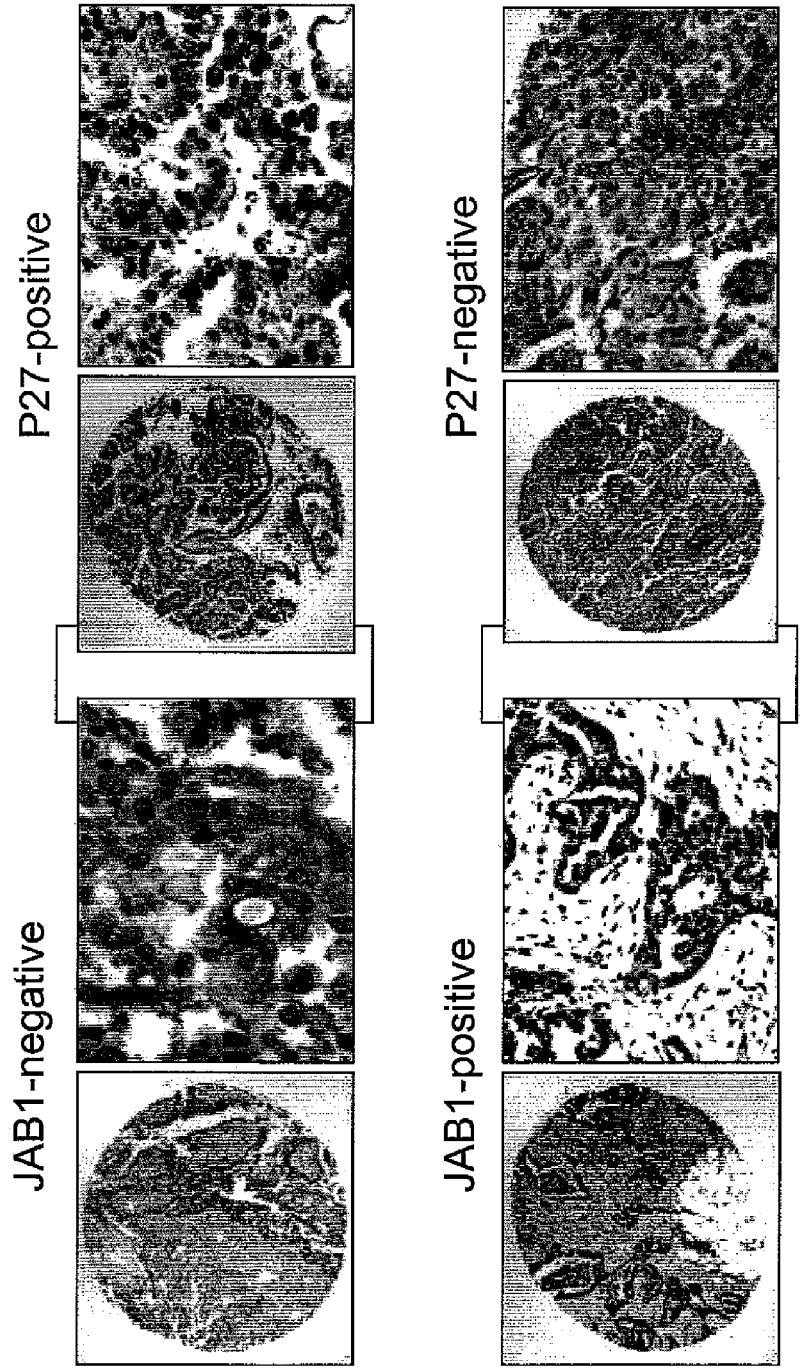
FIG. 8 shows JAB1 and p27 expression in ovarian cancer (tissue array).
Figure 9:
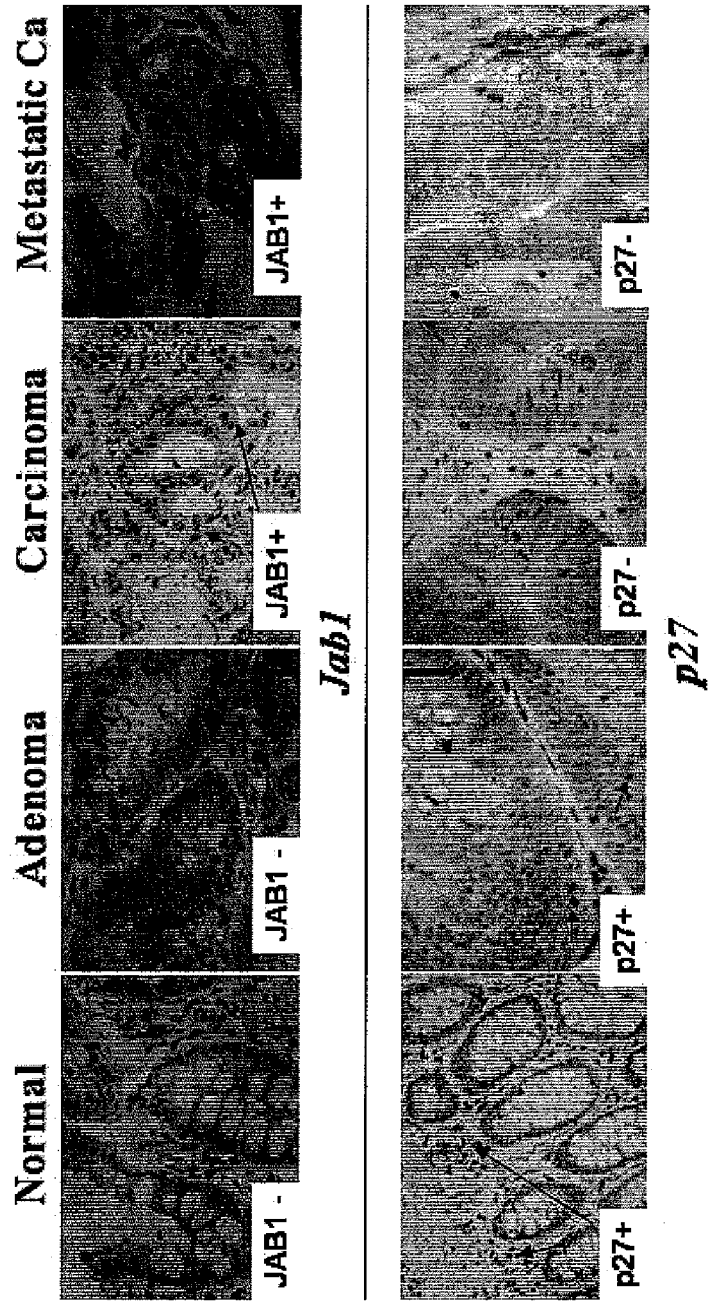
FIG. 9 shows JAB1 and p27 expression in colon carcinoma (tissue array).

In FIGS. 8 and 9, JAB1 and p27 expression is determined in tissue array for ovarian cancer and colon carcinoma, respectively. In FIG. 8, there is immunohistochemical staining with JAB1 and p27 in ovarian cancer. JAB1 is negative in normal case compare to tumor. In FIG. 9, JAB1 expression intensifies with adenoma→carcinoma→metastatic cancer, which indicates that it is a useful marker for identifying stage of disease and progression of cancer.

Example 10

Quantification by ELISA or FISH

Figure 16:
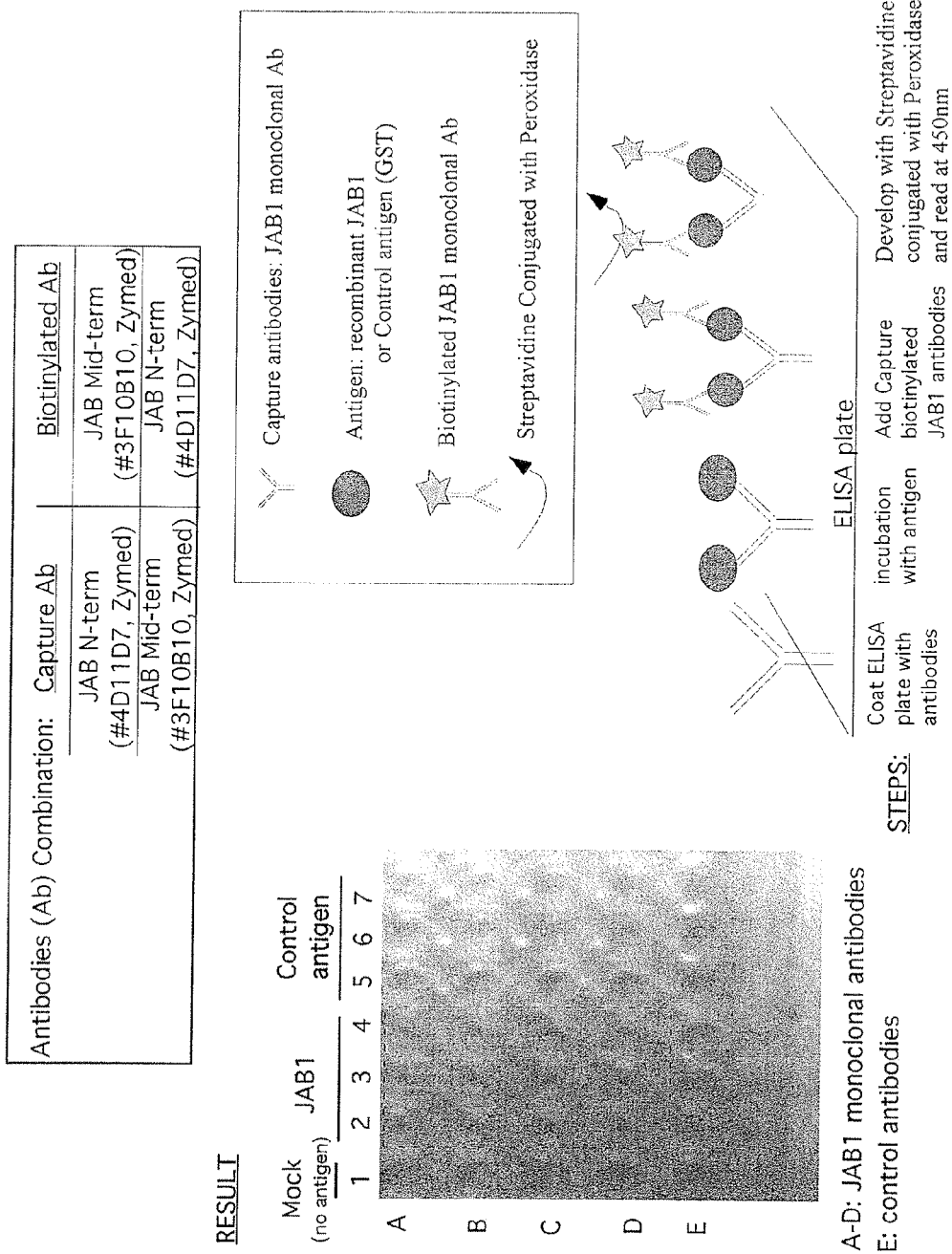
FIG. 16 depicts an exemplary ELISA protocol with JAB1 monoclonal antibodies.

While JAB1 protein may be detected and/or quantitated by immunochemical staining and/or western blots, as described herein, JAB1 protein may be detected and/or quantified by other methods, such as enzyme-linked immunosorbent assays (ELISA) (see, for example, FIG. 16) or fluorescence in situ hybridization (FISH).

ELISA

JAB1 protein was detected using an exemplary ELISA protocol where 100 μL of JAB1 monoclonal antibody at a concentration of 5 μg/μL in sodium bicarbonate buffer (50 mM NaHCO$_3$ pH 9.6) was placed in wells of a 96-well plate (Nunc F96 Maxisorp Immuno plate, Catalog #442404 Batch 059317-3) and was incubated at room temperature for 2 hours. The JAB1 monoclonal antibodies used were Catalog #4D11D7 and #3F10B10, both available from Zymed. The wells were aspirated, and about 200 ul of PBS-T (10 mM PBS with 0.05% Tween-20) was added to each well to wash the wells. The plate was shaken for about 5-10 minutes. The plate was then inverted and shaken to remove the wash buffer. The PBS-T wash protocol was repeated twice more. About 250 μL of SuperBlock Dry Blend Blocking Buffer, Pierce Catalog #37545, diluted with water and having 0.05% Tween-20 was added to each well. The plate was incubated on a shaker for 2 hours at room temperature or at 4° C. overnight. The wells were then washed twice with PBS-T.

100 μL of an antigen, such as GST-JAB1, GST, or serum, was added to the wells. One set of wells received 50 ng/well of antigen, and another set of wells received 400 ng/well of antigen. The plate was then shaken at room temperature for 2 hours. The wells were then washed three times with PBS-T. Biotinylated JAB1 monoclonal antibody, prepared using the Biotintag Micro Biotinylation Kit, Sigma Catalog #S26-36 Lot 91K4876, was diluted to 1:1000 in PBS-T. 100 μL of the biotinylated JAB1 monoclonal antibody was added to each well. The biotinylated JAB1 monoclonal antibodies used were biotinylated Catalog #3F10B10 and #4D11D7, which were used with wells coated with non-biotinylated #4D11D7 and #3F10B10, respectively. The plate was shaken at room temperature for 1 hour. The wells were then washed three times with PBS-T.

Streptavidin Peroxidase Conjugate was then diluted to 1:1000, and 100 μL was added to each well. The plate was shaken at room temperature for 1 hour. The wells were then washed three times with PBS-T. 200 µL of TMB Substrate (3,3',5,5'-Tetramethylbenzidine), Sigma-Aldrich Catalog #T-8665, was then added to the wells. The plate was incubated at room temperature for 30 minutes. The plate was then scanned at 650 nm. Visually, wells containing 50 ng/well of JAB1 antigen had detectable staining, while wells containing 400 ng/well of JAB1 had significantly darker staining. Wells without antigen or with GST antigen had little or no detectable staining.

FISH

JAB1 copy number was studied in healthy human breast tissue by performing FISH on the samples. It is believed that determining JAB1 copy number in cells may provide an estimate of the level of JAB1 protein in cells, as the presence of excess copies of a gene may be correlated with overexpression of the protein encoded by the gene. JAB1 probes were made by nick translation of DNA from BAC clone RP11-92M10, which is publicly available. The DNA was purified from the BAC clones with a Qiagen Maxi Kit, phenol chloroform extracted, precipitated, and resuspended in water. The BRL BioNick Labeling System, Catalog #8247SA was used to perform the nick translation. 10×A4 solution containing 200 µM dATP, 200 µM dGTP, 200 µM dCTP, 500 mM Tris, pH 7.2, 200 mM $MgCl_2$, 100 mM mercaptoethanol, 100 µg/mL BSA, and water was prepared. Then, a reaction mixture of 1 µg of the purified BAC DNA, 5 µL of 10× enzyme mix containing Dnase and Pol I, 5 µL of A4 solution, 1 µL of cy3-dUTP, FITC-dUTP, or alexa-488 dUTP, and distilled water to 50 µL was prepared, mixed, and incubated at 15° C. for about 90 minutes. The reaction was stopped by heating at 75° C. for 15 minutes. A sample of the reaction was run on an agarose gel to confirm that probe fragments of about 300-800 base pairs were generated in the reaction.

The probes were used on 5-µm thick paraffin-embedded sections that were mounted on slides, as described above. The slides were baked at 55-60° C. for 1 to 2 hours. The sections were dewaxed in xylene at room temperature for 3 ten minute incubations. The sections were then washed twice for 10 minutes at room temperature in 100% ethanol. The slides were air dried, and then incubated in preheated fresh 1 M NaSCN at 80° C. for 10 minutes. The slides were then washed twice for 5 minutes in distilled water. Next, the slides were incubated in prewarmed pepsin (1 mg/mL in 0.2 N HCl) for 10 minutes at 37° C., and then washed twice for 5 minutes in distilled water. The slides were then dehydrated at room temperature in 70%, 85%, and 100% ethanol for 3 minutes each. The slides were air dried. The slides were then incubated in prewarmed denaturing solution (70% formamide in 2×SSC) at 74° C. for 5 minutes. The slides were then dehydrated at room temperature in 70%, 85%, and 100% ethanol for 3 minutes each. The slides were air dried.

The slide preparation conditions described above provide only one example of reagent concentrations and processing conditions that may be used. For example, pepsin can be used at a concentration of 100 µg/mL to 4 mg/mL for a time of 5 minutes to 15 minutes. NaSCN may be used at a concentration of 0.1M to 1M for 5 minutes to 30 minutes. The denaturation period can be 2 minutes to 10 minutes.

One hundred ng of a Cy3-labeled locus-specific BAC probe, 100 ng of a FITC-labeled locus specific BAC probe, or 10 µg of human Cot 1 DNA was dissolved in 3 µL of water. 7 µL of Master mix #1 (5 mL formamide, 1 gm dextran sulfate, 1 mL 20×SSC) was added to the 3 µL, and the resulting solution was mixed, denatured at 70-74° C. for 20 minutes, and reannealed at 37° C. for 30 minutes. The solution was added to one of the prepared slides for examining a 20×20 mm area on the slide. A solution containing the chromosome 8-specific probe, CEP 8 DNA probe, Catalog #30-16008 or 32-132008, Vysis Inc., Downers Grove, Ill., was also prepared and added to the slide. The slide was then covered with a plastic coverslip and put in a 50 mL Falcon tube with 100 µL of 50% formamide in 2×SSC. The tube was capped and incubated horizontally with the slide flat in the tube at 37° C. overnight for up to 3 days.

After the incubation, the slides were washed in 3×SSC at 74° C. for 5 minutes. The slides were then washed twice in 4×SSC, 0.1% Triton at 37° C. for 10 minutes. The slides were then washed in 3×SSC at room temperature for 10 minutes. DAPI was added to the slides, and the slides were covered with coverslips and examined using fluorescence microscopy.

Figure 15:
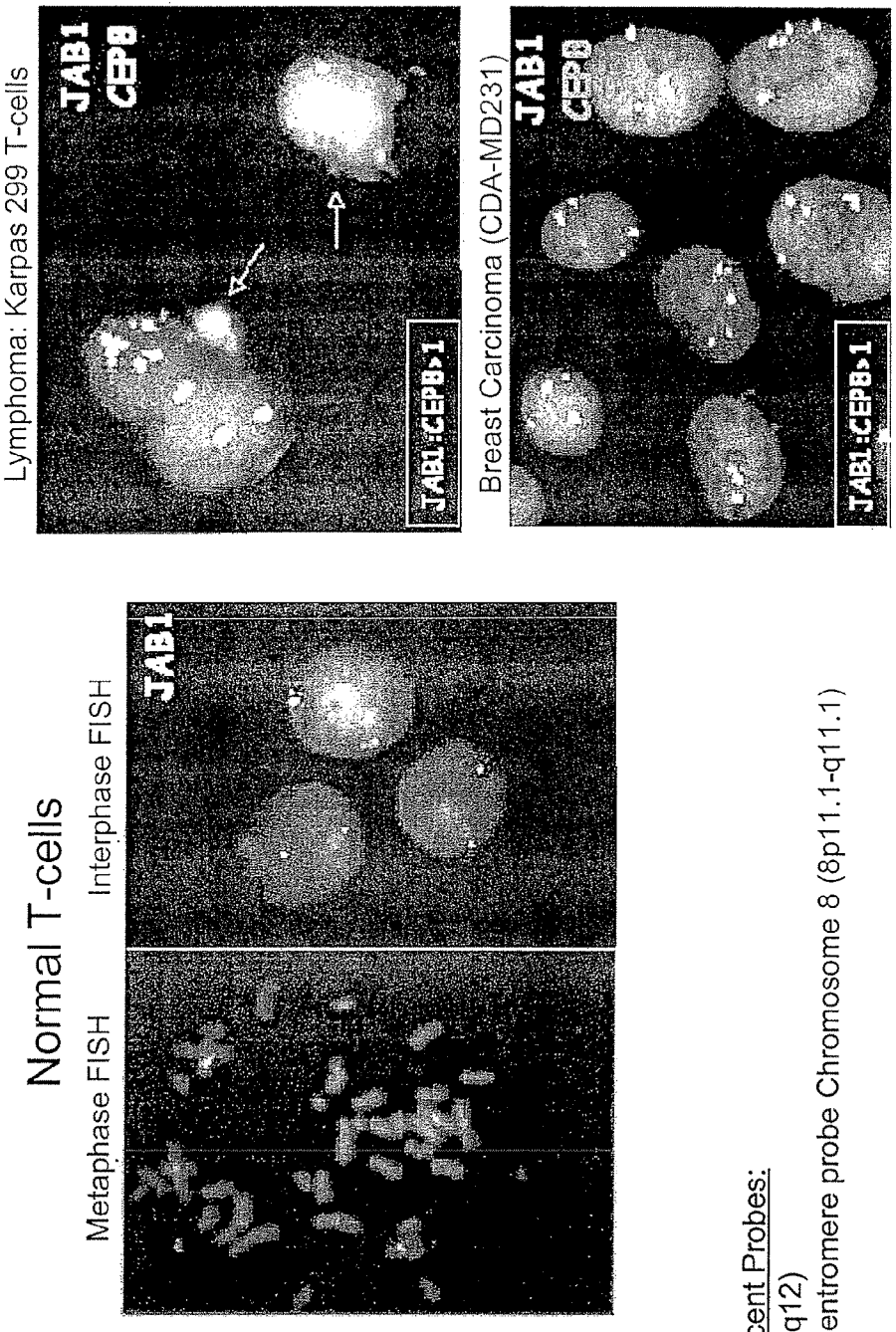
FIG. 15 shows Jab1 amplification in T-cells lymphoma and breast carcinoma. Two-color FISH analysis of Jab1 (green spectrum) and chromosome 8 centromeric (8p11.1-q11.1) (CEP8) (orange spectrum) in lymphoma (Karpas 299 T-cells (top left) and aggressive breast carcinoma (MDA-MD 231 cells) (bottom, left) and compare to normal cells (right). Nuclei were counterstained with 4',6-diamidino-2-phenylindole (blue). Sporadic cancer cells with increased jab1 copy numbers are shown in each case.

JAB1 was successfully visualized on chromosome 8 (FIG. 15). One copy of JAB1 on chromosome 8 was detected in healthy human breast tissue, and multiple copies were detected on Karpas 299 T-cell lymphoma and breast carcinoma cells (MDA-MD 231). The CEP8 centromere probe for chromosome 8 (8p11.1-q11.1) was utilized as a control.

Example 11

Alteration of JAB1 Expression

In view of the high level of JAB1 protein expression in the various, different tumors and cancer cell lines described above, altering the expression of JAB1 in cancer cells thus provides a method for treating some types of cancer. Details for two methods of altering expression are presented in this Example.

JAB1 siRNAs were constructed to study the effect of JAB1 protein down regulation on p27 protein levels. A JAB1 primer pair 5'-TTCAACATGCAGGAAGCTCAG-3' (SEQ ID NO: 1) and 5'-TTCTGAGCTTCCTGCATGTTG-3' (SEQ ID NO: 2) starting at nucleotide 50 downstream from the JAB1 ATG was used with the Silencer™ siRNA Construction Kit (Catalog #1620), available from Ambion of Austin, Tex. according to the manufacturer's instructions to form the double stranded RNA (dsRNA) shown in FIG. 10. HeLa cells that were 30-50% confluent were transfected with 100 nM of JAB1 siRNA or 100 nM of a control siRNA using Oligofectamine™ Reagent, Catalog #12252-011, available from Invitrogen, Carlsbad, Calif., according to the manufacturer's instructions. The control siRNA was made using in the Silencer™ siRNA Construction Kit. The siRNA were diluted in Opti-MEM I media, available from Gibco, before the addition of Oligofectamine™ Reagent. Before the transfection, serum-free and antibiotic-free Dulbeccos' minimal Eagle medium (DMEM) was added to the cells. The siRNA in Oligofectamine™ Reagent was then overlayed on the cells. The cells were incubated for 5 hours at 37° C. in a $CO_2$ incubator. DMEM with 10% serum was added to the cells on top of the siRNA mixture. The transfected cells were harvested 48 hours post transfection and analyzed by western blotting, as described elsewhere herein.

Figure 11:
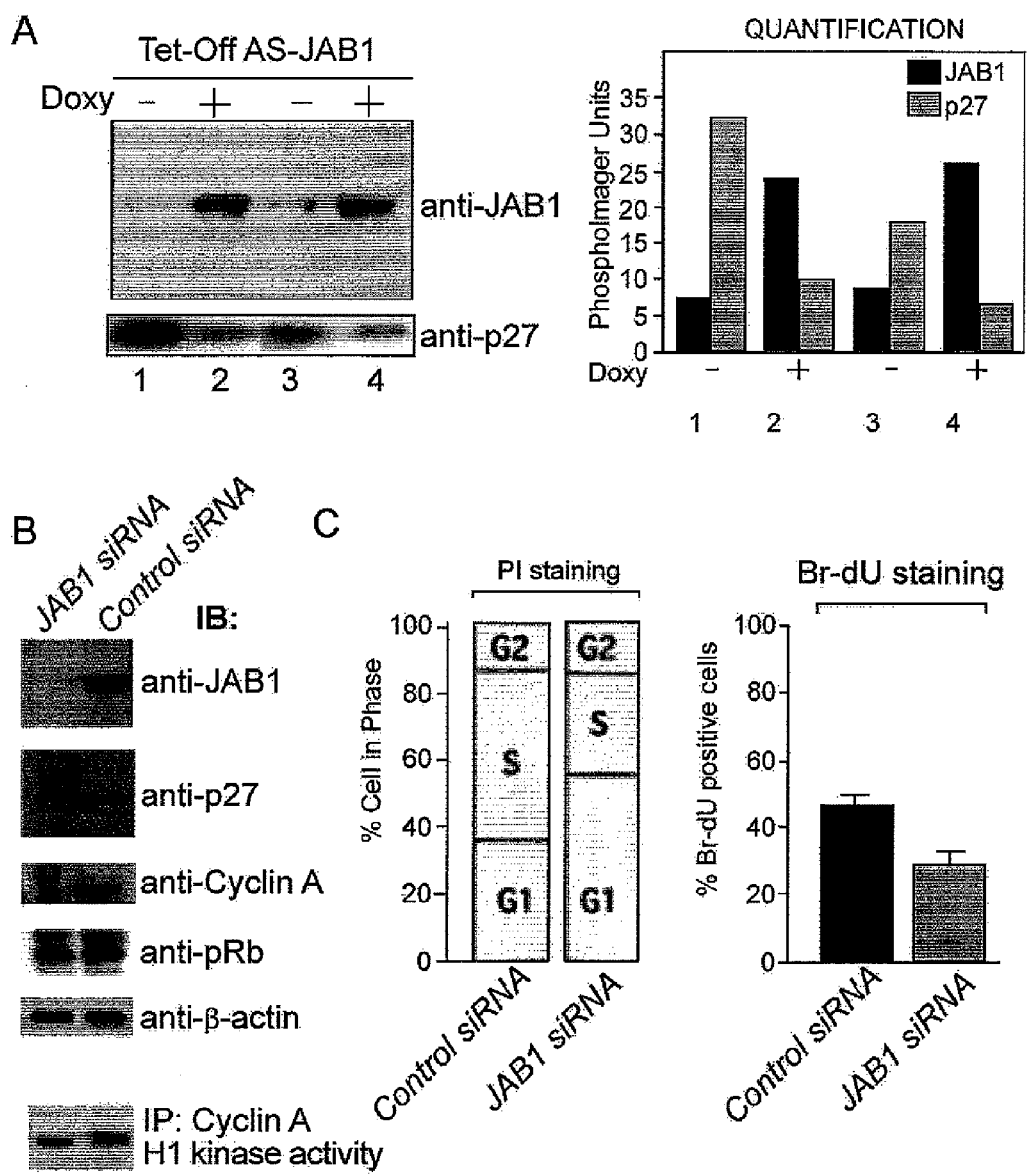
FIGS. 11A-11C show that depletion of endogenous JAB1 with either antisense (AS) or siRNA but not control siRNA, promotes p27-increased stability and leads to G1-arrest.

FIG. 11A shows the results of the western blot. Cell lysates were prepared and subjected to western blotting analysis using anti-JAB1, anti-p27, anti-cyclin, anti-pRb and anti-actin antibodies. For the kinase assay (last panel), cyclin A was immunoprecipitated from cell lysates and analyzed for cyclinA/Cdk-2-associated activity using Histone 1B as a substrate.

FIG. 11B reveals that the knockdown of endogenous JAB1 expression by an JAB1 sequence-related siRNA decreases the S-phase progression in the cell cycle and increases the number of cells in G1 phase. HeLa cells were transfected with JAB1 siRNA and Control siRNA, and progression through the S-phase was measured with anti-BrdU fluorescent antibodies and propidium iodide (PI) staining for flow cytometry analysis.

An antisense JAB1 construct was made to further study the effect of JAB1 protein down-regulation on p27 protein levels. The antisense construct was made by subcloning a 200 base pair fragment of human JAB1cDNA in the antisense orientation into the Hind III site of the vector EC1214A, which is described in Hu, S. X. et al., *Cancer Research* 57: 3339-3343 (1997), and Hu, H. J. et al., *Oncogene* 15: 2589-2596 (1997). EC1214A is a tetracycline/doxycyline-regulated vector that represses the expression of inserted DNA fragments in the presence of tetracycline or doxycycline, and allows the expression of inserted DNA fragments in the absence of tetracycline or doxycycline. The antisense construct was named Tet.AS JAB1. The 200 base pair antisense fragment (SEQ ID NO: 5) includes bases −173 to +73 of the human JAB1 cDNA and was generated by PCR amplification of a JAB1-Myc-His construct. The primers 5'-CACACAAAGCTTGAATTC-CCAAGAGTCTAGG-3' (SEQ ID NO: 6) and 5'-CACA-CAAAGCTTTACTCTGAGCTTCTTGCAT-3' (SEQ ID NO: 7) were used in the PCR amplification. HeLa cells were transfected with the antisense JAB1 construct in the presence or absence of 1 μg/ml doxycycline. The transfected cells were harvested 36-48 hours post transfection and analyzed by western blotting as described in Example 3. The results of the western blot are shown in FIG. 11A, and these are quantitated in FIG. 11B. In the absence of doxycycline, the antisense JAB1 construct significantly down-regulated the amount of JAB1 protein, while the level of p27 protein increased in the absence of doxycycline.

It is believed that contacting a tumor cell with the siRNA or antisense constructs described herein provides methods of treating cancer by reducing the expression of JAB1 protein in the cell. It is recognized that other methods may be used to reduce the expression of JAB1 proteins in cells, such as cancer cells, and such methods are considered to be within the scope of this invention.

Example 12

Knockdown of JAB1 Expression with Antisense or siRNA Compositions

FIGS. 11A-11C show that depletion of endogenous JAB1 with either antisense (AS) or siRNA but not control siRNA, promotes p27-increased stability and leads to G1-arrest. In FIG. 11A, expression of antisense JAB1 increased the endogenous level of p27. HeLa cells were transfected with a tetracycline-inducible (Tet-Off system) antisense JAB1. Cell lysates were immunoblotted with JAB1 and p27 antibodies Quantification of the immunoblots is shown on the right. In FIG. 11B, there is depletion of JAB1 by siRNA oligos in HeLa cells. Cells were transfected with siRNA targeting JAB1 (JAB1 siRNA) or a scrambled sequence (Control siRNA). Forty-eight hours after transfection, cell lysates were prepared and were subjected to western blotting analysis using anti-JAB1, anti-p27, anti.Cyclin A, anti-pRb and anti-actin antibodies. For kinase assay (last panel), Cyclin A was immunoprecipitated from cell lysates and analyzed for cyclinA/Cdk2-associated activity using Histone 1B as a substrate. In FIG. 11C, knockdown of endogenous JAB1 expression decreases the S-phase progression in cell cycle and increases 5 G1 cells. Hela cells transfected with JAB1 siRNA and Control siRNA. Progression through S-phase was measured with anti-Brdu fluorescent antibodies and propidium idodide (PI) staining for Flow cytometry analysis.

Figure 12:
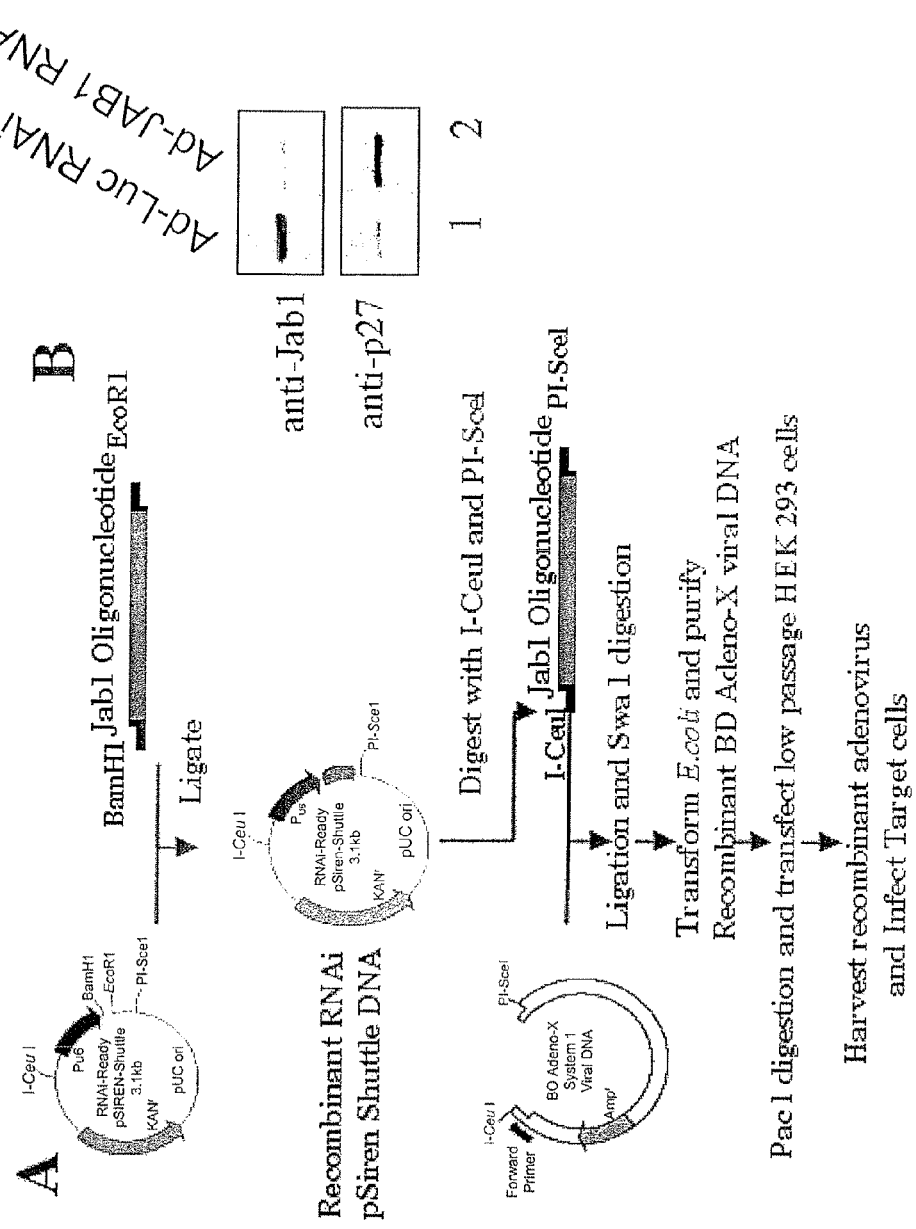
FIG. 12 shows silencing with adenoviral vector expressing JAB1siRNA (Ad-JAB1siRNA).

FIG. 12 shows silencing with adenoviral vector expressing JAB1siRNA (Ad-JAB1siRNA). In FIG. 12A, there is a schematic of pSIREN Adeno strategy (Adeno-X viral DNA, BD-Pharmingen). In FIG. 12B, inhibition of endogenous JAB1 with Ad-JAB1 siRNA but not with control Ad-LUCsiRNA, increases p27 expression levels. HeLa cells were transduced (MOI 50) with either Luciferase-RNAi pSIREN Shuttle vector or JAB1-RNAi pSIREN Shuttle vector. Cells were harvested 48 hours post-transfection and analyzed by western blotting analysis using both anti-JAB1 and anti-p27 antibodies.

Figure 13:
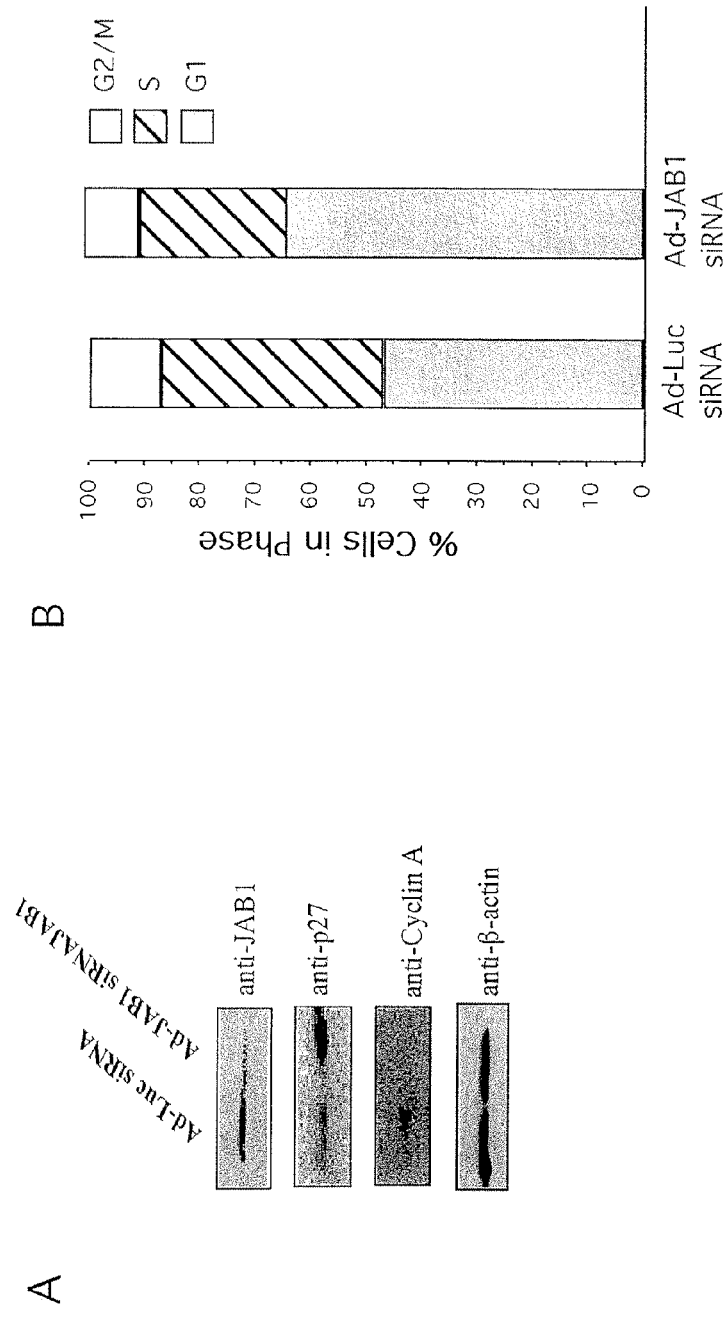
FIGS. 13A-13B demonstrate that depletion of JAB1 by siRNA adenovirus causes accumulation of p27kip1 and induces G1 arrest in MDA-MB 231 breast carcinoma cells.

FIGS. 13A-13B demonstrate that depletion of JAB1 by siRNA adenovirus causes accumulation of p27Kip1 and induces G1 arrest in MDA-MB 231 breast carcinoma cells. In FIG. 13A, MDA-MB 231 cells were transduced with adenoviruses driven JAB1 siRNA, or Luciferase siRNA as a control, at MOI 50. Forty eight hours after, protein lysates were prepared and immunoblotted with an anti-JAB1, anti-p27 and anti-Cyclin A antibodies. Anti-β actin was used as a loading control. SiRNA ablation of JAB1 increases the steady-state level of p27Kip1 protein and decreased cyclin A levels. In FIG. 13B, siRNA ablation of JAB1 induces G1 arrest. Cells were treated same as in FIG. 13A, and cell cycle profile was determined by propidium iodine staining and FACS.

FIG. 14 demonstrates that siRNA ablation of JAB1 causes p27kip1 accumulation and prevents S-phase re-entry in Karpas 299 T-cells lymphoma. In FIG. 14A, knockdown of JAB1 protein levels by siRNA increases the steady-state level of p27 protein, decreases cyclin A and phopho-Rb levels. Karpas 299 cells were transfected with p-Siren JAB1 siRNA or luciferase siRNA as a control (5 μg each). Lysates were immunoblotted 48 h after with the indicated antibodies. In FIG. 14B, siRNA ablation prevents S-phase re-entry. Karpas 299 cells were treated as in FIG. 14A, and progression through S-phase was measured with anti-BrdU fluorescent antibodies and FACS 48 hr after. Forty-six % of control siRNA-treated cells were in S-phase compared to 15% with siRNA JAB1.

Example 13

Delineation of the JAB1-JUN and JAB1-p27 Interaction Domains

Figure 17:
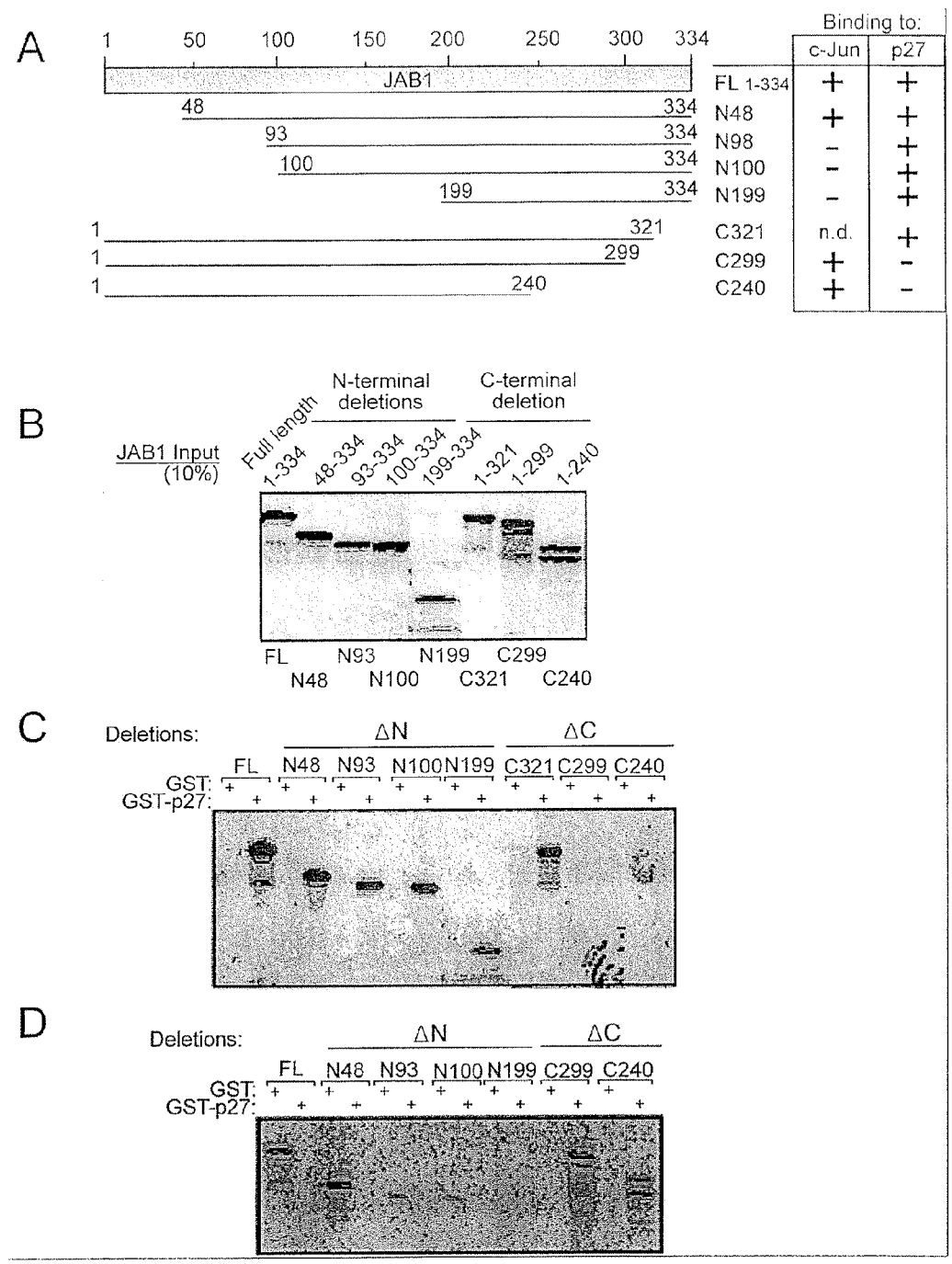
FIGS. 17A-17D show delineation of the JAB1-JUN interaction domain and JAB1-p27 interaction domain.

In order to map the interaction domains for p27 and JUN in JAB1, sequential N-terminal and C-terminal deletion constructs were made and tested. In vitro expression analysis of JAB1 full length, C- and N-terminal deletion mutants was performed using a TnT-coupled reticulocyte lysate system (Promega, Madison, Wis.). Lysates from the full length and deletion mutants were translated in vitro and labeled with [$^{35}$S]-methionine. Ten percent of the labeled products were separated on SDS-PAGE (FIG. 17B). The gel was then fixed and dried, and autoradiography was performed. Next, an in vitro binding assay was performed by incubating the translation products from the full length, C- and N-terminal deletion mutants with either glutathione-S-transferase (GST) alone or a GST-p27 fusion protein, each of which being immobilized on glutathione agarose. The results of the binding assay (summarized in FIG. 17A) showed that all N-terminal deletion mutants bound p27, but no C-terminal mutant bound p27. Such a result indicates that p27 finds to JAB1 at a position of about amino acid 299 to amino acid 334 (FIG. 17C).

Similarly, analysis was performed for determining the interaction domain for c-Jun. Again, full length, C- and N-terminal deletion mutants with either glutathione-S-transferase (GST) alone or a GST-c-Jun fusion protein (amino acids 1-79), each of which was immobilized on glutathione agarose (FIG. 17D). The results of the binding assay (summarized in FIG. 17A) showed that all C-terminal mutants bound c-Jun, but none of the N-terminal mutants bound p27, indicating that c-Jun binds to JAB1 at the JAB1 N-terminus between amino acid 49 and amino acid 96. The binding motifs delineated with these studies are the p27 binding domain on JAB1 (aa 298-334)-LAKATRDSCKTTIEAIHGLMSQVIKD-KLFNQINIS (SEQ ID NO:11) and the c-Jun docking domain on JAB1 (aa 49-92): HHYFKYCKISALALLKMVM-HARSGGNLEVMGLMLGKVDGETMIIM (SEQ ID NO: 12). In specific embodiments, these binding domain sequences are delineated further with similar or analogous studies (see below).

Figure 18:
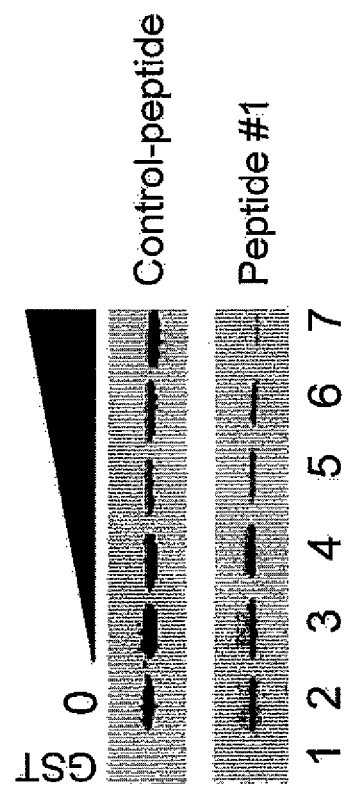
FIGS. 18A-18B show a small region of JAB1 is sufficient for interaction with p27. Recombinant proteins were bacterially expressed and purified as Glutathione-S-transferase (GST) alone or fused to p27 (GST-p27). Results of a GST (lane 1) or GST-p27 (lanes 3-7) pull-down experiments with in vitro $^{35}$S-methionine labeled JAB1 (full length) is shown. The effect of increasing concentrations (0, 0.08, 0.4, 2, 10 and 20 µg/ml) of synthetic JAB1-peptide (SEQ ID NO:13) #1 corresponding to JAB1-p27 binding-domain (18 amino acid residues) (Bottom panel, lanes 2-7) or to a peptide with scrambled sequence (control) was examined (Top panel, lanes 2-7). Reactions were incubated 1 hr at room temperature and washed 5 times and bound proteins to glutathione-Sepharose beads were loaded onto an SDS-PAGE. Autoradiogram is shown after $^{35}$S exposure.

FIGS. 18A-18B show a small region of JAB1 is sufficient for interaction with p27. Recombinant proteins were bacterially expressed and purified as Glutathione-S-transferase (GST) alone or fused to p27 (GST-p27). Results of a GST (lane 1) or GST-p27 (lanes 3-7) pull-down experiments with in vitro $^{35}$S-methionine labeled JAB1 (full length) is shown (FIG. 18A). The effect of increasing concentrations (0, 0.08, 0.4, 2, 10 and 20 µg/ml) of synthetic JAB1-peptide #1 corresponding to JAB1-p27 binding-domain (LAKATRDSCKT-TIEAIHG; SEQ ID NO:13; FIG. 18B) (Bottom panel, lanes 2-7) or to a peptide with scrambled sequence (control) was examined (Top panel, lanes 2-7). Reactions were incubated 1 hr at room temperature and washed 5 times and bound proteins to glutathione-Sepharose beads were loaded onto an SDS-PAGE. Autoradiogram is shown after $^{35}$S exposure.

Example 14

Sensitization of Herceptin Therapy by JAB1

Recently, the receptor HER2 (erbB2/neu) was found to be overexpressed in approximately 20%-30% of breast cancers and is an indicator of aggressiveness, poor prognosis, and poor response to tamoxifen (Slamon et al., 1987; Ross and Fletcher, 1998). Herceptin (trastuzumab), a humanized antibody to the receptor HER2, was developed (Carter et al, 1992) to block HER2 signaling and was tested in clinical trials in women with HER2 overexpressing tumors (Carter et al., 1992; Baselga et al, 1999; Arteaga, 2003; Slamon et al., 2001; Vogel et al., 2002). Treatment with Herceptin in HER2-overexpressing tumors is advantageous over standard chemotherapy because of less adverse side effects. However, the response ranges only from 12%-34%, and many HER2 positive tumors remain non-receptive to Herceptin treatment. In order to obtain the full benefit of this new drug, we need to understand the mechanism of drug resistance in these tumors.

An interesting link between drug resistance and p27, a potent inhibitor of cell division, offers one mechanism by which breast tumors evade Herceptin treatment. Cytoplasmic mislocalization of p27 and subsequent inactivation (Tomoda et al., 1999) was seen in 40% of tumors of various types of human cancers, and its sequestration were significantly higher in the tumors than in normal tissues (Loda et al., 1997; Guo et al., 1997; Masciullo et al., 1999; Singh et al., 1998; Ciaparrone et al., 1998). Decreased protein level of p27 is an important clinical marker that correlates with poor prognosis in breast and colorectal cancers (Loda et al., 1997; Catzavelos et al., 1997) as well as lung, colon, ovarian, skin, lymphoma, gastric, pituitary adenoma, and prostate adenocarcinoma (Guo et al., 1997; Esposito et al., 1997; Tsihlias et al., 1999; Sgambato et al., 1997). Indeed, a link between HER2/neu signaling and JAB1 regulation affecting the turnover rate of p27 may exist. HER2 signaling leads to an increase in p27 levels and induces G1 cell cycle arrest and tumor growth inhibition (Yang et al., 2000). A recent report by Yang et al., indicated that in breast cancer cells, overexpression and activation of HER2/neu proto-oncogene leads to mislocalization of p27 to the cytoplasm, thereby facilitating p27 degradation (Yang et al., 2001). Thus, in specific embodiments, a JAB1-overexpressing tumor provides a protective barrier against Herceptin-mediated upregulation of p27. Further, that inhibition of JAB1 would increase the efficiency of Herceptin treatment. This mechanism of drug resistance presents useful targets for therapeutics intervention.

Therefore, the role of JAB1 in resistance to Herceptin treatment was characterized. Herceptin treatment leads to an increase in cellular p27 levels and G1 arrest. Using an adeno-JAB1 in herceptin sensitive SKBr3 and BT-474 cells (both cell lines are HER-2 overexpressing cells) it is determined whether JAB1 inhibits the effect of Herceptin through degradation of p27. Further, inhibition of JAB1 through siRNA technology provides a novel strategy to sensitize tumors to Herceptin-induced tumor growth arrest and apoptosis, such as is demonstrated in a herceptin-resistant model.

To determine whether overexpression of JAB1 is involved in a Herceptin pathway, HER2-overexpressing breast cancer cells, SKBR3 and BT474, are utilized. These cells express low levels of JAB1 and are transduced with a doxycyclin-regulated (Tet-Off system) adenovirus (Ad-JAB1) at 50 MOI. Further treatment with Herceptin (10 µg/mL) in the absence (−) or presence (+) of doxycycline (1 µg/mL) for 48 h, followed by western blotting and flow cytometry analysis, is performed. Western blotting of total cell lysates and also nuclear and cytoplasmic fractions will demonstrate the effect of JAB1 levels on p27 export into the cytoplasm and p27 protein degradation. It has been reported that Herceptin is unable to induce apoptosis in BT474 cells in cell culture, but does result in cell arrest. Additionally, Herceptin is able to induce apoptosis, not cell arrest, in SKBR3 cells. Therefore, the biological effects of Herceptin treatment in the presence or absence of exogenous JAB1 is assessed on cell cycle and apoptosis by flow cytometry analysis.

Next, it is determined whether inhibition of JAB1 increases the efficiency of Herceptin treatment. siJAB1 effectively lowers endogenous JAB1 levels and restabilizes p27 level. BT474 and SKBR3 cells are treated with Herceptin in the presence and absence of siRNA JAB1. Through western blotting the amount of p27 is determined in the cytoplasm versus the nucleus. In specific embodiments, siRNA reduces JAB1 levels inhibiting the transport of p27 into the nucleus and p27-degradation. Further, the ability of Herceptin to induce G1 arrest in BT474 cells and apoptosis in SKBR3 cells in the presence of siRNA JAB1 is analyzed, such as by flow cytometry. In particular aspects of the invention, there is a correlation between JAB1 levels and effective Herceptin treatment. Previous findings have shown that Herceptin increases p27 at the protein level and JAB1 is known to be an inhibitor of p27. In specific embodiments, inhibition of JAB1 leads tumor cells into cell cycle arrest.

Figure 24:
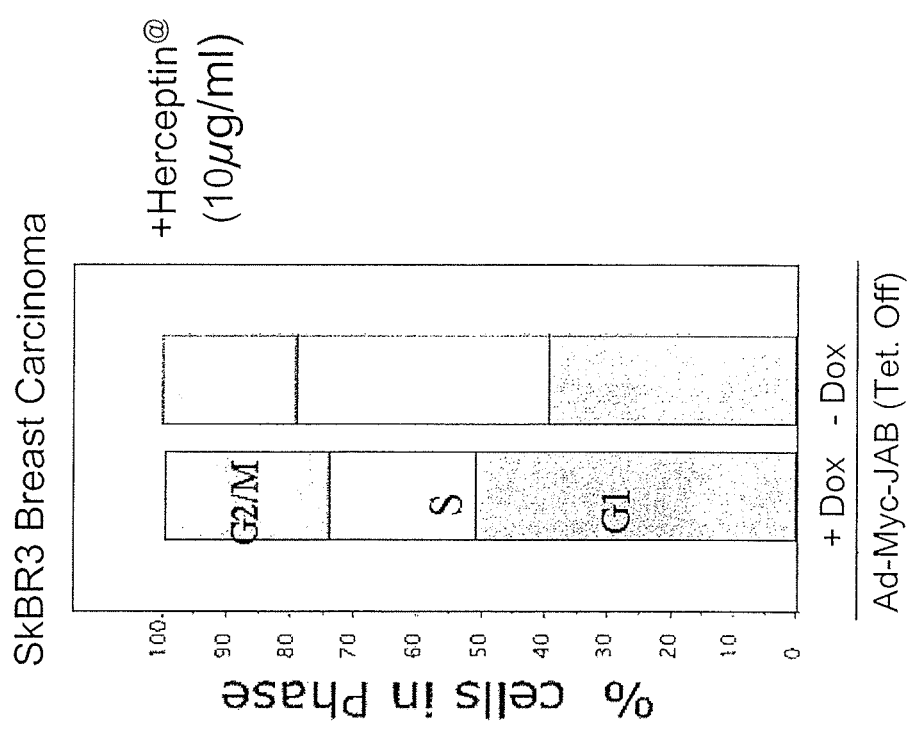
FIG. 24 shows that JAB1 bypasses Herceptin-mediated G1 arrest in breast cancer cells.

FIG. 24 shows that JAB1 bypass Herceptin-mediated G1 arrest in breast cancer cells. SKBR3 and BT474 express very low levels of JAB1 to undetectable and were plated (2×105 cells/well) 24 hr prior treatment. Then, cells were transduced with a doxycyclin-regulated (Tet-Off system) adenovirus (Ad-JAB1) at 20 MOI in presence (+) or absence (−) of Doxycyclin (a tetracycline analog) and were exposed or not to Herceptin treatment (10 µg/ml). 48 hr later all cells (suspension and adherent) were collected, stained with propidium iodine and analyzed by flow cytometry. Herceptin treatment causes an increase in G1 which was override upon Ad-JAB1 expression (−Dox) in these cells. Expression of JAB1 in these cells decreased the G1 by 11% and increase in S phase by 16%. A skilled artisan recognizes that Herceptin® (Genentech, South San Francisco, Calif.) is also referred to as trastuzumab, or humanized monoclonal IgG1.

Therefore, JAB1 siRNA and/or therapy targeted to inhibited JAB1 function can be utilized for improving herceptin therapy. Thus, in specific embodiments, JAB1-associated therapeutics are used in conjunction with herceptin or similar compositions.

Example 15

Clinicopathological Features of JAB1-Associated Cancer

Table 4 provides considerable data concerning clinocopathological features, JAB1 expression, p27 status, proliferative activity, and ploidy status for representative breast cancer patients. In specific embodiments, similar data is obtained by analogous methods for any other type of cancer.

Figure 19:
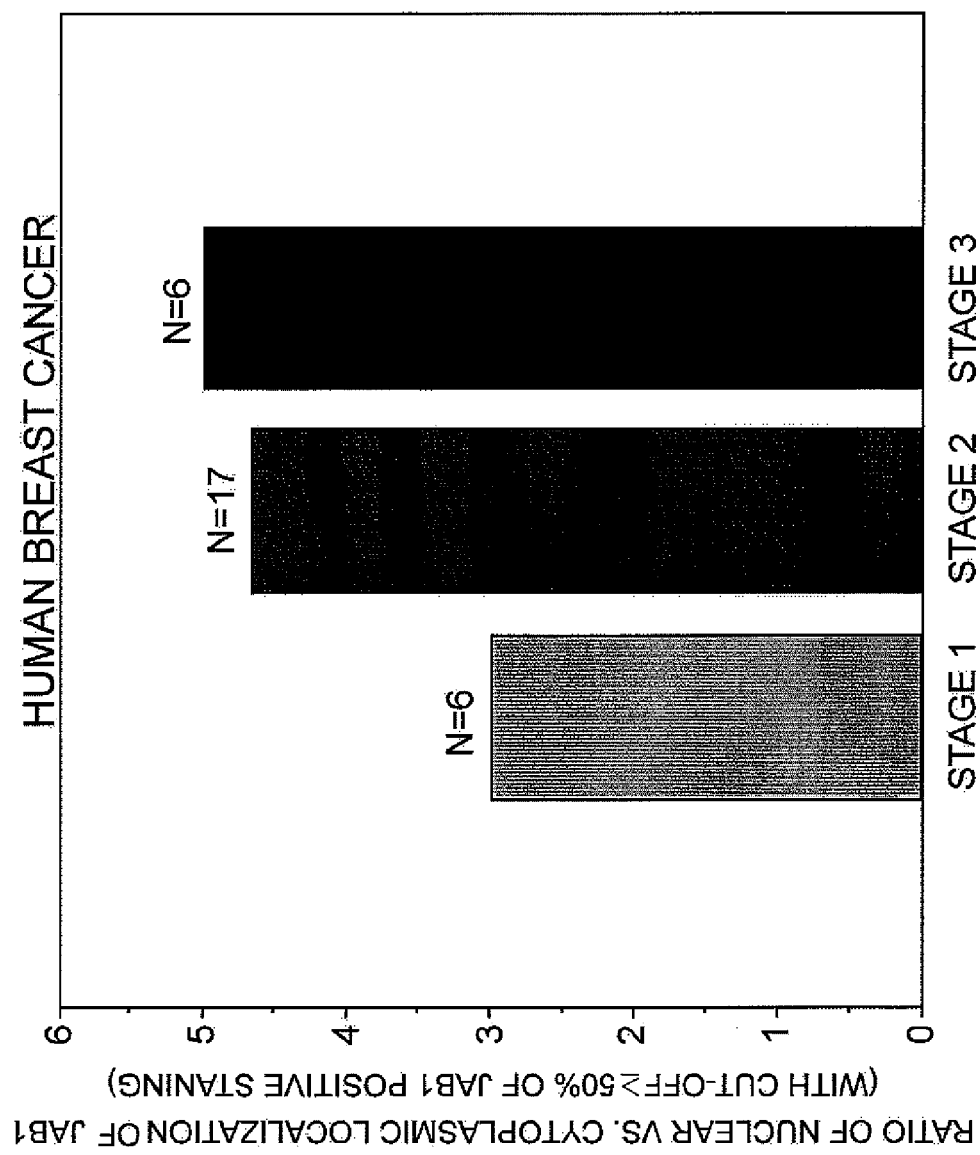
FIG. 19 illustrates nuclear vs. cytoplasmic localization of JAB1 correlating with stage of human breast cancer.

A variety of conclusions may be obtained from this data. For example, it can be seen that there is a correlation between high levels of JAB1 expression in the nucleus and low levels of p27 expression. This can be further associated with later stages of breast cancer (FIG. 19).

By extracting data from Table 4, the value corresponding to the ratio of nuclear vs. cytoplasmic localization of JAB1 among all JAB1 positive tumors having more than ≥50% staining was determined. This shows that there is a direct correlation between the presence of JAB1-positive staining in the nucleus with stage progression in breast cancer. In specific embodiment, the ratio for Stage I JAB1 nuclear vs. cytoplasmic expression is about 3.0; the ratio for Stage II JAB1 nuclear vs. cytoplasmic expression is about 4.66; and the ratio for Stage III JAB1 nuclear vs. cytoplasmic expression is about

TABLE 4

SUMMARY OF CLINICOPATHOLOGICAL FEATURES, JAB1 EXPRESSION, P27 STATUS, PROLIFERATIVE ACTIVITY, AND PLOIDY STATUS

| SAMPLE | AGE | HISTOLOGY | T. SIZE | GRADE | LN | STAGE | ER | PR | % nuclear JAB1 | Localiz. of JAB1 | p27(LI) | MIB1(PI) |
|---|---|---|---|---|---|---|---|---|---|---|---|---|
| 2 | 75 | MIXED | 3 | 2 | positive | II | negative | positive | 95 | N | 6% | 18% |
| 5 | 65 | IDC | 2.4 | 3 | negative | II | negative | positive | 85 | N | 12% | 5% |
| 6 | 77 | IDC | 2.2 | 2 | negative | II | positive | positive | 50 | C | <0.5% | 9% |
| 7 | 73 | IDC | 1 | 2 | positive | II | ND | ND | 98 | N | 55% | 8% |
| 8 | 52 | IDC | 2.6 | 3 | positive | II | positive | positive | 0 | | 55% | 26% |
| 10 | 51 | IDC | 5 | 2 | positive | III | positive | positive | 40 | N | 24% | 10% |
| 11 | 67 | IDC | 7.8 | 2 | positive | II | positive | positive | 76 | N | 6% | 7% |
| 12 | 48 | IDC + DCIS | 3.8 | 1 | Negative | II | positive | negative | 65 | C | <0.5% | ND |
| 13 | 42 | IDC | 2.8 | 3 | Negative | II | negative | positive | 0 | | <0.5% | 11% |
| 14 | 66 | IDC | 7 | 2 | Positive | III | positive | negative | 68 | N | 42% | 33% |
| 15 | 68 | IDC | 4.2 | 2 | Positive | III | negative | negative | 75 | N | <0.5% | ND |
| 16 | 61 | IDC | 5 | 2 | Positive | III | positive | positive | 45 | N | 34% | 20% |
| 17 | 35 | IDC | 2 | 3 | Positive | II | negative | negative | 90 | C | <0.5% | 42% |
| 18 | 64 | IDC | 2 | 3 | Positive | II | positive | positive | 75 | N | 40% | 17% |
| 19 | 71 | MIXED | 1.8 | 2 | Positive | II | ND | ND | 5 | N | 35% | 16% |
| 20 | 48 | IDC | 5 | 2 | Positive | III | positive | positive | 90 | N | 46% | 15% |
| 21 | 58 | IDC | 2.5 | 3 | Negative | III | negative | negative | 95 | N | 39% | 72% |
| 22 | 67 | IDC | 3 | 2 | Negative | II | positive | positive | 50 | N | 3% | 24% |
| 23 | 73 | ILC | 2.6 | 2 | Negative | II | positive | positive | 80 | N | 4% | 14% |
| 24 | 39 | IDC | 2.2 | 3 | Positive | II | positive | negative | 30 | N | 21% | 83% |
| 25 | 70 | IDC | 4.8 | 2 | Positive | III | positive | positive | 5 | N | 69% | 14% |
| 26 | 51 | IDC | 4 | 3 | Positive | II | positive | positive | 30 | N | 76% | 14% |
| 27 | 67 | IDC + DCIS | 2 | 2 | Negative | II | positive | positive | 80 | N | 3% | 13% |
| 28 | 62 | IDC | 3 | 2 | Positive | II | positive | positive | 95 | N | 33% | 19% |
| 29 | 72 | IDC | 2 | 1 | Positive | II | positive | positive | 95 | N | 85% | 16% |
| 30 | 76 | IDC | 0.9 | 2 | Negative | I | negative | positive | 70 | N | 32% | 32% |
| 31 | 54 | ILC | 4.5 | 2 | Positive | IV | ND | ND | 30 | N | ND | ND |
| 33 | 64 | IDC | 5 | 3 | Positive | III | negative | negative | 1 | N | 85% | 28% |
| 35 | 81 | IDC | 2 | 1 | Negative | I | positive | positive | 70 | C | 12% | ND |
| 36 | 67 | IDC | 5.2 | 3 | Positive | IV | positive | negative | 30 | N | 34% | 41% |
| 37 | 75 | IDC | 10 | 2 | Positive | IV | positive | positive | 80 | N | 63% | 16% |
| 38 | 66 | IDC | 5 | 3 | Positive | II | positive | positive | 75 | N | ND | 7% |
| 39 | 69 | IDC | 3 | 2 | Negative | II | ND | ND | 5 | N | 15% | ND |
| 40 | 65 | IDC | 5 | 3 | Positive | III | positive | negative | 5 | N | 78% | 16% |
| 41 | 60 | IDC | 1.5 | 2 | Negative | I | ND | ND | 40 | N | 40% | 24% |
| 42 | 88 | IDC | 7.5 | 3 | Positive | IV | ND | ND | 65 | C | <0.5% | ND |
| 43 | 37 | IDC + DCIS | 11.2 | 3 | Negative | II | positive | negative | 0 | | ND | 31% |
| 44 | 52 | IDC | 3.6 | 3 | Negative | II | positive | negative | 97 | N | 31% | ND |
| 45 | 90 | IDC | 4.2 | 2 | Negative | II | ND | ND | 95 | N | 42% | 9% |
| 48 | 65 | IDC | 3 | 3 | Positive | III | ND | ND | 0 | | 28% | 29% |
| 49 | 67 | ILC | 7.3 | 2 | Positive | III | positive | positive | 20 | N | 58% | 11% |
| 50 | 64 | IDC | 3 | 2 | Positive | II | ND | ND | 90 | N | <0.5% | 12% |
| 51 | 66 | IDC | 4.4 | 3 | Positive | III | positive | positive | 55 | N | 35% | 21% |
| 52 | 48 | IDC | 2.5 | 1 | Positive | II | positive | negative | 30 | N | 53% | 9% |
| 53 | 39 | IDC | 8.5 | 2 | Positive | III | positive | positive | 0 | | ND | 14% |
| 55 | 60 | IDC + DCIS | 2 | 1 | Positive | I | ND | ND | 60 | N | 21% | 22% |
| 56 | 54 | IDC | 6 | 2 | Negative | II | negative | negative | 60 | N | 43% | 10% |
| 57 | 53 | IDC | 9 | 3 | Positive | III | negative | negative | 55 | C | 14% | 13% |
| 58 | 46 | IDC | 9.5 | 2 | Positive | II | positive | positive | 25 | N | 54% | 17% |
| 60 | 74 | IDC | 1.8 | 2 | Negative | I | positive | negative | 70 | N | 20% | 10% |
| 61 | 88 | IDC | 7 | 2 | Negative | II | positive | positive | 90 | N | 42% | 12% |
| 62 | 81 | IDC | 2 | 2 | Negative | I | ND | ND | 20 | N | 41% | 15% |

5. Thus, by determining JAB1 levels and its subcellular localization (nuclear versus cytoplasmic, for example), this is an indicator of tumor progression.

Example 16

Characterization of JAB1 Promoter Region and Transcriptional Start Site

FIGS. 20A-20C demonstrate characterization of the JAB1 promoter region and its transcriptional start site. In FIG. 20A, 1, 2 and 3 kb upstream of the mRNA start site have been amplified by PCR, and the JAB1 promoter regions were predicted by using Proscan V1.7. Primers were designed to amplify 1, 2, and 3 kb upstream of the ATG. In FIG. 20B, PCR amplification products of the predicted regions are identified on the agarose gel. In FIG. 20C, there is the transcriptional start site of the Jab1 gene. Primer extension from 20 μg of total RNA from human cells using a JAB1 specific primer and the Promega provided control is shown. The primer extension product (+P) marks the start of transcription. Sequencing using the same primer is shown (G,A,T,C). Seventy-seven nucleotides in the G lane corresponds to the band in the primer extension lane.

FIG. 21 provides the reverse complement of the JAB1 promoter sequence and the corresponding transcription factor binding sites, as well as the transcription start site at +1. This sequence is provided as SEQ ID NO:17 and is included at a GenBank Gene ID No. 10987. SEQ ID NO:18 provides a reverse complement sequence upstream of JAB1 comprising about 3 kb 5' of the ATG start of Jab1.

Thus, in specific embodiments, the promoter region of JAB1 is utilized for methods and/or compositions suitable for the invention. Exemplary therapeutics may target inhibition of these regulatory regions by interfering with a regulator (such as a transcription factor) that binds to these specific cis-regulatory DNA regions. Specific-DNA competitions aimed to inhibit these bindings could be utilized as well. Thus, using the promoter region to screen for one or more drug/small inhibitors that may inhibit JAB1 mRNA expression, and therefore protein production, is within the scope of the invention.

Example 15

Jab1/p27 Expression in Normal and Neoplastic Pancreas

Figure 22:
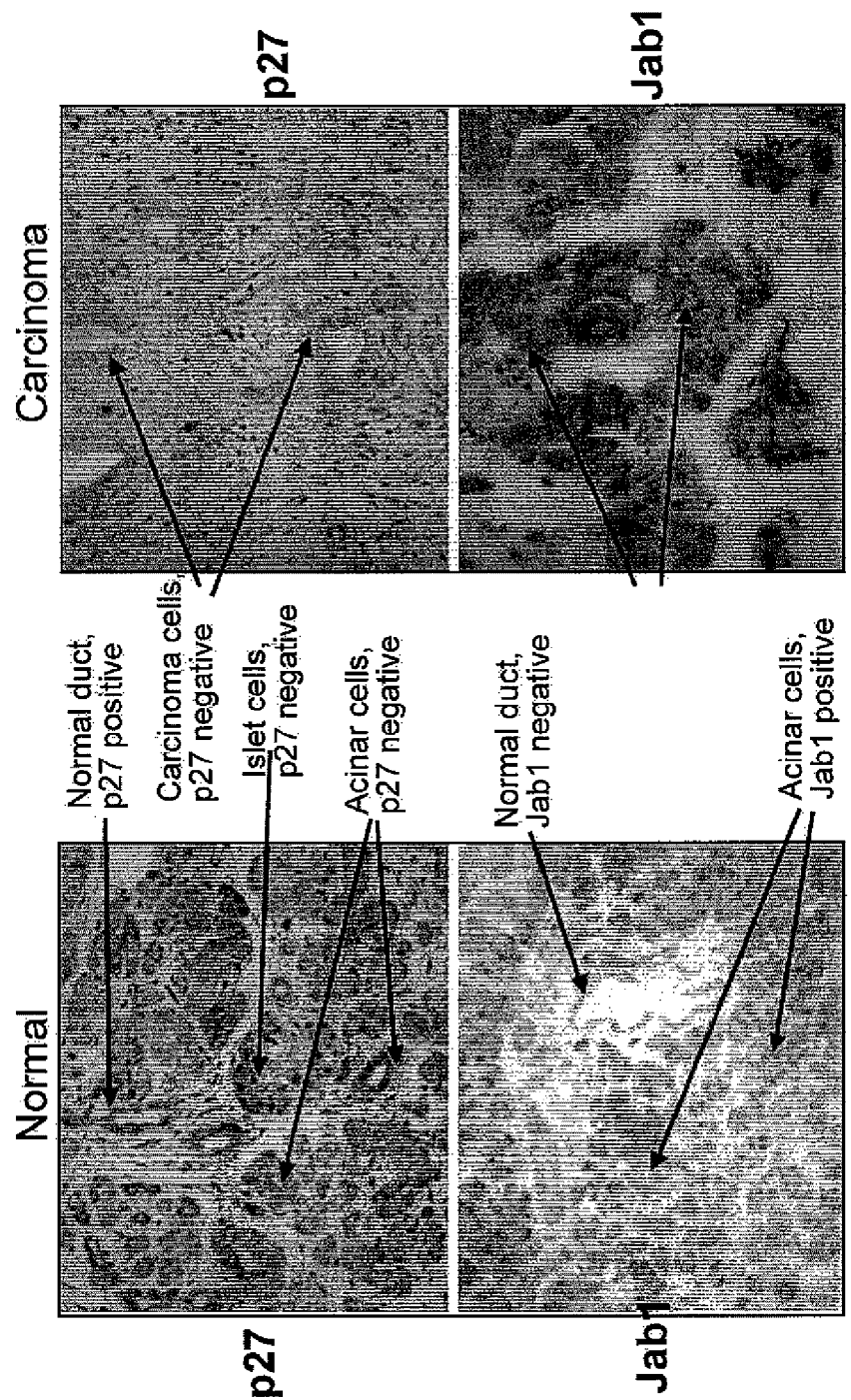
FIG. 22 shows JAB1 and p27 expression in normal and neoplastic pancreas. JAB1 and p27 immunostainings are shown (brown stainings). Three different type of cells comprise the pancreas: ductal, acinar and islet cells. Normal ducts are negative for JAB1 and positive for p27 stainings (Left panel). Neoplastic carcinoma arise from the duct cells that are positive for JAB1 and negative for p27 (Right panel). Brown staining is specific immunostainings. (−): negative; (+): Positive stainings.

JAB1/p27 expression was assayed in normal vs. neoplastic pancreatic tissue (FIG. 22). JAB1 and p27 immunostainings are shown in brown. Three different type of cells (ductal, acinar and islet cells) comprise the pancreas. Normal ducts are negative for JAB1 and positive for p27 stainings (Left panel). Neoplastic carcinoma arise from the duct cells that are positive for JAB1 and negative for p27 (Right panel). Brown staining illustrates specific immunostainings. (−): negative; (+): Positive stainings. Thus, in specific embodiments of the present invention, the scope of the invention comprises pancreatic cancer.

Example 16

Jab1/p27 Expression in Normal and Neoplastic Pancreas

Figure 23:
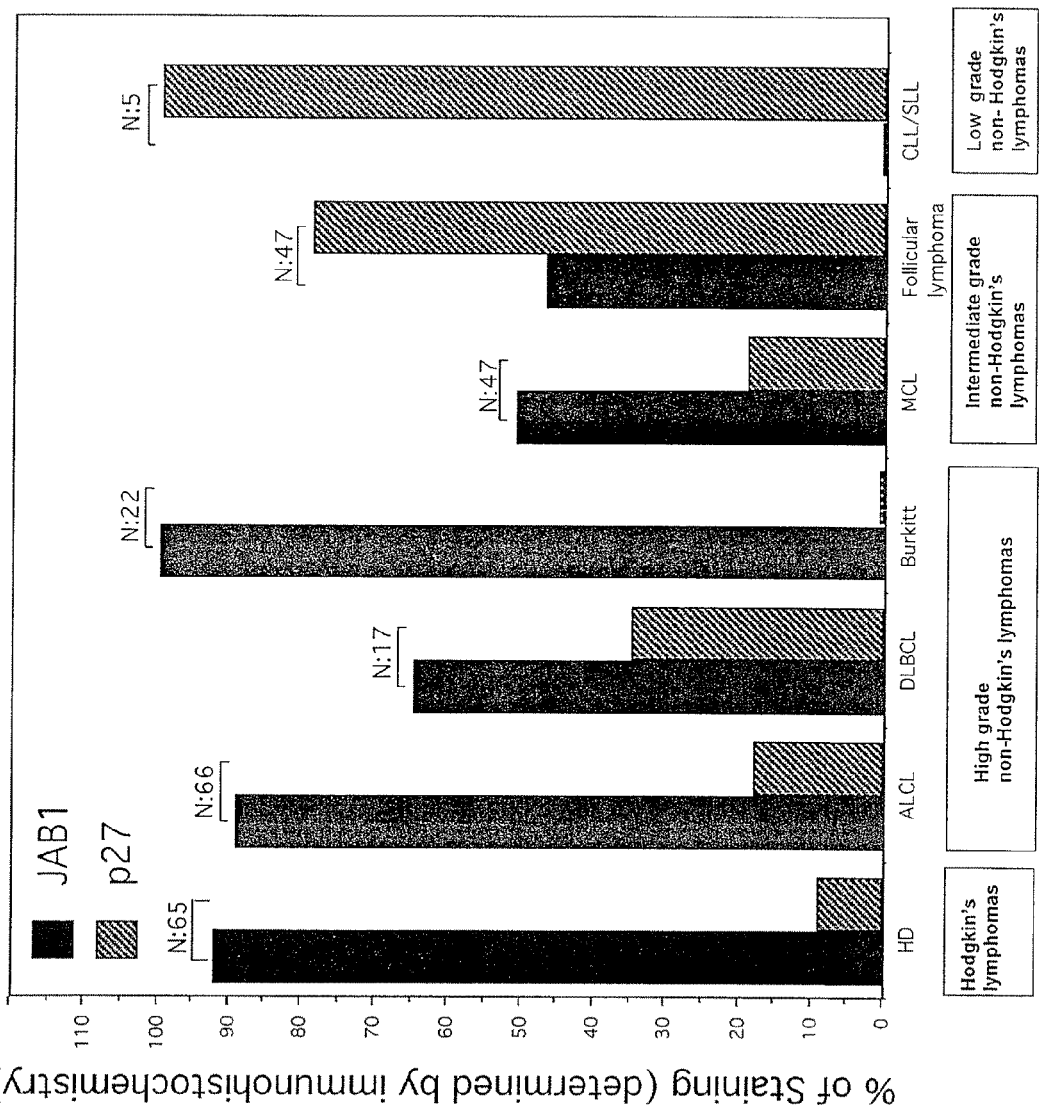
FIG. 23 shows p27 and JAB1 expression in lymphoma types including: Hodgkin's Lymphoma; high grade non-Hodgkin's lymphomas (ALCL, DLBCL and Burkitt); intermediate grade non-Hodgkin's lymphomas (MCL and follicular lymphoma); and low grade non-Hodgkin's lymphomas (CLL/SLL).

FIG. 23 shows p27 and JAB1 Expression in lymphoma types are demonstrated, including the following exemplary types: Hodgkin's Lymphoma; high grade non-Hodgkin's lymphomas (ALCL, DLBCL and Burkitt); intermediate grade non-Hodgkin's lymphomas (MCL and follicular lymphoma); and low grade non-Hodgkin's lymphomas (CLL/SLL). Thus, in specific embodiments of the present invention, the scope of the invention comprises lymphoma, such as Hodgkins' lymphoma or non-Hodgkin's lymphoma.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meaning as commonly understood to one of ordinary skill in the art to which this invention belongs.

REFERENCES

All publications mentioned herein are incorporated herein by reference for the purpose of describing and disclosing, for example, the methods and compositions that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

PATENTS AND PATENT APPLICATIONS

United States Patent Application Publication US 20020156012
United States Patent Application Publication US 20030148954
United States Patent Application Publication US 20030153097
United States Patent Application Publication US 20030166243
EP0856582

PUBLICATIONS

Arteaga C L. Trastuzumab, an appropriate first-line single-agent therapy for HER2-overexpressing metastatic breast cancer. Breast Cancer Res 2003; 5(2):96-100.

Bae, M. K., Ahn, M. Y., Jeong, J. W., Bae, M. H., Lee, Y. M., Bae, S. K., Park, J. W., Kim, K. R., and Kim, K. W. Jab1 interacts directly with HIF-1 alpha and regulates its stability. J. Biol. Chem., 277: 9-12, 2002.

Barnes, C. J., Li, F., Mandal, M., Yang, Z., Sahin, A. A., and Kumar, R. Heregulin induces expression, ATPase activity, and nuclear localization of G3BP, a Ras signaling component, in human breast tumors. Cancer Res., 62: 1251-1255, 2002.

Baselga J et al. Phase II study of weekly intravenous trastuzumab (Herceptin) in patients with HER2/neu-overexpressing metastatic breast cancer. Seminars in Oncology, Vol 26(4): Suppl. 12 pp 78-83, 1999.

Bianchi, E., Denti, S., Granata, A., Bossi, G., Geginat, J., VIIIa, A., Rogge, L., and Pardi, R. Integrin LFA-1 interacts with the transcriptional co-activator JAB1 to modulate AP-1 activity. Nature (Lond.), 404: 617-621, 2000.

Carter P, Presta L, Gorman C M et al. Humanization of an anti-p185HER2 antibody for human cancer therapy. Proc Natl Acad Sci USA 1992; 89(10):4285-4289.

Catzavelos, C., Bhattacharya, N., Ung, Y. C., Wilson, J. A., Roncari, L., Sandhu, C., Shaw, P., Yeger, H., Morava-Protzner, I., Kapusta, L., Franssen, E., Pritchard, K. I., and Slingerland, J. M. Decreased levels of the cell-cycle inhibitor p27Kip1 protein: prognostic implications in primary breast cancer. Nat. Med., 3: 227-230, 1997.

Chamovitz, D. A. and Segal, D. JAB1/CSN5 and the COP9 signalosome. A complex situation. EMBO Rep., 2: 96-101, 2001.

Ciaparronne M, Yamamoto H, Yao Y et al. Localization and expression of p27KIP1 in multistage colorectal carcinogenesis. Cancer Res 1998; 58:114-122.

Claret, F. X., Hibi, M., Dhut, S., Toda, T., and Karin, M. A new group of conserved coactivators that increase the specificity of AP-1 transcription factors. Nature (Lond.), 383: 453-457, 1996.

Esposito V, Baldi A, Pagano M, Giordano A. Prognostic role of the cyclin-dependent kinase inhibitor p27 in non-small cell lung cancer. Cancer Res 1997; 57:3381-3385.

Gee, J. M., Barroso, A. F., Ellis, I. O., Roberston, J. F. and Nicholson, R. I. Biological and clinical association of c-Jun activation in human breast cancer. Int. J. Cancer, 89, 177-186, 2000.

Guo Y, Sklar G N, Borkowski A, Kyprianou N. Loss of the cyclin-dependent kinase inhibitor p27(Kip1) protein in human prostate cancer correlates with tumor grade. Clin Cancer Res 1997; 3:2269-2274.

Ho A, Schwarze S R, Mermelstein S J, Waksman G, Dowdy S F.; Synthetic protein transduction domains: enhanced transduction potential in vitro and in vivo. Cancer Res. 2001 Jan. 15; 61(2):474-7

Kleemann, R., Hausser, A., Geiger, G., Mischke, R., Burger-Kentischer, A., Flieger, O., Johannes, F. J., Roger, T., Calandra, T., Kapumiotu, A., Grell, M., Finkelmeier, D., Brunner, H., and Bernhagen, J. Intracellular action of the cytokine MIF to modulate AP-1 activity and the cell cycle through Jab1. Nature (Lond.), 408: 211-216, 2000.

Korbonits, M., Chahal, H. S., Kaltsas, G., Jordan, S., Urmanova, Y., Khalimova, Z., Harris, P. E., Farrell, W. E., Claret, F. X., and Grossman, A. B. Expression of phosphorylated p27(Kip1) protein and Jun activation domain-binding protein 1 in human pituitary tumors. J. Clin. Endocrinol. Metab., 87: 2635-2643, 2002.

Kouvaraki, M., Gorgoulis, V. G., Rassidakis, G. Z., Liodis, P., Markopoulos, C., Gogas, J., and Kittas, C. High expression levels of p27 correlate with lymph node status in a subset of advanced invasive breast carcinomas: relation to E-cadherin alterations, proliferative activity, and ploidy of the tumors. Cancer, 94: 2454-2465, 2002.

Loda M, Cukor B, Tam S W et al. Increased proteasome-dependent degradation of the cyclin-dependent kinase inhibitor p27 in aggressive colorectal carcinomas. Nat Med 1997; 3:231-234.

Masciullo V, Sgambato A, Pacilio C et al. Frequent loss of expression of the cyclin-dependent kinase inhibitor p27 in epithelial ovarian cancer. Cancer Res 1999; 59:3790-3794.

Lu, C., Li, Y., Zhao, Y., Xing, G., Tang, F., Wang, Q., Sun, Y., Wei, H., Yang, X., Wu, C., Chen, J., Guan, K. L., Zhang, C., Chen, H., and He, F. Intracrine hepatopoietin potentiates AP-1 activity through JAB1 independent of MAPK pathway. FASEB J., 16: 90-92, 2002.

Malek, N. P., Sundberg, H., McGrew, S., Nakayama, K., Kyriakides, T. R., Roberts, J. M., and Kyriakidis, T. R. A mouse knock-in model exposes sequential proteolytic pathways that regulate p27Kip1 in G1 and S phase. Nature (Lond.), 413: 323-327, 2001.

Montagnoli, A., Fiore, F., Eytan, E., Carrano, A. C., Draetta, G. F., Hershko, A., and Pagano, M. Ubiquitination of p27 is regulated by Cdk-dependent phosphorylation and trimeric complex formation. Genes Dev., 13: 1181-1189, 1999.

Ozanne, B. W., McGarry, L., Spence, H. J., Johnston, I., Winnie, J., Meagher, L., and Stapleton, G. Transcriptional regulation of cell invasion: AP-1 regulation of a multigenic invasion programme. Eur. J. Cancer, 36: 1640-1648, 2000.

Pagano, M., Tam, S. W., Theodoras, A. M., Beer-Romero, P., Del Sal, G., Chau, V., Yew, P. R., Draetta, G. F., and Rolfe, M. Role of the ubiquitin-proteasome pathway in regulating abundance of the cyclin-dependent kinase inhibitor p27. Science (Wash. DC), 269: 682-685, 1995.

Polyak, K., Lee, M. H., Erdjument-Bromage, H., Koff, A., Roberts, J. M., Tempst, P., and Massague, J. Cloning of p27Kip1, a cyclin-dependent kinase inhibitor and a potential mediator of extracellular antimitogenic signals. Cell, 78: 59-66, 1994.

Rassidakis, G. Z., Claret, F.-X., Lai, R., Zhang, Q., Sarris, A. H., McDonnell, T. J., Medeiros, L. J. Expression of p27KIP1 and c-Jun activation binding protein 1 are inversely correlated in systemic anaplastic large cell lymphoma. Clin. Cancer Res. 9:1121-1128, 2003.

Ross J S, Fletcher J A. The HER-2/neu oncogene in breast cancer: prognostic factor, predictive factor, and target for therapy. Stem Cells 1998; 16(6):413-428.

Sanchez-Beato, M., Camacho, F. I., Martinez-Montero, J. C., Saez, A. I., Villuendas, R., Sanchez-Verde, L., Garcia, J. F., and Piris, M. A. Anomalous high p27/KIP1 expression in a subset of aggressive B-cell lymphomas is associated with cyclin D3 overexpression. p27/KIP1-cyclin D3 colocalization in tumor cells. Blood, 94: 765-772, 1999.

Schwechheimer, C. and Deng, X. W. COP9 signalosome revisited: a novel mediator of protein degradation. Trends Cell Biol., 11: 420-426, 2001.

Schwarze S R, Ho A, Vocero-Akbani A, Dowdy S F. In vivo protein transduction: delivery of a biologically active protein into the mouse. Science. 1999 Sep. 3; 285(5433): 1569-72.

Seeger, M., Kraft, R., Ferrell, K., Bech-Otschir, D., Dumdey, R., Schade, R., Gordon, C., Naumann, M., and Dubiel, W. A novel protein complex involved in signal transduction possessing similarities to 26S proteasome subunits. FASEB J., 12: 469-478, 1998.

Sgambato A, Zhang Y J, Arber N et al. Deregulated expression of p27(Kip1) in human breast cancers. Clin Cancer Res 1997; 3(10):1879-1887.

Sheaff, R. J., Groudine, M., Gordon, M., Roberts, J. M., and Clurman, B. E. Cyclin E-CDK2 is a regulator of p27Kip1. Genes Dev., 11: 1464-1478, 1997.

Shen, L., Tsuchida, R., Miyauchi, J., Saeki, M., Honna, T., Tsunematsu, Y., Kato, J., Mizutani, S. Differentiation-associated expression and intracellular localization of cyclin-dependent kinase inhibitor p27KIP1 and c-Jun coactivator JAB1 in neuroblastoma. Int. J. Oncol. 17(4): 749-54, 2000.

Singh S P, Lipman J, Goldman H et al. Loss or altered subcellular localization of p27 in Barrett's associated adenocarcinoma. Cancer Res 1998; 58:1730-1735.

Sherr, C. J. and Roberts, J. M. CDK inhibitors: positive and negative regulators of G1-phase progression. Genes Dev., 13: 1501-1512, 1999.

Slamon D J, Clark G M, Wong S G, Levin W J, Ullrich A, McGuire W L. Human breast cancer: correlation of relapse and survival with amplification of the HER-2/neu oncogene. Science 1987; 235(4785):177-182.

Slamon D. J., et al. Use of chemotherapy plus a monoclonal antibody against HER2 for metastatic breast cancer that overexpresses HER2. The New England Journal of Medicine, Vol. 344 pp 783-792, 2001.

Smith, L. M., Wise, S. C., Hendricks, D. T., Sabichi, A. L., Bos, T., Reddy, P., Brown, P. H. and Birrer, M. J. c-Jun Overexpression in MCF-7 breast cancer cells produces a tumorigenic, invasive and hormone resistant phenotype. Oncogene, 18, 6063-6070, 1999.

Sui, L., Dong, Y., Ohno, M., Watanabe, Y., Sugimoto, K., Tai, Y., and Tokuda, M. Jab1 expression is associated with inverse expression of p27(kip1) and poor prognosis in epithelial ovarian tumors. Clin. Cancer Res., 7: 4130-4135, 2001.

Tomoda, K., Kubota, Y., and Kato, J. Degradation of the cyclin-dependent-kinase inhibitor p27Kip1 is instigated by Jab1. Nature (Lond.), 398: 160-165, 1999.

Tomoda, K., Kubota, Y., Arata, Y., Mori, S., Maeda, M., Tanaka, T., Yoshida, M., Yoneda-Kato, N., and Kato, J. Y. The cytoplasmic shuttling and subsequent degradation of p27Kip1 mediated by Jab1/CSN5 and the COP9 signalosome complex. J. Biol. Chem., 277: 2302-2310, 2002.

Tsihlias J, Kapusta L, Slingerland J. The prognostic significance of altered cyclin-dependent kinase inhibitors in human cancer. Annu Rev Med 1999; 50:401-423.

Vlach, J., Hennecke, S., and Amati, B. Phosphorylation-dependent degradation of the cyclin-dependent kinase inhibitor p27. EMBO J., 16: 5334-5344, 1997.

Vogel C. L et al. Efficacy and safety of trastuzumab as a single agent in first-line treatment of HER2-overexpressing metastatic breast cancer. Journal of Clinical Oncology, Vol 20, pp 719-726, 2002.

Wan, M., Cao, X., Wu, Y., Bai, S., Wu, L., Shi, X., and Wang, N. Jab1 antagonizes TGF-b signaling by inducing Smad4 degradation. EMBO Rep., 3: 171-176, 2002.

Yang H Y, Zhou B P, Hung M C, Lee M H. Oncogenic signals of HER-2/neu in regulating the stability of the cyclin-dependent kinase inhibitor p27. J Biol Chem 2000; 275: 24735-24739.

Yang H Y, Shao R, Hung M C, Lee M H. p27 Kip1 inhibits HER2/neu-mediated cell growth and tumorigenesis. Oncogene 2001; 20(28):3695-3702.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of determining a prognosis for cancer in an individual, the method comprising assessing a JAB1 protein labeling index in a sample of cancer cells, or cells suspected of being cancerous, from the individual, wherein a sample having a JAB1 labeling index of greater than 50% is indicative of a poor prognosis, wherein the cancer is ovarian cancer, breast cancer, non-Hodgkin's lymphoma, colon cancer, prostate cancer, pancreatic cancer, liver cancer, colorectal or lung cancer.

2. The method of claim 1, wherein the cancer is breast cancer, non-Hodgkin's lymphoma, liver cancer, colon cancer or colorectal cancer.

3. The method of claim 2, wherein the cancer is breast cancer.

4. The method of claim 1, wherein a JAB1 labeling index is defined as that level of JAB1 expression achieved when 50% or greater of cells in the sample are detectable by immunohistochemical testing using a JAB1 antibody.

5. The method of claim 1, further comprising assessing a p27 labeling index in the sample, wherein a sample having a p27 labeling index of lower than 50% is indicative of a poor prognosis.

6. The method of claim 1, wherein the JAB1 labeling index is assessed by immunohistochemistry, ELISA or FISH.

7. The method of claim 5, wherein the p27 labeling index is assessed by immunohistochemistry, ELISA or FISH.

8. The method of claim 1, wherein the cancer is non-Hodgkin's lymphoma.

9. The method of claim 1, wherein the cancer is colon cancer.

10. The method of claim 1, wherein the cancer is prostate cancer.

11. The method of claim 1, wherein the cancer is pancreatic cancer.

12. The method of claim 1, wherein the cancer is liver cancer.

13. The method of claim 1, wherein the cancer is colorectal cancer.

14. The method of claim 1, wherein the cancer is lung cancer.

15. The method of claim 1, wherein the cancer is ovarian cancer.

* * * * *

UNITED STATES PATENT AND TRADEMARK OFFICE
CERTIFICATE OF CORRECTION

PATENT NO.       : 8,722,340 B2                                  Page 1 of 1
APPLICATION NO.  : 11/874838
DATED            : May 13, 2014
INVENTOR(S)      : Francois Claret It is certified that error appears in the above-identified patent and that said Letters Patent is hereby corrected as shown below:

In the Specification

In column 1, lines 17-20, delete "This invention was made with U.S. Government support from the National Cancer Institute/National Institutes of Health Grant number 1RO1CA90853-01A1. The U.S. Government may have certain rights in this invention." and insert --This invention was made with Government support under grant number 1RO1CA90853-01-A1 awarded by the National Institutes of Health. The Government has certain rights in the invention.-- therefor.

Signed and Sealed this
Twelfth Day of August, 2014

Michelle K. Lee
*Deputy Director of the United States Patent and Trademark Office*